US012721890B2

(12) United States Patent
Kim et al.

(10) Patent No.: US 12,721,890 B2
(45) Date of Patent: Sep. 1, 2026

(54) T CELL RECEPTORS RECOGNIZING R273C OR Y220C MUTATIONS IN P53

(71) Applicant: The United States of America,as represented by the Secretary,Department of Health and Human Services, Bethesda, MD (US)

(72) Inventors: Sanghyun Kim, Rockville, MD (US); Nikolaos Zacharakis, Gaithersburg, MD (US); Steven A. Rosenberg, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 799 days.

(21) Appl. No.: 18/024,557

(22) PCT Filed: Sep. 2, 2021

(86) PCT No.: PCT/US2021/048786

§ 371 (c)(1),
(2) Date: Mar. 3, 2023

(87) PCT Pub. No.: WO2022/051449

PCT Pub. Date: Mar. 10, 2022

(65) Prior Publication Data

US 2023/0321240 A1 Oct. 12, 2023

Related U.S. Application Data

(60) Provisional application No. 63/074,747, filed on Sep. 4, 2020.

(51) Int. Cl.

| | |
|---|---|
| ***A61K 40/32*** | (2025.01) |
| ***A61K 40/11*** | (2025.01) |
| ***A61K 40/42*** | (2025.01) |
| ***C07K 14/705*** | (2006.01) |
| ***C12N 5/0783*** | (2010.01) |
| ***C12N 15/86*** | (2006.01) |
| *A61K 40/50* | (2025.01) |

(52) U.S. Cl.

CPC .............. *A61K 40/11* (2025.01); *A61K 40/32* (2025.01); *A61K 40/4241* (2025.01); *C07K 14/7051* (2013.01); *C12N 5/0636* (2013.01); *C12N 15/86* (2013.01); *A61K 40/50* (2025.01); *C07K 2319/50* (2013.01); *C12N 2501/2302* (2013.01); *C12N 2740/10043* (2013.01)

(58) Field of Classification Search

None

See application file for complete search history.

(56) References Cited

U.S. PATENT DOCUMENTS

| | | | |
|---|---|---|---|
| 8,034,334 | B2 | 10/2011 | Dudley et al. |
| 8,383,099 | B2 | 2/2013 | Dudley et al. |
| 10,174,098 | B2 | 1/2019 | Hinrichs et al. |
| 2012/0244133 | A1 | 9/2012 | Rosenberg et al. |

FOREIGN PATENT DOCUMENTS

| | | | |
|---|---|---|---|
| WO | WO 2018/102585 | A1 | 6/2018 |
| WO | WO 2019/036688 | A1 | 2/2019 |
| WO | WO 2019/067242 | A1 | 4/2019 |
| WO | WO 2019/067243 | A1 | 4/2019 |
| WO | WO 2024/206274 | A2 | 10/2024 |

OTHER PUBLICATIONS

Murphy et al., eds., Janeway's Immunobiology, 7th Ed., New York: Garland Science (2008), pp. 157-158 (Section 4-10).

Quandt et al., "Long-peptide vaccination with driver gene mutations in p53 and Kras induces cancer mutation-specific effector as well as regulatory T cell responses", OncoImmunology, 7:12, e1500671, 22 pages (2018).

Cohen et al., "Enhanced Antitumor Activity of Murine-Human Hybrid T-Cell Receptor (TCR) in Human Lymphocytes Is Associated with Improved Pairing and TCR/CD3 Stability", *Cancer Research,* 66(17): 8878-8886 (2006).

Cohen et al., "Enhanced Antitumor Activity of T Cells Engineered to Express T Cell Receptors with a Second Disulfide Bond", *Cancer Research,* 67(8): 3898-3903 (2007).

Deniger et al., "T-cell responses to TP53 "hotspot" mutations and unique neoantigens expressed by human ovarian cancers", *Clinical Cancer Research,* 24(22): 5562-5573 (2018).

Dudley et al., "Generation of Tumor-Infiltrating Lymphocyte Cultures for Use in Adoptive Transfer Therapy for Melanoma Patients", *Journal of Immunotherapy,* 26:332-342 (2003).

European Patent Office, International Search Report and Written Opinion issued in the International Patent Application No. PCT/US2021/048786, mailed on Mar. 3, 2022.

Haga-Friedman et al., "Incorporation of Transmembrane Hydrophobic Mutations in the TCR Enhance Its Surface Expression and T Cell Functional Avidity", *Journal of Immunology,* 188(11): 5538-5546 (2012).

Malekzadeh et al., "Neoantigen screening identifies broad TP53 mutant immunogenicity in patients with epithelial cancers", *Journal of Clinical Investigation,* 129(3): 1109-1114 (2019).

Parrales et al., "Targeting Oncogenic Mutant p53 for Cancer Therapy" *Frontiers in Oncology,* 5(288): 1-13 (2015).

Riddell et al., "The use of anti-CD3 and anti-CD28 monoclonal antibodies to clone and expand human antigen-specific T cells", *Journal of Immunological Methods,* 128: 189-201 (1990).

(Continued)

*Primary Examiner* — Michail A Belyavskyi

(74) *Attorney, Agent, or Firm* — Leydig, Voit & Mayer

(57) ABSTRACT

Disclosed are isolated or purified T cell receptors (TCRs) having antigenic specificity for human $p53^{R273C}$ or human $p53^{Y220C}$. Related polypeptides and proteins, as well as related nucleic acids, recombinant expression vectors, host cells, populations of cells, and pharmaceutical compositions are also provided. Also disclosed are methods of detecting the presence of cancer in a mammal and methods of treating or preventing cancer in a mammal.

16 Claims, 14 Drawing Sheets

Specification includes a Sequence Listing.

(56) References Cited

OTHER PUBLICATIONS

Sachs et al., "Impact of Cysteine Residues on MHC Binding Predictions and Recognition by Tumor-Reactive T Cells", *Journal of Immunology,* 205(2): 539-549 (2020).
Szymczak et al., "Correction of multi-gene deficiency in vivo using a single 'self-cleaving' 2A peptide-based retroviral vector", Nature Biotechnology, 22(5): 589-594 (2004).
Wu et al., "Structural basis of oligoclonal T cell recognition of a shared p53 cancer neoantigen", *Nature Communications,* 11(2908): 1-12 (2020).
Zhao et al., "Molecularly Targeted Therapies for p53-mutant Cancers", *Cellular and Molecular Life Sciences,* 74(22): 4171-4187 (2017).

TCR against p53 Y220C

TCR-F

TCRs against p53 R273C

TCRs against p53 R273C

TCR-O

TCRs against p53 R273C

```
CLUSTAL O(1.2.4) multiple sequence alignment

SP|P04637|P53_HUMAN     MEEPQSDPSVEPPLSQETFSDLWKLLPENNVLSPLPSQAMDDLMLSPDDIEQWFTEDPGP 60
SP|P04637-2|P53_HUMAN   MEEPQSDPSVEPPLSQETFSDLWKLLPENNVLSPLPSQAMDDLMLSPDDIEQWFTEDPGP 60
SP|P04637-3|P53_HUMAN   MEEPQSDPSVEPPLSQETFSDLWKLLPENNVLSPLPSQAMDDLMLSPDDIEQWFTEDPGP 60
SP|P04637-4|P53_HUMAN   ---------------------------------------MDDLMLSPDDIEQWFTEDPGP 21
SP|P04637-5|P53_HUMAN   ---------------------------------------MDDLMLSPDDIEQWFTEDPGP 21
SP|P04637-6|P53_HUMAN   ---------------------------------------MDDLMLSPDDIEQWFTEDPGP 21
SP|P04637-7|P53_HUMAN   ------------------------------------------------------------
SP|P04637-8|P53_HUMAN   ------------------------------------------------------------
SP|P04637-9|P53_HUMAN   ------------------------------------------------------------

SP|P04637|P53_HUMAN     DEAPRMPEAAPPVAPAPAAPTPAAPAPAPSWPLSSSVPSQKTYQGSYGFRLGFLHSGTAK 120
SP|P04637-2|P53_HUMAN   DEAPRMPEAAPPVAPAPAAPTPAAPAPAPSWPLSSSVPSQKTYQGSYGFRLGFLHSGTAK 120
SP|P04637-3|P53_HUMAN   DEAPRMPEAAPPVAPAPAAPTPAAPAPAPSWPLSSSVPSQKTYQGSYGFRLGFLHSGTAK 120
SP|P04637-4|P53_HUMAN   DEAPRMPEAAPPVAPAPAAPTPAAPAPAPSWPLSSSVPSQKTYQGSYGFRLGFLHSGTAK 81
SP|P04637-5|P53_HUMAN   DEAPRMPEAAPPVAPAPAAPTPAAPAPAPSWPLSSSVPSQKTYQGSYGFRLGFLHSGTAK 81
SP|P04637-6|P53_HUMAN   DEAPRMPEAAPPVAPAPAAPTPAAPAPAPSWPLSSSVPSQKTYQGSYGFRLGFLHSGTAK 81
SP|P04637-7|P53_HUMAN   ------------------------------------------------------------
SP|P04637-8|P53_HUMAN   ------------------------------------------------------------
SP|P04637-9|P53_HUMAN   ------------------------------------------------------------

SP|P04637|P53_HUMAN     SVTCTYSPALNKMFCQLAKTCPVQLWVDSTPPPGTRVRAMAIYKQSQHMTEVVRRCPHHE 180
SP|P04637-2|P53_HUMAN   SVTCTYSPALNKMFCQLAKTCPVQLWVDSTPPPGTRVRAMAIYKQSQHMTEVVRRCPHHE 180
SP|P04637-3|P53_HUMAN   SVTCTYSPALNKMFCQLAKTCPVQLWVDSTPPPGTRVRAMAIYKQSQHMTEVVRRCPHHE 180
SP|P04637-4|P53_HUMAN   SVTCTYSPALNKMFCQLAKTCPVQLWVDSTPPPGTRVRAMAIYKQSQHMTEVVRRCPHHE 141
SP|P04637-5|P53_HUMAN   SVTCTYSPALNKMFCQLAKTCPVQLWVDSTPPPGTRVRAMAIYKQSQHMTEVVRRCPHHE 141
SP|P04637-6|P53_HUMAN   SVTCTYSPALNKMFCQLAKTCPVQLWVDSTPPPGTRVRAMAIYKQSQHMTEVVRRCPHHE 141
SP|P04637-7|P53_HUMAN   ------------MFCQLAKTCPVQLWVDSTPPPGTRVRAMAIYKQSQHMTEVVRRCPHHE 48
SP|P04637-8|P53_HUMAN   ------------MFCQLAKTCPVQLWVDSTPPPGTRVRAMAIYKQSQHMTEVVRRCPHHE 48
SP|P04637-9|P53_HUMAN   ------------MFCQLAKTCPVQLWVDSTPPPGTRVRAMAIYKQSQHMTEVVRRCPHHE 48
                                    ************************************************

SP|P04637|P53_HUMAN     RCSDSDGLAPPQHLIRVEGNLRVEYLDDRNTFRHSVVVPYEPPEVGSDCTTIHYNYMCNS 240
SP|P04637-2|P53_HUMAN   RCSDSDGLAPPQHLIRVEGNLRVEYLDDRNTFRHSVVVPYEPPEVGSDCTTIHYNYMCNS 240
SP|P04637-3|P53_HUMAN   RCSDSDGLAPPQHLIRVEGNLRVEYLDDRNTFRHSVVVPYEPPEVGSDCTTIHYNYMCNS 240
SP|P04637-4|P53_HUMAN   RCSDSDGLAPPQHLIRVEGNLRVEYLDDRNTFRHSVVVPYEPPEVGSDCTTIHYNYMCNS 201
SP|P04637-5|P53_HUMAN   RCSDSDGLAPPQHLIRVEGNLRVEYLDDRNTFRHSVVVPYEPPEVGSDCTTIHYNYMCNS 201
SP|P04637-6|P53_HUMAN   RCSDSDGLAPPQHLIRVEGNLRVEYLDDRNTFRHSVVVPYEPPEVGSDCTTIHYNYMCNS 201
SP|P04637-7|P53_HUMAN   RCSDSDGLAPPQHLIRVEGNLRVEYLDDRNTFRHSVVVPYEPPEVGSDCTTIHYNYMCNS 108
SP|P04637-8|P53_HUMAN   RCSDSDGLAPPQHLIRVEGNLRVEYLDDRNTFRHSVVVPYEPPEVGSDCTTIHYNYMCNS 108
SP|P04637-9|P53_HUMAN   RCSDSDGLAPPQHLIRVEGNLRVEYLDDRNTFRHSVVVPYEPPEVGSDCTTIHYNYMCNS 108
                        ************************************************************

SP|P04637|P53_HUMAN     SCMGGMNRRPILTIITLEDSSGNLLGRNSFEVRVCACPGRDRRTEEENLRKKGEPHHELP 300
SP|P04637-2|P53_HUMAN   SCMGGMNRRPILTIITLEDSSGNLLGRNSFEVRVCACPGRDRRTEEENLRKKGEPHHELP 300
SP|P04637-3|P53_HUMAN   SCMGGMNRRPILTIITLEDSSGNLLGRNSFEVRVCACPGRDRRTEEENLRKKGEPHHELP 300
SP|P04637-4|P53_HUMAN   SCMGGMNRRPILTIITLEDSSGNLLGRNSFEVRVCACPGRDRRTEEENLRKKGEPHHELP 261
SP|P04637-5|P53_HUMAN   SCMGGMNRRPILTIITLEDSSGNLLGRNSFEVRVCACPGRDRRTEEENLRKKGEPHHELP 261
SP|P04637-6|P53_HUMAN   SCMGGMNRRPILTIITLEDSSGNLLGRNSFEVRVCACPGRDRRTEEENLRKKGEPHHELP 261
SP|P04637-7|P53_HUMAN   SCMGGMNRRPILTIITLEDSSGNLLGRNSFEVRVCACPGRDRRTEEENLRKKGEPHHELP 168
SP|P04637-8|P53_HUMAN   SCMGGMNRRPILTIITLEDSSGNLLGRNSFEVRVCACPGRDRRTEEENLRKKGEPHHELP 168
SP|P04637-9|P53_HUMAN   SCMGGMNRRPILTIITLEDSSGNLLGRNSFEVRVCACPGRDRRTEEENLRKKGEPHHELP 168
                        ************************************************************

SP|P04637|P53_HUMAN     PGSTKRALPNNTSSSPQPKKKPLDGEYFTLQIRGRERFEMFRELNEALELKDAQAGKEPG 360
SP|P04637-2|P53_HUMAN   PGSTKRALPNNTSSSPQPKKKPLDGEYFTLQDQTSFQKENC------------------- 341
SP|P04637-3|P53_HUMAN   PGSTKRALPNNTSSSPQPKKKPLDGEYFTLQMLLDLRWCYFLINSS-------------- 346
SP|P04637-4|P53_HUMAN   PGSTKRALPNNTSSSPQPKKKPLDGEYFTLQIRGRERFEMFRELNEALELKDAQAGKEPG 321
SP|P04637-5|P53_HUMAN   PGSTKRALPNNTSSSPQPKKKPLDGEYFTLQDQTSFQKENC------------------- 302
SP|P04637-6|P53_HUMAN   PGSTKRALPNNTSSSPQPKKKPLDGEYFTLQMLLDLRWCYFLINSS-------------- 307
SP|P04637-7|P53_HUMAN   PGSTKRALPNNTSSSPQPKKKPLDGEYFTLQIRGRERFEMFRELNEALELKDAQAGKEPG 228
SP|P04637-8|P53_HUMAN   PGSTKRALPNNTSSSPQPKKKPLDGEYFTLQDQTSFQKENC------------------- 209
SP|P04637-9|P53_HUMAN   PGSTKRALPNNTSSSPQPKKKPLDGEYFTLQMLLDLRWCYFLINSS-------------- 214
                        *******************************     :

SP|P04637|P53_HUMAN     GSRAHSSHLKSKKGQSTSRHKKLMFKTEGPDSD 393
SP|P04637-2|P53_HUMAN   ---------------------------------
SP|P04637-3|P53_HUMAN   ---------------------------------
SP|P04637-4|P53_HUMAN   GSRAHSSHLKSKKGQSTSRHKKLMFKTEGPDSD 354
SP|P04637-5|P53_HUMAN   ---------------------------------
SP|P04637-6|P53_HUMAN   ---------------------------------
SP|P04637-7|P53_HUMAN   GSRAHSSHLKSKKGQSTSRHKKLMFKTEGPDSD 261
SP|P04637-8|P53_HUMAN   ---------------------------------
SP|P04637-9|P53_HUMAN   ---------------------------------
```

FIG. 4

T CELL RECEPTORS RECOGNIZING R273C OR Y220C MUTATIONS IN P53

CROSS REFERENCE TO RELATED APPLICATIONS

This application is the U.S. national stage of International Patent Application No. PCT/US2021/048786, filed Sep. 2, 2021, which claims priority from U.S. Provisional Patent Application No. 63/074,747, filed on Sep. 4, 2020, each of which is incorporated herein by reference in its entirety.

STATEMENT REGARDING FEDERALLY SPONSORED RESEARCH OR DEVELOPMENT

This invention was made with Government support under project number BC010985 awarded by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 222,063 Byte ASCII (Text) file named "765229_ST25.txt," dated Feb. 21, 2023.

BACKGROUND OF THE INVENTION

Some cancers may have very limited treatment options, particularly when the cancer becomes metastatic and unresectable. Despite advances in treatments such as, for example, surgery, chemotherapy, and radiation therapy, the prognosis for many cancers, such as, for example, pancreatic, colorectal, lung, endometrial, ovarian, and prostate cancers, may be poor. Accordingly, there exists an unmet need for additional treatments for cancer.

BRIEF SUMMARY OF THE INVENTION

An embodiment of the invention provides an isolated or purified T cell receptor (TCR) having antigenic specificity for a human $p53^{R273C}$ or human $p53^{Y220C}$ amino acid sequence, wherein the TCR comprises the amino acid sequences of (1) all of SEQ ID NOs: 2-7; (2) all of SEQ ID NOs: 21-26; (3) all of SEQ ID NOs: 40-45; (4) all of SEQ ID NOs: 59-64; or (5) all of SEQ ID NOs: 78-83.

Further embodiments of the invention provide polypeptides, proteins, nucleic acids, recombinant expression vectors, host cells, populations of cells, and pharmaceutical compositions relating to the TCRs of the invention.

Still further embodiments of the invention provide methods of detecting the presence of cancer in a mammal, methods of inducing an immune response against a cancer in a mammal, and methods of treating or preventing cancer in a mammal.

Additional embodiments of the invention provide methods of producing a host cell expressing the TCR and methods of producing the TCR, polypeptide, or protein.

BRIEF DESCRIPTION OF THE SEVERAL VIEWS OF THE DRAWINGS

FIG. 4 shows an alignment of the amino acid sequences of the nine p53 splice variants. SP|P04637|P53_HUMAN (SEQ ID NO: 1); SP|P04637-2|P53_HUMAN (SEQ ID NO: 101); SP|P04637-3|P53_HUMAN (SEQ ID NO: 102); SP|P04637-4|P53_HUMAN (SEQ ID NO: 103); SP|P04637-5|P53_HUMAN (SEQ ID NO: 104);

Figure 1A:
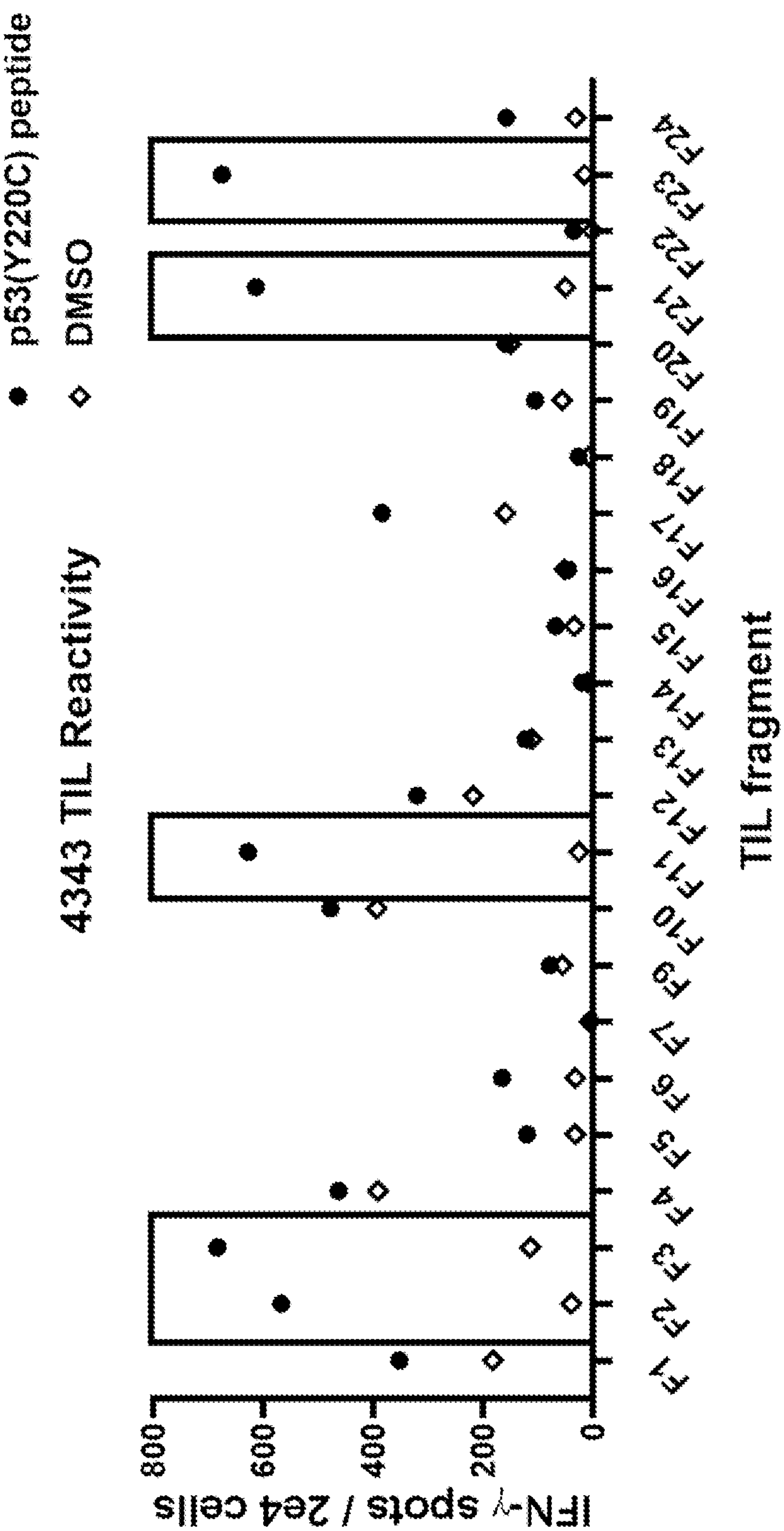
FIG. 1A is a graph showing the number of IFN-γ spots (per 2e4 cells) measured following co-culture of Patient 4343 tumor fragment numbers F1-F7 and F9-F24 with autologous DCs pulsed with DMSO (vehicle) or mutant p53-Y220C (FIG. 1A). Fragments with mutant p53 reactivity are boxed.

SP|P04637-6|P53_HUMAN (SEQ ID NO: 105); SP|P04637-7|P53_HUMAN (SEQ ID NO: 106); SP|P04637-8|P53_HUMAN (SEQ ID NO: 107); and SP|P04637-9|P53_HUMAN (SEQ ID NO: 108).

DETAILED DESCRIPTION OF THE INVENTION

Tumor Protein P53 (also referred to as "TP53" or "p53") acts as a tumor suppressor by, for example, regulating cell division. The p53 protein is located in the nucleus of the cell, where it binds directly to DNA. When DNA becomes damaged, the p53 protein is involved in determining whether the DNA will be repaired, or the damaged cell will undergo apoptosis. If the DNA can be repaired, p53 activates other genes to fix the damage. If the DNA cannot be repaired, the p53 protein prevents the cell from dividing and signals it to undergo apoptosis. By stopping cells with mutated or damaged DNA from dividing, p53 helps prevent the development of tumors. WT (normal) full-length p53 comprises the amino acid sequence of SEQ ID NO: 1.

Mutations in the p53 protein may reduce or eliminate the p53 protein's tumor suppressor function. Alternatively, or additionally, a p53 mutation may be a gain-of-function mutation by interfering with WT p53 in a dominant negative fashion. Mutated p53 protein may be expressed in any of a variety of human cancers such as, for example, cholangiocarcinoma, melanoma, colon cancer, rectal cancer, ovarian cancer, endometrial cancer, non-small cell lung cancer (NSCLC), glioblastoma, uterine cervical cancer, head and neck cancer, breast cancer, pancreatic cancer, or bladder cancer.

An embodiment of the invention provides an isolated or purified T cell receptor (TCR) having antigenic specificity for mutated human $p53^{R273C}$ or human $p53^{Y220C}$ amino acid sequence (hereinafter, "mutated p53"). Hereinafter, references to a "TCR" also refer to functional portions and functional variants of the TCR, unless specified otherwise. Mutations of p53 are defined herein by reference to the amino acid sequence of full-length, WT p53 (SEQ ID NO: 1). Mutations of p53 are described herein by reference to the amino acid residue present at a particular position, followed by the position number, followed by the amino acid with which that residue has been replaced in the particular mutation under discussion. A p53 amino acid sequence (e.g., a p53 peptide) may comprise fewer than all of the amino acid residues of the full-length, WT p53 protein. Accordingly, the position numbers are defined herein by reference to the WT full-length p53 protein (namely, SEQ ID NO: 1) with the understanding that the actual position of the corresponding residue in a particular example of a p53 amino acid sequence may be different. Because the positions are as defined by SEQ ID NO: 1, the term "R273C" indicates that the arginine present at position 273 of SEQ ID NO: 1 is replaced by cysteine, while "Y220C" indicates that the tyrosine present at position 220 of SEQ ID NO: 1 has been replaced with cysteine. For example, when a particular example of a p53 amino acid sequence is, e.g., SGNLLGRNSFEVRVCACPGRDRRTE (SEQ ID NO: 116) (an exemplary WT p53 peptide corresponding to contiguous amino acid residues 261 to 285 of SEQ ID NO: 1), "R273C" refers to a substitution of the underlined arginine in SEQ ID NO: 116 with cysteine, even though the actual position of the underlined arginine in SEQ ID NO: 116 is 13. Human p53 amino acid sequences with the R273C mutation are hereinafter referred to as "R273C" or "$p53^{R273C}$." Human p53 amino acid sequences with the Y220C mutation are hereinafter referred to as "Y220C" or "$p53^{Y220C}$." As used herein, "mutated p53" refers to human $p53^{R273C}$ or human $p53^{Y220C}$.

P53 has nine known splice variants. The p53 mutations described herein are conserved over all nine p53 splice variants. An alignment of the nine p53 splice variants is shown in FIG. 4. Accordingly, the inventive TCRs may have antigenic specificity for any mutated p53 amino acid sequence described herein encoded by any of the nine p53 splice variants. Because the positions are as defined by SEQ ID NO: 1, the actual positions of the amino acid sequence of a particular splice variant of p53 are defined relative to the corresponding positions of SEQ ID NO: 1, and the positions as defined by SEQ ID NO: 1 may be different than the actual positions in a particular splice variant. Thus, for example, mutations refer to a replacement of an amino acid residue in the amino acid sequence of a particular splice variant of p53 corresponding to the indicated position of the 393-amino acid sequence of SEQ ID NO: 1 with the understanding that the actual positions in the splice variant may be different.

In an embodiment of the invention, the TCR has antigenic specificity for human p53 with a mutation at position 273, as defined by SEQ ID NO: 1. The p53 mutation at position 273 may be any missense mutation. Accordingly, the mutation at position 273 may be a substitution of the native (WT) arginine residue present at position 273 with any amino acid residue other than arginine. In an embodiment of the invention, the TCR has antigenic specificity for a human $p53^{R273C}$ amino acid sequence. For example, the TCR may have antigenic specificity for the human $p53^{R273C}$ amino acid sequence of SGNLLGRNSFEVCVCACPGRDRRTE (SEQ ID NO: 117). In an embodiment of the invention, the TCR does not have antigenic specificity for the wild-type human p53 amino acid sequence of SGNLLGRNSFEVRVCACPGRDRRTE (SEQ ID NO: 116).

In an embodiment of the invention, the TCR has antigenic specificity for human p53 with a mutation at position 220, as defined by SEQ ID NO: 1. The p53 mutation at position 220 may be any missense mutation. Accordingly, the mutation at position 220 may be a substitution of the native (WT) tyrosine residue present at position 220 with any amino acid residue other than tyrosine. In an embodiment of the invention, the TCR has antigenic specificity for a human $p53^{Y220C}$ amino acid sequence. For example, the TCR may have antigenic specificity for the human $p53^{Y220C}$ amino acid sequence of DRNTFRHSVVVPCEPPEVGSDCTTI (SEQ ID NO: 115). In an embodiment of the invention, the TCR does not have antigenic specificity for the wild-type human p53 amino acid sequence of DRNTFRHSVVVPYEPPEVGSDCTTI (SEQ ID NO: 114).

In an embodiment of the invention, the inventive TCRs may be able to recognize mutated p53 in an HLA (human leukocyte antigen)-molecule-dependent manner. "HLA-molecule-dependent manner," as used herein, means that the TCR elicits an immune response upon binding to mutated p53 within the context of an HLA molecule, which HLA molecule is expressed by the patient from which the TCR was isolated. The inventive TCRs may be able to recognize mutated p53 that is presented by the applicable HLA molecule and may bind to the HLA molecule in addition to mutated p53.

In an embodiment of the invention, the inventive TCRs are able to recognize R273C presented by an HLA Class II molecule. In this regard, the TCR may elicit an immune response upon binding to R273C within the context of an HLA Class II molecule. The inventive TCRs are able to recognize R273C that is presented by an HLA Class II molecule and may bind to the HLA Class II molecule in addition to R273C.

In an embodiment of the invention, the HLA Class II molecule is an HLA-DP molecule. The HLA-DP molecule is a heterodimer of an α chain (DPA) and β chain (DPB). The HLA-DPA chain may be any HLA-DPA chain. The HLA-DPB chain may be any HLA-DPB chain. In an embodiment of the invention, the HLA Class II molecule is a heterodimer of an HLA-DPA1 chain and an HLA-DPB1 chain. Examples of HLA-DPA1 molecules may include, but are not limited to, those encoded by the HLA-DPA1*01:03, HLA-DPA1*01:04, HLA-DPA1*01:05, HLA-DPA1*01:06, HLA-DPA1*01:07, HLA-DPA1*01:08, HLA-DPA1*01:09, HLA-DPA1*01:10, HLA-DPA1*02:01, HLA-DPA1*02:02, HLA-DPA1*02:03, HLA-DPA1*02:04, HLA-DPA1*03:01, HLA-DPA1*03:02, HLA-DPA1*03:03, and HLA-DPA1*04:01 alleles. Examples of HLA-DPB1 molecules may include, but are not limited to, those encoded by the HLA-DPB1*01:01, HLA-DPB1*02:01, HLA-DPB1*02:02, HLA-DPB1*03:01, HLA-DPB1*04:01, HLA-DPB1*04:02, HLA-DPB1*05:01, HLA-DPB1*06:01, HLA-DPB1*07:01, HLA-DPB1*08:01, HLA-DPB1*09:01, and HLA-DPB1*10:01 alleles. Preferably, the HLA Class II molecule is a heterodimer of an HLA-DPA1*01:03 chain and an HLA-DPB1*04:02 chain.

In an embodiment of the invention, one of the inventive TCRs is able to recognize Y220C presented by an HLA Class II molecule. In this regard, the TCR may elicit an immune response upon binding to Y220C within the context of an HLA Class II molecule. The inventive TCR is able to recognize Y220C that is presented by an HLA Class II molecule and may bind to the HLA Class II molecule in addition to Y220C.

In an embodiment of the invention, the HLA Class II molecule is an HLA-DR heterodimer. The HLA-DR heterodimer is a cell surface receptor including an α chain and a β chain. The HLA-DR α chain is encoded by the HLA-DRA gene. In an embodiment, the alpha chain of the HLA Class II molecule is expressed by the HLA-DRA1*01:01:01 allele. The HLA-DR β chain is encoded by the HLA-DRB1 gene, the HLA-DRB3 gene, HLA-DRB4 gene, or the HLA-DRB5 gene. Examples of molecules encoded by the HLA-DRB1 gene may include, but are not limited to, HLA-DR1, HLA-DR2, HLA-DR3, HLA-DR4, HLA-DR5, HLA-DR6, HLA-DR7, HLA-DR8, HLA-DR9, HLA-DR10, HLA-DR11, HLA-DR12, HLA-DR13, HLA-DR14, HLA-DR15, HLA-DR16, and HLA-DR17. The HLA-DRB3 gene encodes HLA-DR52. The HLA-DRB4 gene encodes HLA-DR53. The HLA-DRB5 gene encodes HLA-DR51. In an embodiment of the invention, the HLA Class II molecule is an HLA-DRB3:HLA-DRA heterodimer. The beta chain of the HLA Class II molecule may be expressed by the HLA-DRB3*01:01, HLA-DRB3*02:02, or HLA-DRB3*03:01 allele. Preferably, the beta chain of the HLA Class II molecule is expressed by the HLA-DRB3*02:02:01 allele. In a preferred embodiment, the HLA Class II molecule is a heterodimer of an HLA-DRA1*01:01:01 chain and an HLA-DRB3*02:02:01 chain.

The TCRs of the invention may provide any one or more of many advantages, including when expressed by cells used for adoptive cell transfer. Mutated p53 is expressed by cancer cells and is not expressed by normal, noncancerous cells. Without being bound to a particular theory or mechanism, it is believed that the inventive TCRs advantageously target the destruction of cancer cells while minimizing or eliminating the destruction of normal, non-cancerous cells, thereby reducing, for example, by minimizing or eliminating, toxicity. Moreover, the inventive TCRs may, advantageously, successfully treat or prevent mutated p53-positive cancers that do not respond to other types of treatment such as, for example, chemotherapy, surgery, or radiation. Additionally, the inventive TCRs may provide highly avid recognition of mutated p53, which may provide the ability to recognize unmanipulated tumor cells (e.g., tumor cells that have not been treated with interferon (IFN)-γ, transfected with a vector encoding one or both of mutated p53 and the applicable HLA molecule, pulsed with a p53 peptide with the p53 mutation, or a combination thereof). Roughly half of all tumors harbor a mutation in p53, about half of which will be a missense mutation. The R273C mutation is expressed by about 2.8% of all cancers, and the HLA-DPB1*04:02 allele is expressed by about 24% of the U.S. Caucasian population and about 60% to about 80% of the U.S. Hispanic population. The Y220C mutation occurs in about 1.5% of all cancers, and the HLA-DRB3*02:02 allele is expressed by about 33% of the U.S. Caucasian population. The R273C and Y220C mutations arise in many cancer histologies, suggesting that a diverse group of patients could benefit from the inventive TCRs. Accordingly, the inventive TCRs may increase the number of patients who may be eligible for treatment with immunotherapy.

The phrase "antigenic specificity," as used herein, means that the TCR can specifically bind to and immunologically recognize mutated p53 with high avidity. For example, a TCR may be considered to have "antigenic specificity" for mutated p53 if about $1\times10^4$ to about $1\times10^5$ T cells expressing the TCR secrete at least about 200 pg/mL or more (e.g., 200 pg/mL or more, 300 pg/mL or more, 400 pg/mL or more, 500 pg/mL or more, 600 pg/mL or more, 700 pg/mL or more, 1,000 pg/mL or more, 5,000 pg/mL or more, 7,000 pg/mL or more, 10,000 pg/mL or more, 20,000 pg/mL or more, or a range defined by any two of the foregoing values) of IFN-γ upon co-culture with (a) antigen-negative, applicable HLA molecule positive target cells pulsed with a low concentration of mutated p53 peptide (e.g., about 0.05 ng/mL to about 5 ng/mL, 0.05 ng/mL, 0.1 ng/mL, 0.5 ng/mL, 1 ng/mL, 5 ng/mL, or a range defined by any two of the foregoing values) or (b) antigen-negative, applicable HLA molecule positive target cells into which a nucleotide sequence encoding mutated p53 has been introduced such that the target cell expresses mutated p53. Cells expressing the inventive TCRs may also secrete IFN-γ upon co-culture with antigen-negative, applicable HLA molecule positive target cells pulsed with higher concentrations of mutated p53 peptide.

Alternatively or additionally, a TCR may be considered to have "antigenic specificity" for mutated p53 if T cells expressing the TCR secrete at least twice as much IFN-γ upon co-culture with (a) antigen-negative, applicable HLA molecule positive target cells pulsed with a low concentration of mutated p53 peptide or (b) antigen-negative, applicable HLA molecule positive target cells into which a nucleotide sequence encoding mutated p53 has been introduced such that the target cell expresses mutated p53 as compared to the amount of IFN-γ expressed by a negative control. The negative control may be, for example, (i) T cells expressing the TCR, co-cultured with (a) antigen-negative, applicable HLA molecule positive target cells pulsed with the same concentration of an irrelevant peptide (e.g., some other peptide with a different sequence from the mutated p53 peptide) or (b) antigen-negative, applicable HLA molecule positive target cells into which a nucleotide sequence encoding an irrelevant peptide has been introduced such that the target cell expresses the irrelevant peptide, or (ii) untransduced T cells (e.g., derived from PBMC, which do not express the TCR) co-cultured with (a) antigen-negative, applicable HLA molecule positive target cells pulsed with the same concentration of mutated p53 peptide or (b) antigen-negative, applicable HLA molecule positive target cells into which a nucleotide sequence encoding mutated p53 has been introduced such that the target cell expresses mutated p53. IFN-γ secretion may be measured by methods known in the art such as, for example, enzyme-linked immunosorbent assay (ELISA).

Alternatively or additionally, a TCR may be considered to have "antigenic specificity" for mutated p53 if at least twice as many of the numbers of T cells expressing the TCR secrete IFN-γ upon co-culture with (a) antigen-negative, applicable HLA molecule positive target cells pulsed with a low concentration of mutated p53 peptide or (b) antigen-negative, applicable HLA molecule positive target cells into which a nucleotide sequence encoding mutated p53 has been introduced such that the target cell expresses mutated p53 as compared to the numbers of negative control T cells that secrete IFN-γ. The concentration of peptide and the negative control may be as described herein with respect to other aspects of the invention. The numbers of cells secreting IFN-γ may be measured by methods known in the art such as, for example, enzyme-linked immunospot (ELISpot) assay.

Alternatively or additionally, a TCR may be considered to have "antigenic specificity" for mutated p53 if at least twice as many spots are detected by ELISpot for the T cells expressing the TCR upon co-culture with (a) antigen-negative, applicable HLA molecule positive target cells pulsed with a low concentration of mutated p53 peptide or (b) antigen-negative, applicable HLA molecule positive target cells into which a nucleotide sequence encoding mutated p53 has been introduced such that the target cell expresses mutated p53 as compared to the number of spots detected by ELISpot for negative control T cells co-cultured with the same target cells. The concentration of peptide and the negative control may be as described herein with respect to other aspects of the invention.

Alternatively or additionally, a TCR may be considered to have "antigenic specificity" for mutated p53 if greater than about 50 spots are detected by ELISpot for the T cells expressing the TCR upon co-culture with (a) antigen-negative, applicable HLA molecule positive target cells pulsed with a low concentration of mutated p53 peptide or (b) antigen-negative, applicable HLA molecule positive target cells into which a nucleotide sequence encoding mutated p53 has been introduced such that the target cell expresses mutated p53. The concentration of peptide may be as described herein with respect to other aspects of the invention.

Alternatively, or additionally, a TCR may be considered to have "antigenic specificity" for mutated p53 if T cells expressing the TCR upregulate expression of one or both of 4-1BB and OX40 as measured by, for example, flow cytometry after stimulation with target cells expressing mutated p53.

An embodiment of the invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for mutated p53.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises a first polypeptide chain comprising an α chain CDR1 (CDR1α), an α chain CDR2 (CDR2α), and an α chain CDR3 (CDR3α), and a second polypeptide chain comprising a β chain CDR1 (CDR1β), a β chain CDR2 (CDR2β), and a β chain CDR3 (CDR3β). In an embodiment of the invention, the TCR comprises the amino acid sequences of: (1) all of SEQ ID NOs: 2-7; (2) all of SEQ ID NOs: 21-26; (3) all of SEQ ID NOs: 40-45; (4) all of SEQ ID NOs: 59-64; or (5) all of SEQ ID NOs: 78-83. Each one of the foregoing five collections of amino acid sequences in this paragraph sets forth the six CDR regions of each of five different TCRs having antigenic specificity for mutated human p53. The six amino acid sequences in each collection correspond to the CDR1α, CDR2α, CDR3α, CDR1β, CDR2β, and CDR3β of a TCR, respectively.

In an embodiment of the invention, the TCR comprises an α chain variable region amino acid sequence and a 1 chain variable region amino acid sequence, which together comprise one of the collections of CDRs set forth above. In this regard, the TCR can, e.g., comprise the amino acid sequence of any one of SEQ ID NOs: 8, 9, 10, 11, 12, 13, 27, 28, 29, 30, 31, 32, 46, 47, 48, 49, 50, 51, 65, 66, 67, 68, 69, 70, 84, 85, 86, 87, 88, 89, 119, 120, 121, 122, 123, 124, 125, 126, 127, 128, 129, 130, 131, 132, 133, 134, 135, 136, 137, and 138. For example, the TCR can comprise the amino acid sequences of (1) both of SEQ ID NOs: 8 and 9; (2) both of SEQ ID NOs: 10 and 11; (3) both of SEQ ID NOs: 12 and 13; (4) both of SEQ ID NOs: 12 and 11; (5) both of SEQ ID NOs: 121 and 13; (6) both of SEQ ID NOs: 121 and 122; (7) both of SEQ ID NOs: 8 and 120; (8) both of SEQ ID NOs: 119 and 9; (9) both of SEQ ID NOs: 119 and 120; (10) both of SEQ ID NOs: 27 and 28; (11) both of SEQ ID NOs: 29 and 30; (12) both of SEQ ID NOs: 31 and 32; (13) both of SEQ ID NOs: 31 and 30; (14) both of SEQ ID NOs: 125 and 32; (15) both of SEQ ID NOs: 125 and 126; (16) both of SEQ ID NOs: 27 and 124; (17) both of SEQ ID NOs: 123 and 28; (18) both of SEQ ID NOs: 123 and 124; (19) both of SEQ ID NOs: 46 and 47; (20) both of SEQ ID NOs: 48 and 49; (21) both of SEQ ID NOs: 50 and 51; (22) both of SEQ ID NOs: 50 and 49; (23) both of SEQ ID NOs: 129 and 51; (24) both of SEQ ID NOs: 129 and 130; (25) both of SEQ ID NOs: 46 and 128; (26) both of SEQ ID NOs: 127 and 47; (27) both of SEQ ID NOs: 127 and 128; (28) both of SEQ ID NOs: 65 and 66; (29) both of SEQ ID NOs: 67 and 68; (30) both of SEQ ID NOs: 69 and 70; (31) both of SEQ ID NOs: 69 and 68; (32) both of SEQ ID NOs: 133 and 70; (33) both of SEQ ID NOs: 133 and 134; (34) both of SEQ ID NOs: 65 and 132; (35) both of SEQ ID NOs: 131 and 66; (36) both of SEQ ID NOs: 131 and 132; (37) both of SEQ ID NOs: 84 and 85; (38) both of SEQ ID NOs: 86 and 87; (39) both of SEQ ID NOs: 88 and 89; (40) both of SEQ ID NOs: 88 and 87; (41) both of SEQ ID NOs: 137 and 89; (42) both of SEQ ID NOs: 137 and 138; (43) both of SEQ ID NOs: 84 and 136; (44) both of SEQ ID NOs: 135 and 85; or (45) both of SEQ ID NOs: 135 and 136. Each one of the foregoing collections of amino acid sequences in this paragraph sets forth the two variable regions of each of the different TCRs having antigenic specificity for mutated human p53. The two amino acid sequences in each collection correspond to the variable region of the α chain and the variable region of the β chain of a TCR, respectively.

The inventive TCRs may further comprise a constant region. The constant region may be derived from any suitable species such as, e.g., human or mouse. In an embodiment of the invention, the TCRs further comprise a murine constant region. As used herein, the term "murine" or "human," when referring to a TCR or any component of a TCR described herein (e.g., complementarity determining region (CDR), variable region, constant region, alpha chain, and/or beta chain), means a TCR (or component thereof) which is derived from a mouse or a human, respectively, i.e., a TCR (or component thereof) that originated from or was, at one time, expressed by a mouse T cell or a human T cell, respectively. In an embodiment of the invention, the TCR may comprise a murine α chain constant region and a murine β chain constant region. The murine α chain constant region may be modified or unmodified. A modified murine α chain constant region may be, e.g., cysteine-substituted, LVL-modified, or both cysteine-substituted and LVL-modified, as described, for example, in U.S. Pat. No. 10,174,098. The murine β chain constant region may be modified or unmodified. A modified murine β chain constant region may be, e.g., cysteine-substituted, as described, for example, in U.S. Pat. No. 10,174,098. In some embodiments of the invention, the TCR comprises a cysteine-substituted, LVL-modified murine α chain constant region comprising the amino acid sequence of SEQ ID NO: 97. In some embodiments of the invention, the TCR comprises a cysteine-substituted, LVL-modified murine α chain constant region comprising the amino acid sequence of SEQ ID NO: 98. In some embodiments of the invention, the TCR comprises a cysteine-substituted, LVL-modified murine α chain constant region comprising the amino acid sequence of SEQ ID NO: 143. In some embodiments of the invention, the TCR comprises an LVL-modified murine α chain constant region comprising the amino acid sequence of SEQ ID NO: 144. In some embodiments of the invention, the TCR comprises an LVL-modified murine α chain constant region comprising the amino acid sequence of SEQ ID NO: 145. In some embodiments of the invention, the TCR comprises an LVL-modified murine α chain constant region comprising the amino acid sequence of SEQ ID NO: 146. In some embodiments of the invention, the TCR comprises a cysteine-substituted murine α chain constant region comprising the amino acid sequence of SEQ ID NO: 147. In some embodiments of the invention, the TCR comprises a cysteine-substituted murine α chain constant region comprising the amino acid sequence of SEQ ID NO: 148. In some embodiments of the invention, the TCR comprises a cysteine-substituted murine α chain constant region comprising the amino acid sequence of SEQ ID NO: 149. In an embodiment of the invention, the TCR comprises a D1 murine α chain constant region comprising the amino acid sequence of SEQ ID NO: 139. In some embodiments of the invention, the TCR comprises a murine α chain constant region described in the degenerate amino acid sequence comprising the amino acid sequence of SEQ ID NO: 141. In an embodiment of the invention, the TCR comprises a cysteine-substituted murine β chain constant region comprising the amino acid sequence of SEQ ID NO: 99. In an embodiment of the invention, the TCR comprises a wild-type murine β chain constant region comprising the amino acid sequence of SEQ ID NO: 140. In some embodiments of the invention, the TCR comprises a murine β chain constant region described in the degenerate amino acid sequence comprising the amino acid sequence of SEQ ID NO: 142.

Exemplary Cα region sequences and Cβ region sequences are shown in Tables 1 and 2.

TABLE 1

Amino acid sequences of TCR Cα regions.

| Description | Sequence | SEQ ID NO: |
|---|---|---|
| Cα (D1 variant) | DIQNPEPAVYQLKDPRSQDSTLCLFTDFDSQINVPKTMESGTFITDKTVLDM<br>KAMDSKSNGAIAWSNQTSFTCQDIFKETNATYPSSDVPCDATLTEKSFETDM<br>NLNFQNLSVMGLRILLLKVAGFNLLMTLRLWSS | 139 |
| Cα (degenerate) | XIQNPEPAVYQLKDPRSQDSTLCLFTDFDSQINVPKTMESGTFITDKXVLDM<br>KAMDSKSNGAIAWSNQTSFTCQDIFKETNATYPSSDVPCDATLTEKSFETDM<br>NLNFQNLXVXXLRILLLKVAGFNLLMTLRLWSS<br>X at position 1 is Asn, Asp, His, or Tyr;<br>X at position 48 is Thr or Cys;<br>X at position 112 is Ser, Ala, Val,<br>Leu, Ile, Pro, Phe, Met, or Trp;<br>X at position 114 is Met, Ala, Val,<br>Leu, Ile, Pro, Phe, or Trp;<br>X at position 115 is Gly, Ala, Val,<br>Leu, Ile, Pro, Phe, Met, or Trp | 141 |
| Cα (cysteine- and LVL-modified, substituted w/X at amino acid 1) | XIQNPEPAVYQLKDPRSQDSTLCLFTDFDSQINVPKTMESGTFITDKCVLDM<br>KAMDSKSNGAIAWSNQTSFTCQDIFKETNATYPSSDVPCDATLTEKSFETDM<br>NLNFQNLLVIVLRILLLKVAGFNLLMTLRLWSS<br>X at position 1 is Asn, Asp, His, or Tyr | 143 |
| Cα (cysteine- and LVL-modified, substituted w/N at amino acid 1) | NIQNPEPAVYQLKDPRSQDSTLCLFTDFDSQINVPKTMESGTFITDKCVLDM<br>KAMDSKSNGAIAWSNQTSFTCQDIFKETNATYPSSDVPCDATLTEKSFETDM<br>NLNFQNLLVIVLRILLLKVAGFNLLMTLRLWSS | 97 |
| Cα (cysteine- and LVL-modified, substituted w/D at amino acid 1) | DIQNPEPAVYQLKDPRSQDSTLCLFTDFDSQINVPKTMESGTFITDKCVLDM<br>KAMDSKSNGAIAWSNQTSFTCQDIFKETNATYPSSDVPCDATLTEKSFETDM<br>NLNFQNLLVIVLRILLLKVAGFNLLMTLRLWSS | 98 |
| Cα (LVL-modified, w/X at amino acid 1) | XIQNPEPAVYQLKDPRSQDSTLCLFTDFDSQINVPKTMESGTFITDKTVLDM<br>KAMDSKSNGAIAWSNQTSFTCQDIFKETNATYPSSDVPCDATLTEKSFETDM | 144 |

TABLE 1-continued

Amino acid sequences of TCR Cα regions.

| Description | Sequence | SEQ ID NO: |
|---|---|---|
| | NLNFQNLLVIVLRILLLKVAGFNLLMTLRLWSS<br>X at position 1 is Asn, Asp, His, or Tyr | |
| Cα (LVL-modified w/N at amino acid 1) | NIQNPEPAVYQLKDPRSQDSTLCLFTDFDSQINVPKTMESGTFITDKTVLDM KAMDSKSNGAIAWSNQTSFTCQDIFKETNATYPSSDVPCDATLTEKSFETDM NLNFQNLLVIVLRILLLKVAGFNLLMTLRLWSS | 145 |
| Cα (LVL-modified, w/D at amino acid 1) | DIQNPEPAVYQLKDPRSQDSTLCLFTDFDSQINVPKTMESGTFITDKTVLDM KAMDSKSNGAIAWSNQTSFTCQDIFKETNATYPSSDVPCDATLTEKSFETDM NLNFQNLLVIVLRILLLKVAGFNLLMTLRLWSS | 146 |
| Cα (cysteine-substituted, w/X at amino acid 1) | XIQNPEPAVYQLKDPRSQDSTLCLFTDFDSQINVPKTMESGTFITDKCVLDM KAMDSKSNGAIAWSNQTSFTCQDIFKETNATYPSSDVPCDATLTEKSFETDM NLNFQNLSVMGLRILLLKVAGFNLLMTLRLWSS<br>X at position 1 is Asn, Asp, His, or Tyr | 147 |
| Cα (cysteine-substituted, w/N at amino acid 1) | NIQNPEPAVYQLKDPRSQDSTLCLFTDFDSQINVPKTMESGTFITDKCVLDM KAMDSKSNGAIAWSNQTSFTCQDIFKETNATYPSSDVPCDATLTEKSFETDM NLNFQNLSVMGLRILLLKVAGFNLLMTLRLWSS | 148 |
| Cα (cysteine-substituted, w/D at amino acid 1) | DIQNPEPAVYQLKDPRSQDSTLCLFTDFDSQINVPKTMESGTFITDKCVLDM KAMDSKSNGAIAWSNQTSFTCQDIFKETNATYPSSDVPCDATLTEKSFETDM NLNFQNLSVMGLRILLLKVAGFNLLMTLRLWSS | 149 |

TABLE 2

Amino acid sequences of TCR Cβ regions.

| Description | Sequence | SEQ ID NO: |
|---|---|---|
| Cβ (cysteine-substituted) | EDLRNVTPPKVSLFEPSKAEIANKQK ATLVCLARGFFPDHVELSWWVNGKEV HSGVCTDPQAYKESNYSYCLSSRLRV SATFWHNPRNHFRCQVQFHGLSEEDK WPEGSPKPVTQNISAEAWGRADCGIT SASYQQGVLSATILYEILLGKATLYA VLVSTLVVMAMVKRKNS | 99 |
| Cβ (wild-type) | EDLRNVTPPKVSLFEPSKAEIANKQK ATLVCLARGFFPDHVELSWWVNGKEV HSGVSTDPQAYKESNYSYCLSSRLRV SATFWHNPRNHFRCQVQFHGLSEEDK WPEGSPKPVTQNISAEAWGRADCGIT SASYQQGVLSATILYEILLGKATLYA VLVSTLVVMAMVKRKNS | 140 |
| Cβ (degenerate) | EDLRNVTPPKVSLFEPSKAEIANKQK ATLVCLARGFFPDHVELSWWVNGKEV HSGVXTDPQAYKESNYSYCLSSRLRV SATFWHNPRNHFRCQVQFHGLSEEDK WPEGSPKPVTQNISAEAWGRADCGIT SASYQQGVLSATILYEILLGKATLYA VLVSTLVVMAMVKRKNS<br>X at position 57 is Ser or Cys | 142 |

In an embodiment of the invention, the inventive TCR can comprise an α chain of a TCR and a β chain of a TCR. The α chain of the TCR may comprise a variable region of an α chain and a constant region of an α chain. An α chain of this type can be paired with any β chain of a TCR. The β chain may comprise a variable region of a β chain and a constant region of a β chain.

In some embodiments, the amino acid sequence of any of the α chains and/or β chains disclosed herein further comprises the amino acid sequence RAKR (SEQ ID NO: 118) at the C-terminal end.

In an embodiment of the invention, the TCR comprises the amino acid sequence of any one of SEQ ID NOs: 14, 15, 16, 17, 18, 19, 33, 34, 35, 36, 37, 38, 52, 53, 54, 55, 56, 57, 71, 72, 73, 74, 75, 76, 90, 91, 92, 93, 94, and 95. For example, the TCR can comprise the amino acid sequences of (1) both of SEQ ID NOs: 14 and 15; (2) both of SEQ ID NOs: 16 and 17; (3) both of SEQ ID NOs: 18 and 19; (4) both of SEQ ID NOs: 33 and 34; (5) both of SEQ ID NOs: 35 and 36; (6) both of SEQ ID NOs: 37 and 38; (7) both of SEQ ID NOs: 52 and 53; (8) both of SEQ ID NOs: 54 and 55; (9) both of SEQ ID NOs: 56 and 57; (10) both of SEQ ID NOs: 71 and 72; (11) both of SEQ ID NOs: 73 and 74; (12) both of SEQ ID NOs: 75 and 76; (13) both of SEQ ID NOs: 90 and 91; (14) both of SEQ ID NOs: 92 and 93; or (15) both of SEQ ID NOs: 94 and 95. Each one of the foregoing collections of amino acid sequences in this paragraph sets forth the α chain and β chain of each of different TCRs having antigenic specificity for mutated human p53. The two amino acid sequences in each collection correspond to the α chain and the β chain of a TCR, respectively.

Included in the scope of the invention are functional variants of the inventive TCRs described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to mutated p53 for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, at least about 50%, at least about 75%, at least about 80%, at least about 90%, at least about 95%, at least about 96%, at least about 97%, at least about 98%, at least about 99% or more identical in amino acid sequence to the parent TCR, polypeptide, or protein, respectively.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively, or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the TCR, polypeptide, or protein, e.g., other amino acids, do not materially change the biological activity of the TCR, polypeptide, or protein.

Also provided by the invention is a polypeptide comprising a functional portion of any of the TCRs described herein. The term "polypeptide," as used herein, includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to mutated p53. The term "functional portion," when used in reference to a TCR, refers to any part or fragment of the TCR of the invention, which part or fragment retains the biological activity of the TCR of which it is a part (the parent TCR). Functional portions encompass, for example, those parts of a TCR that retain the ability to specifically bind to mutated p53 (e.g., in an applicable HLA molecule-dependent manner), or detect, treat, or prevent cancer, to a similar extent, the same extent, or to a higher extent, as the parent TCR. In reference to the parent TCR, the functional portion can comprise, for instance, about 10%, about 25%, about 30%, about 50%, about 70%, about 80%, about 90%, about 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to mutated p53; and/or having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one or more of CDR1, CDR2, and CDR3 of the variable region(s) of the α chain and/or β chain of a TCR of the invention. In an embodiment of the invention, the polypeptide can comprise the amino acid sequences of: (1) all of SEQ ID NOs: 2-7; (2) all of SEQ ID NOs: 21-26; (3) all of SEQ ID NOs: 40-45; (4) all of SEQ ID NOs: 59-64; or (5) all of SEQ ID NOs: 78-83.

In an embodiment of the invention, the inventive polypeptide can comprise, for instance, the variable region of the inventive TCR comprising a combination of the CDR regions set forth above. In this regard, the polypeptide can comprise, e.g., the amino acid sequences of: (1) both of SEQ ID NOs: 8 and 9; (2) both of SEQ ID NOs: 10 and 11; (3) both of SEQ ID NOs: 12 and 13; (4) both of SEQ ID NOs: 12 and 11; (5) both of SEQ ID NOs: 121 and 13; (6) both of SEQ ID NOs: 121 and 122; (7) both of SEQ ID NOs: 8 and 120; (8) both of SEQ ID NOs: 119 and 9; (9) both of SEQ ID NOs: 119 and 120; (10) both of SEQ ID NOs: 27 and 28; (11) both of SEQ ID NOs: 29 and 30; (12) both of SEQ ID NOs: 31 and 32; (13) both of SEQ ID NOs: 31 and 30; (14) both of SEQ ID NOs: 125 and 32; (15) both of SEQ ID NOs: 125 and 126; (16) both of SEQ ID NOs: 27 and 124; (17) both of SEQ ID NOs: 123 and 28; (18) both of SEQ ID NOs: 123 and 124; (19) both of SEQ ID NOs: 46 and 47; (20) both of SEQ ID NOs: 48 and 49; (21) both of SEQ ID NOs: 50 and 51; (22) both of SEQ ID NOs: 50 and 49; (23) both of SEQ ID NOs: 129 and 51; (24) both of SEQ ID NOs: 129 and 130; (25) both of SEQ ID NOs: 46 and 128; (26) both of SEQ ID NOs: 127 and 47; (27) both of SEQ ID NOs: 127 and 128; (28) both of SEQ ID NOs: 65 and 66; (29) both of SEQ ID NOs: 67 and 68; (30) both of SEQ ID NOs: 69 and 70; (31) both of SEQ ID NOs: 69 and 68; (32) both of SEQ ID NOs: 133 and 70; (33) both of SEQ ID NOs: 133 and 134; (34) both of SEQ ID NOs: 65 and 132; (35) both of SEQ ID NOs: 131 and 66; (36) both of SEQ ID NOs: 131 and 132; (37) both of SEQ ID NOs: 84 and 85; (38) both of SEQ ID NOs: 86 and 87; (39) both of SEQ ID NOs: 88 and 89; (40) both of SEQ ID NOs: 88 and 87; (41) both of SEQ ID NOs: 137 and 89; (42) both of SEQ ID NOs: 137 and 138; (43) both of SEQ ID NOs: 84 and 136; (44) both of SEQ ID NOs: 135 and 85; or (45) both of SEQ ID NOs: 135 and 136.

In an embodiment of the invention, the inventive polypeptide can further comprise the constant region of the inventive TCR set forth above. In this regard, the polypeptide can comprise, e.g., the amino acid sequence of (i) one of SEQ ID NOs 97-99, and 139-149 or (ii) one of SEQ ID NOs: 99, 140, and 142 and one of SEQ ID NOs: 97, 98, 139, 141, and 143-149.

In an embodiment of the invention, the inventive polypeptide may comprise an α chain and a β chain of the inventive TCR. In this regard, the polypeptide can comprise, e.g., the amino acid sequences of (1) both of SEQ ID NOs: 14 and 15; (2) both of SEQ ID NOs: 16 and 17; (3) both of SEQ ID NOs: 18 and 19; (4) both of SEQ ID NOs: 33 and 34; (5) both of SEQ ID NOs: 35 and 36; (6) both of SEQ ID NOs: 37 and 38; (7) both of SEQ ID NOs: 52 and 53; (8) both of SEQ ID NOs: 54 and 55; (9) both of SEQ ID NOs: 56 and 57; (10) both of SEQ ID NOs: 71 and 72; (11) both of SEQ ID NOs: 73 and 74; (12) both of SEQ ID NOs: 75 and 76; (13) both of SEQ ID NOs: 90 and 91; (14) both of SEQ ID NOs: 92 and 93; or (15) both of SEQ ID NOs: 94 and 95.

An embodiment of the invention further provides a protein comprising at least one of the polypeptides described herein. By "protein" is meant a molecule comprising one or more polypeptide chains. In an embodiment, the protein of the invention can comprise: (1) a first polypeptide chain comprising the amino acid sequences of all of SEQ ID NOs: 2-4 and a second polypeptide chain comprising the amino acid sequences of all of SEQ ID NOs: 5-7; (2) a first polypeptide chain comprising the amino acid sequences of all of SEQ ID NOs: 21-23 and a second polypeptide chain comprising the amino acid sequences of all of SEQ ID NOs: 24-26; (3) a first polypeptide chain comprising the amino acid sequences of all of SEQ ID NOs: 40-42 and a second polypeptide chain comprising the amino acid sequences of all of SEQ ID NOs: 43-45; (4) a first polypeptide chain comprising the amino acid sequences of all of SEQ ID NOs: 59-61 and a second polypeptide chain comprising the amino acid sequences of all of SEQ ID NOs: 62-64; or (5) a first polypeptide chain comprising the amino acid sequences of all of SEQ ID NOs: 78-80 and a second polypeptide chain comprising the amino acid sequences of all of SEQ ID NOs: 81-83.

In an embodiment of the invention, the protein comprises: (1) a first polypeptide chain comprising the amino acid sequence of SEQ ID NO: 8 and a second polypeptide chain comprising the amino acid sequence of SEQ ID NO: 9; (2) a first polypeptide chain comprising the amino acid sequence of SEQ ID NO: 10 and a second polypeptide chain comprising the amino acid sequence of SEQ ID NO: 11; (3) a first polypeptide chain comprising the amino acid sequence of SEQ ID NO: 12 and a second polypeptide chain comprising the amino acid sequence of SEQ ID NO: 13; (4) a first polypeptide chain comprising the amino acid sequence of SEQ ID NO: 12 and a second polypeptide chain comprising the amino acid sequence of SEQ ID NO: 11; (5) a first polypeptide chain comprising the amino acid sequence of SEQ ID NO: 121 and a second polypeptide chain comprising the amino acid sequence of SEQ ID NO: 13; (6) a first polypeptide chain comprising the amino acid sequence of SEQ ID NO: 121 and a second polypeptide chain comprising the amino acid sequence of SEQ ID NO: 122; (7) a first polypeptide chain comprising the amino acid sequence of SEQ ID NO: 8 and a second polypeptide chain comprising the amino acid sequence of SEQ ID NO: 120; (8) a first polypeptide chain comprising the amino acid sequence of SEQ ID NO: 119 and a second polypeptide chain comprising the amino acid sequence of SEQ ID NO: 9; (9) a first polypeptide chain comprising the amino acid sequence of SEQ ID NO: 119 and a second polypeptide chain comprising the amino acid sequence of SEQ ID NO: 120; (10) a first polypeptide chain comprising the amino acid sequence of SEQ ID NO: 27 and a second polypeptide chain comprising the amino acid sequence of SEQ ID NO: 28; (11) a first polypeptide chain comprising the amino acid sequence of SEQ ID NO: 29 and a second polypeptide chain comprising the amino acid sequence of SEQ ID NO: 30; (12) a first polypeptide chain comprising the amino acid sequence of SEQ ID NO: 31 and a second polypeptide chain comprising the amino acid sequence of SEQ ID NO: 32; (13) a first polypeptide chain comprising the amino acid sequence of SEQ ID NO: 31 and a second polypeptide chain comprising the amino acid sequence of SEQ ID NO: 30; (14) a first polypeptide chain comprising the amino acid sequence of SEQ ID NO: 125 and a second polypeptide chain comprising the amino acid sequence of SEQ ID NO: 32; (15) a first polypeptide chain comprising the amino acid sequence of SEQ ID NO: 125 and a second polypeptide chain comprising the amino acid sequence of SEQ ID NO: 126; (16) a first polypeptide chain comprising the amino acid sequence of SEQ ID NO: 27 and a second polypeptide chain comprising the amino acid sequence of SEQ ID NO: 124; (17) a first polypeptide chain comprising the amino acid sequence of SEQ ID NO: 123 and a second polypeptide chain comprising the amino acid sequence of SEQ ID NO: 28; (18) a first polypeptide chain comprising the amino acid sequence of SEQ ID NO: 123 and a second polypeptide chain comprising the amino acid sequence of SEQ ID NO: 124; (19) a first polypeptide chain comprising the amino acid sequence of SEQ ID NO: 46 and a second polypeptide chain comprising the amino acid sequence of SEQ ID NO: 47; (20) a first polypeptide chain comprising the amino acid sequence of SEQ ID NO: 48 and a second polypeptide chain comprising the amino acid sequence of SEQ ID NO: 49; (21) a first polypeptide chain comprising the amino acid sequence of SEQ ID NO: 50 and a second polypeptide chain comprising the amino acid sequence of SEQ ID NO: 51; (22) a first polypeptide chain comprising the amino acid sequence of SEQ ID NO: 50 and a second polypeptide chain comprising the amino acid sequence of SEQ ID NO: 49; (23) a first polypeptide chain comprising the amino acid sequence of SEQ ID NO: 129 and a second polypeptide chain comprising the amino acid sequence of SEQ ID NO: 51; (24) a first polypeptide chain comprising the amino acid sequence of SEQ ID NO: 129 and a second polypeptide chain comprising the amino acid sequence of SEQ ID NO: 130; (25) a first polypeptide chain comprising the amino acid sequence of SEQ ID NO: 46 and a second polypeptide chain comprising the amino acid sequence of SEQ ID NO: 128; (26) a first polypeptide chain comprising the amino acid sequence of SEQ ID NO: 127 and a second polypeptide chain comprising the amino acid sequence of SEQ ID NO: 47; (27) a first polypeptide chain comprising the amino acid sequence of SEQ ID NO: 127 and a second polypeptide chain comprising the amino acid sequence of SEQ ID NO: 128; (28) a first polypeptide chain comprising the amino acid sequence of SEQ ID NO: 65 and a second polypeptide chain comprising the amino acid sequence of SEQ ID NO: 66; (29) a first polypeptide chain comprising the amino acid sequence of SEQ ID NO: 67 and a second polypeptide chain comprising the amino acid sequence of SEQ ID NO: 68; (30) a first polypeptide chain comprising the amino acid sequence of SEQ ID NO: 69 and a second polypeptide chain comprising the amino acid sequence of SEQ ID NO: 70; (31) a first polypeptide chain comprising the amino acid sequence of SEQ ID NO: 69 and a second polypeptide chain comprising the amino acid sequence of SEQ ID NO: 68; (32) a first polypeptide chain comprising the amino acid sequence of SEQ ID NO: 133 and a second polypeptide chain comprising the amino acid sequence of SEQ ID NO: 70; (33) a first polypeptide chain comprising the amino acid sequence of SEQ ID NO: 133 and a second polypeptide chain comprising the amino acid sequence of SEQ ID NO: 134; (34) a first polypeptide chain comprising the amino acid sequence of SEQ ID NO: 65 and a second polypeptide chain comprising the amino acid sequence of SEQ ID NO: 132; (35) a first polypeptide chain comprising the amino acid sequence of SEQ ID NO: 131 and a second polypeptide chain comprising the amino acid sequence of SEQ ID NO: 66; (36) a first polypeptide chain comprising the amino acid sequence of SEQ ID NO: 131 and a second polypeptide chain comprising the amino acid sequence of SEQ ID NO:

132; (37) a first polypeptide chain comprising the amino acid sequence of SEQ ID NO: 84 and a second polypeptide chain comprising the amino acid sequence of SEQ ID NO: 85; (38) a first polypeptide chain comprising the amino acid sequence of SEQ ID NO: 86 and a second polypeptide chain comprising the amino acid sequence of SEQ ID NO: 87; (39) a first polypeptide chain comprising the amino acid sequence of SEQ ID NO: 88 and a second polypeptide chain comprising the amino acid sequence of SEQ ID NO: 89; (40) a first polypeptide chain comprising the amino acid sequence of SEQ ID NO: 88 and a second polypeptide chain comprising the amino acid sequence of SEQ ID NO: 87; (41) a first polypeptide chain comprising the amino acid sequence of SEQ ID NO: 137 and a second polypeptide chain comprising the amino acid sequence of SEQ ID NO: 89; (42) a first polypeptide chain comprising the amino acid sequence of SEQ ID NO: 137 and a second polypeptide chain comprising the amino acid sequence of SEQ ID NO: 138; (43) a first polypeptide chain comprising the amino acid sequence of SEQ ID NO: 84 and a second polypeptide chain comprising the amino acid sequence of SEQ ID NO: 136; (44) a first polypeptide chain comprising the amino acid sequence of SEQ ID NO: 135 and a second polypeptide chain comprising the amino acid sequence of SEQ ID NO: 85; or (45) a first polypeptide chain comprising the amino acid sequence of SEQ ID NO: 135 and a second polypeptide chain comprising the amino acid sequence of SEQ ID NO: 136.

In an embodiment of the invention, the protein can further comprise the constant region of the inventive TCR set forth above. In this regard, the first polypeptide chain can comprise one of SEQ ID NOs: 99, 140, and 142 and the second polypeptide chain can comprise one of SEQ ID NOs: 97, 98, 139, 141, and 143-149.

In an embodiment of the invention, the protein comprises: (1) a first polypeptide chain comprising the amino acid sequence of SEQ ID NO: 14 and a second polypeptide chain comprising the amino acid sequence of SEQ ID NO: 15; (2) a first polypeptide chain comprising the amino acid sequence of SEQ ID NO: 16 and a second polypeptide chain comprising the amino acid sequence of SEQ ID NO: 17; (3) a first polypeptide chain comprising the amino acid sequence of SEQ ID NO: 18 and a second polypeptide chain comprising the amino acid sequence of SEQ ID NO: 19; (4) a first polypeptide chain comprising the amino acid sequence of SEQ ID NO: 33 and a second polypeptide chain comprising the amino acid sequence of SEQ ID NO: 34; (5) a first polypeptide chain comprising the amino acid sequence of SEQ ID NO: 35 and a second polypeptide chain comprising the amino acid sequence of SEQ ID NO: 36; (6) a first polypeptide chain comprising the amino acid sequence of SEQ ID NO: 37 and a second polypeptide chain comprising the amino acid sequence of SEQ ID NO: 38; (7) a first polypeptide chain comprising the amino acid sequence of SEQ ID NO: 52 and a second polypeptide chain comprising the amino acid sequence of SEQ ID NO: 53; (8) a first polypeptide chain comprising the amino acid sequence of SEQ ID NO: 54 and a second polypeptide chain comprising the amino acid sequence of SEQ ID NO: 55; (9) a first polypeptide chain comprising the amino acid sequence of SEQ ID NO: 56 and a second polypeptide chain comprising the amino acid sequence of SEQ ID NO: 57; (10) a first polypeptide chain comprising the amino acid sequence of SEQ ID NO: 71 and a second polypeptide chain comprising the amino acid sequence of SEQ ID NO: 72; (11) a first polypeptide chain comprising the amino acid sequence of SEQ ID NO: 73 and a second polypeptide chain comprising the amino acid sequence of SEQ ID NO: 74; (12) a first polypeptide chain comprising the amino acid sequence of SEQ ID NO: 75 and a second polypeptide chain comprising the amino acid sequence of SEQ ID NO: 76; (13) a first polypeptide chain comprising the amino acid sequence of SEQ ID NO: 90 and a second polypeptide chain comprising the amino acid sequence of SEQ ID NO: 91; (14) a first polypeptide chain comprising the amino acid sequence of SEQ ID NO: 92 and a second polypeptide chain comprising the amino acid sequence of SEQ ID NO: 93; or (15) a first polypeptide chain comprising the amino acid sequence of SEQ ID NO: 94 and a second polypeptide chain comprising the amino acid sequence of SEQ ID NO: 95.

The protein of the invention may be a TCR. Alternatively, if the first and/or second polypeptide chain(s) of the protein further comprise(s) other amino acid sequences, e.g., an amino acid sequence encoding an immunoglobulin or a portion thereof, then the inventive protein can be a fusion protein. In this regard, an embodiment of the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CDT molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs, polypeptides, and proteins of the invention may be expressed as a single protein comprising a linker peptide linking the α chain and the β chain. In this regard, the TCRs, polypeptides, and proteins of the invention may further comprise a linker peptide. The linker peptide may advantageously facilitate the expression of a recombinant TCR, polypeptide, and/or protein in a host cell. The linker peptide may comprise any suitable amino acid sequence. For example, the linker peptide may comprise the amino acid sequence of RAKRSGSGATNFSLLKQAGDVEENPGP (SEQ ID NO: 100). Upon expression of the construct, including the linker peptide by a host cell, the linker peptide may be cleaved, resulting in separated α and β chains. In an embodiment of the invention, the TCR, polypeptide, or protein may comprise an amino acid sequence comprising a full-length α chain, a full-length β chain, and a linker peptide positioned between the α and β chains.

In some embodiments, the TCR, polypeptide or protein disclosed herein comprises an α chain and/or a β chain, as disclosed herein, comprising a signal peptide. In some embodiments, the sequence of the signal peptide of any of the α chains and/or β chains disclosed herein comprises an alanine or histidine residue substituted for the wild-type residue at position 2.

In some embodiments, the TCR, polypeptide or protein disclosed herein comprises a mature version of an α chain and/or a β chain, as disclosed herein, that lacks a signal peptide.

The protein of the invention can be a recombinant antibody, or an antigen binding portion thereof, comprising at least one of the inventive polypeptides described herein. As used herein, "recombinant antibody" refers to a recombinant (e.g., genetically engineered) protein comprising at least one of the polypeptides of the invention and a polypeptide chain of an antibody, or an antigen binding portion thereof. The polypeptide of an antibody, or antigen binding portion thereof, can be a heavy chain, a light chain, a variable or constant region of a heavy or light chain, a single chain variable fragment (scFv), or an Fc, Fab, or $F(ab)_2'$ fragment of an antibody, etc. The polypeptide chain of an antibody, or an antigen binding portion thereof, can exist as a separate polypeptide of the recombinant antibody. Alternatively, the polypeptide chain of an antibody, or an antigen binding portion thereof, can exist as a polypeptide, which is expressed in frame (in tandem) with the polypeptide of the invention. The polypeptide of an antibody, or an antigen binding portion thereof, can be a polypeptide of any antibody or any antibody fragment, including any of the antibodies and antibody fragments described herein.

The TCRs, polypeptides, and proteins of the invention can be of any length, i.e., can comprise any number of amino acids, provided that the TCRs, polypeptides, or proteins retain their biological activity, e.g., the ability to specifically bind to mutated p53; detect cancer in a mammal; or treat or prevent cancer in a mammal, etc. For example, the polypeptide can be in the range of from about 50 to about 5,000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention can be, e.g., glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention can be obtained by methods known in the art such as, for example, de novo synthesis. Also, polypeptides and proteins can be recombinantly produced using the nucleic acids described herein using standard recombinant methods. See, for instance, Green and Sambrook, *Molecular Cloning: A Laboratory Manual,* $4^{th}$ ed., Cold Spring Harbor Press, Cold Spring Harbor, NY (2012). Alternatively, the TCRs, polypeptides, and/or proteins described herein can be synthesized by any of a variety of commercial entities. In this respect, the inventive TCRs, polypeptides, and proteins can be synthetic, recombinant, isolated, and/or purified.

An embodiment of the invention provides a nucleic acid comprising a nucleotide sequence encoding any of the TCRs, polypeptides, or proteins described herein. "Nucleic acid," as used herein, includes "polynucleotide," "oligonucleotide," and "nucleic acid molecule," and generally means a polymer of DNA or RNA, which can be single-stranded or double-stranded, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

An embodiment of the invention provides an isolated or purified nucleic acid comprising, from 5' to 3', a first nucleic acid sequence and a second nucleotide sequence, wherein the first and second nucleotide sequence, respectively, encode the amino sequences of SEQ ID NOs: 8 and 9; 9 and 8; 10 and 11; 11 and 10; 12 and 13; 13 and 12; 12 and 11; 11 and 12; 121 and 13; 13 and 121; 121 and 122; 122 and 121; 8 and 120; 120 and 8; 119 and 9; 9 and 119; 119 and 120; 120 and 119; 14 and 15; 15 and 14; 16 and 17; 17 and 16; 18 and 19; 19 and 18; 27 and 28; 28 and 27; 29 and 30; 30 and 29; 31 and 32; 32 and 31; 31 and 30; 30 and 31; 125 and 32; 32 and 125; 125 and 126; 126 and 125; 27 and 124; 124 and 27; 123 and 28; 28 and 123; 123 and 124; 124 and 123; 33 and 34; 34 and 33; 35 and 36; 36 and 35; 37 and 38; 38 and 37; 46 and 47; 47 and 46; 48 and 49; 49 and 48; 50 and 51; 51 and 50; 50 and 49; 49 and 50; 129 and 51; 51 and 129; 129 and 130; 130 and 129; 46 and 128; 128 and 46; 127 and 47; 47 and 127; 127 and 128; 128 and 127; 52 and 53; 53 and 52; 54 and 55; 55 and 54; 56 and 57; 57 and 56; 65 and 66; 66 and 65; 67 and 68; 68 and 67; 69 and 70; 70 and 69; 69 and 68; 68 and 69; 133 and 70; 70 and 133; 133 and 134; 134 and 133; 65 and 132; 132 and 65; 131 and 66; 66 and 131; 131 and 132; 132 and 131; 71 and 72; 72 and 71; 73 and 74; 74 and 73; 75 and 76; 76 and 75; 84 and 85; 85 and 84; 86 and 87; 87 and 86; 88 and 89; 89 and 88; 88 and 87; 87 and 88; 137 and 89; 89 and 137; 137 and 138; 138 and 137; 84 and 136; 136 and 84; 135 and 85; 85 and 135; 135 and 136; 136 and 135; 90 and 91; 91 and 90; 92 and 93; 93 and 92; 94 and 95; or 95 and 94.

In an embodiment of the invention, the nucleic acid further comprises a third nucleotide acid sequence interposed between the first and second nucleotide sequence, wherein the third nucleotide sequence encodes a cleavable linker peptide. For example, the cleavable linker peptide may comprise the amino acid sequence of RAKRSGSGATNFSLLKQAGDVEENPGP (SEQ ID NO: 100). In an embodiment, of the invention, nucleic acid encodes an amino acid sequence selected from the group consisting of SEQ ID NOs: 20, 39, 58, 77, and 96. For example, the nucleic acid may comprise a nucleotide sequence selected from the group consisting of SEQ ID NOs: 109-113.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra. For example, a nucleic acid can be chemically synthesized using naturally-occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueuosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-$N^6$-isopentenyladenine, uracil-5-oxyacetic acid (v), wybutoxosine, pseudouracil, queuosine, 2-thiocytosine, 5-methyl-2-thiouracil, 2-thiouracil, 4-thiouracil, 5-methyluracil, uracil-5-oxy acetic acid methylester, 3-(3-amino-3-N-2-carboxypropyl) uracil, and 2,6-diaminopurine. Alternatively, one or more of the nucleic acids of the invention can be purchased from any of a variety of commercial entities.

In an embodiment of the invention, the nucleic acid comprises a codon-optimized nucleotide sequence encoding any of the TCRs, polypeptides, or proteins described herein. Without being bound to any particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

An embodiment of the invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand and are particularly suitable for detecting expression of any of the inventive TCRs. It is generally appreciated that conditions can be rendered more stringent by the addition of increasing amounts of formamide.

An embodiment of the invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein. In this regard, the nucleic acid may consist essentially of any of the nucleotide sequences described herein.

The nucleic acids of the invention can be incorporated into a recombinant expression vector. In this regard, an embodiment of the invention provides a recombinant expression vector comprising any of the nucleic acids of the invention. In an embodiment of the invention, the recombinant expression vector comprises a nucleotide sequence encoding the $\alpha$ chain, the $\beta$ chain, and linker peptide.

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally-occurring or altered nucleotides or internucleotide linkages do not hinder the transcription or replication of the vector.

The recombinant expression vector of the invention can be any suitable recombinant expression vector and can be used to transform or transfect any suitable host cell. Suitable vectors include those designed for propagation and expansion or for expression or both, such as plasmids and viruses. The vector can be selected from the group consisting of the transposon/transposase series, pUC series (Fermentas Life Sciences), the pBluescript series (Stratagene, La Jolla, CA), the pET series (Novagen, Madison, WI), the pGEX series (Pharmacia Biotech, Uppsala, Sweden), and the pEX series (Clontech, Palo Alto, CA). Bacteriophage vectors, such as $\lambda$GT10, $\lambda$GT11, $\lambda$ZapII (Stratagene), $\lambda$EMBL4, and $\lambda$NM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a transposon or a viral vector, e.g., a lentiviral vector or a retroviral vector.

The recombinant expression vectors of the invention can be prepared using standard recombinant DNA techniques described in, for example, Green and Sambrook et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein, or to the nucleotide sequence which is complementary to or which hybridizes to the nucleotide sequence encoding the TCR, polypeptide, or protein. The selection of promoters, e.g., strong, weak, inducible, tissue-specific, and developmental-specific, is within the ordinary skill of the artisan. Similarly, the combining of a nucleotide sequence with a promoter is also within the skill of the artisan. The promoter can be a non-viral promoter, e.g., a human elongation factor-1α promoter, or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, and nitroreductase.

Another embodiment of the invention provides an isolated or purified TCR, polypeptide, or protein encoded by any of the nucleic acids or vectors described herein with respect to other aspects of the invention.

Still another embodiment of the invention provides an isolated or purified TCR, polypeptide, or protein that results from expression of any of the nucleic acids or vectors described herein with respect to other aspects of the invention.

Another embodiment of the invention further provides a host cell comprising any of the nucleic acids or any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. For example, the host cell may be a human lymphocyte. In an embodiment of the invention, the host cell is selected from the group consisting of a T cell, a natural killer T (NKT) cell, an invariant natural killer T (iNKT) cell, and a natural killer (NK) cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD4^+$ T cells, $CD8^+$ T cells (e.g., cytotoxic T cells), tumor infiltrating lymphocytes (TILs), memory T cells (e.g., central memory T cells and effector memory T cells), naïve T cells, and the like.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J Immunother.,* 26:332-42 (2003); and Riddell et al., *J Immunol. Methods,* 128:189-201 (1990). In an embodiment, expansion of the numbers of T cells is carried out by culturing the T cells with OKT3 antibody, IL-2, and feeder PBMC (e.g., irradiated allogeneic PBMC).

An embodiment of the invention provides a method of producing a host cell expressing a TCR that has antigenic specificity for the peptide of DRNTFRHSVVVPCEPPEVGSDCTTI (SEQ ID NO: 115) or SGNLLGRNSFEVCVCACPGRDRRTE (SEQ ID NO: 117), the method comprising contacting a cell with any of the vectors described herein under conditions that allow introduction of the vector into the cell.

The inventive TCRs, polypeptides, proteins, nucleic acids, recombinant expression vectors, and host cells (including populations thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, at least about 60%, at least about 70%, at least about 80%, at least about 90%, at least about 95%, or can be about 100%.

The inventive TCRs, polypeptides, proteins, nucleic acids, recombinant expression vectors, and host cells (including populations thereof), all of which are collectively referred to as "inventive TCR materials" hereinafter, can be formulated into a composition, such as a pharmaceutical composition. In this regard, an embodiment of the invention provides a pharmaceutical composition comprising any of the TCRs, polypeptides, proteins, nucleic acids, expression vectors, and host cells (including populations thereof), described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agent(s) or drug(s), such as a chemotherapeutic agent, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Methods for preparing administrable compositions are known or apparent to those skilled in the art and are described in more detail in, for example, *Remington: The Science and Practice of Pharmacy*, 22$^{nd}$ Ed., Pharmaceutical Press (2012). It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or intraperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

The amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen (e.g., mutated p53), or detect, treat, or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For example, an assay, which comprises comparing the extent to which target cells are lysed or IFN-γ is secreted by T cells expressing the inventive TCR, polypeptide, or protein upon administration of a given dose of such T cells to a mammal among a set of mammals of which each is given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the cancer being treated. In an embodiment in which the inventive TCR material is a population of cells, the number of cells administered per infusion may vary, e.g., from about $1\times10^6$ to about $1\times10^{12}$ cells or more. In certain embodiments, fewer than $1\times10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a chemotherapeutic agent. The practice of conjugating compounds to a chemotherapeutic agent is known in the art. One of ordinary skill in the art recognizes that sites on the inventive TCR materials, which are not necessary for the function of the inventive TCR materials, are ideal sites for attaching a bridge and/or a chemotherapeutic agent, provided that the bridge and/or chemotherapeutic agent, once attached to the inventive TCR materials, do(es) not interfere with the function of the inventive TCR materials, i.e., the ability to bind to mutated p53 or to detect, treat, or prevent cancer.

It is contemplated that the inventive pharmaceutical compositions, TCRs, polypeptides, proteins, nucleic acids, recombinant expression vectors, host cells, or populations of cells can be used in methods of treating or preventing cancer. Without being bound to a particular theory, the inventive TCRs are believed to bind specifically to mutated p53, such that the TCR (or related inventive polypeptide or protein), when expressed by a cell, is able to mediate an immune response against a target cell expressing mutated p53. In this regard, an embodiment of the invention provides a method of treating or preventing cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, for use in the treatment or prevention of cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof. Alternatively, or additionally, "prevention" may encompass preventing or delaying the recurrence of cancer, or a symptom or condition thereof.

It is also contemplated that the inventive pharmaceutical compositions, TCRs, polypeptides, proteins, nucleic acids, recombinant expression vectors, host cells, or populations of cells can be used in methods of inducing an immune response against a cancer in a mammal. In this regard, an embodiment of the invention provides a method of inducing an immune response against a cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to induce an immune response against the cancer in the mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, for use in the inducement of an immune response against a cancer in a mammal.

Also provided by an embodiment of the invention is a method of detecting the presence of cancer in a mammal. The method comprises (i) contacting a sample comprising one or more cells from the mammal with any of the inventive TCRs, polypeptides, proteins, nucleic acids, recombinant expression vectors, host cells, populations of cells, or pharmaceutical compositions described herein, thereby forming a complex, and (ii) detecting the complex, wherein detection of the complex is indicative of the presence of cancer in the mammal.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, or populations of cells, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including, e.g., any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, colorectal cancer, endometrial cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. In a preferred embodiment, the cancer is a cancer which expresses mutated p53. The cancer may express p53 with a mutation at one or both of positions 273 and 220, as defined by SEQ ID NO: 1. The cancer may express p53 with one or both of the following human p53 mutations: R273C and Y220C. In an embodiment of the invention, the cancer is an epithelial cancer. In an embodiment of the invention, the cancer is cholangiocarcinoma, melanoma, colon cancer, rectal cancer, ovarian cancer, endometrial cancer, non-small cell lung cancer (NSCLC), glioblastoma, uterine cervical cancer, head and neck cancer, breast cancer, pancreatic cancer, or bladder cancer. The cancer may be known to comprise an R273C or a Y220C mutation in human p53.

The mammal referred to in the inventive methods can be any mammal. As used herein, the term "mammal" refers to any mammal, including, but not limited to, mammals of the order Rodentia, such as mice and hamsters, and mammals of the order Lagomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perissodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

Example 1

This example demonstrates the identification of anti-p53-Y220C T cell reactivity in the TIL of Patient 4343.

Resected tumors from Patient 4343 with a hormone-positive, HER2-positive metastatic breast cancer were cut into 23 fragments and were cultured in the presence of the cytokine IL-2 to grow TILs ex vivo. The fragments (numbered F1-F7 and F9-F24) were tested for tumor-specific neoantigen reactivity, including mutant p53, by co-culturing with autologous dendritic cells pulsed with DMSO (vehicle) or the mutant p53-Y220C peptide DRNTFRHSVVVPCEPPEVGSDCTTI (SEQ ID NO: 115). IFN-γ production was measured by ELISpot assay. The results are shown in FIG. 1A. Fragment numbers F2, F3, F11, F21, and F23 were identified to contain TIL which recognized p53-Y220C.

Example 2

This example demonstrates the identification of anti-p53-R273C T cell reactivity in the TIL of Patient 4386.

Figure 1B:
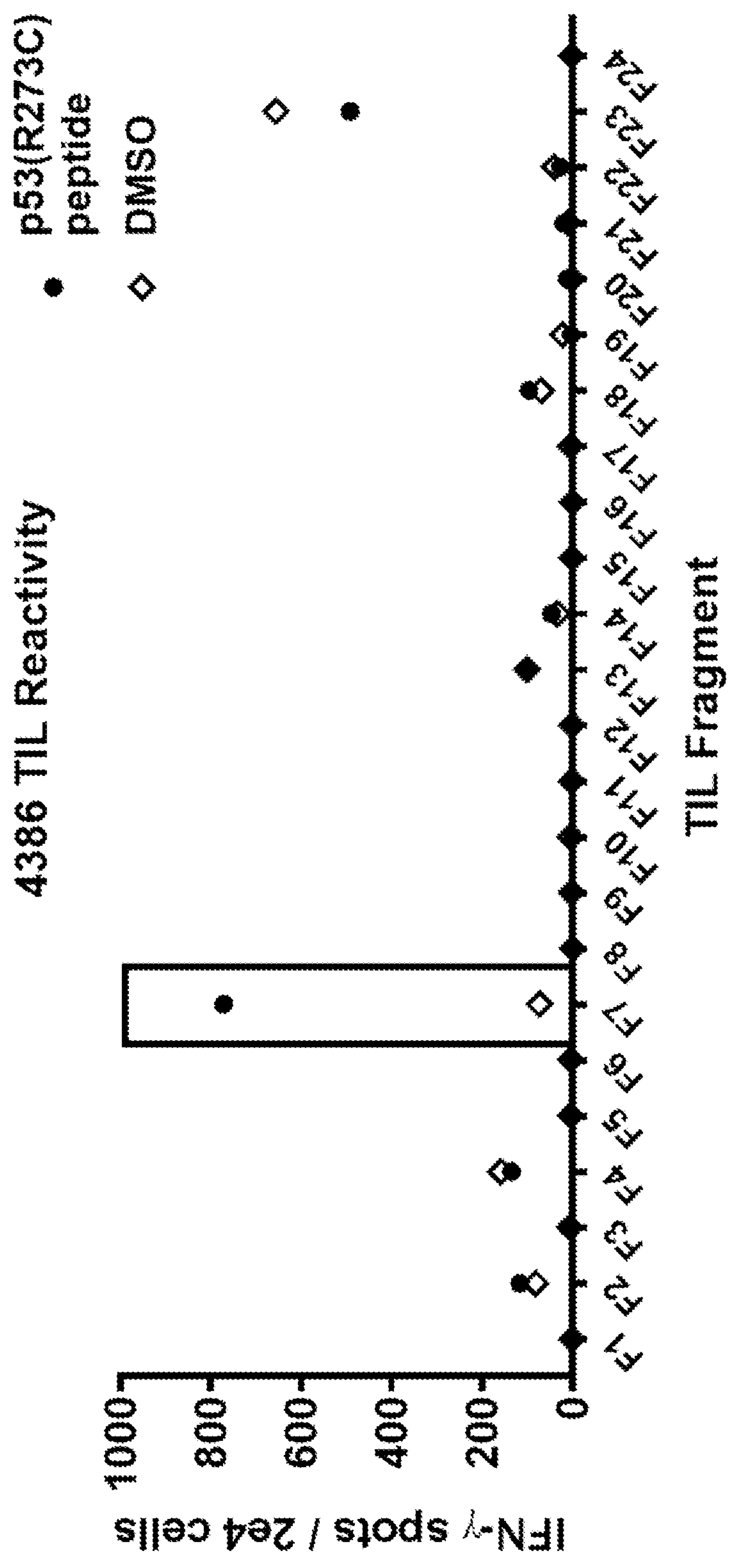
FIG. 1B is a graph showing the number of IFN-γ spots (per 2e4 cells) measured following co-culture of Patient 4386 tumor fragment numbers F1-F24 with autologous DCs pulsed with DMSO (vehicle) or mutant p53-R273C (FIG. 1B). Fragments with mutant p53 reactivity are boxed.

Resected tumors from Patient 4386's left breast axillary lymph node were cut into 24 fragments and were cultured in the presence of the cytokine IL-2 to grow TILs ex vivo. The fragments (numbered F1-F24) were tested for tumor-specific neoantigen reactivity, including mutant p53, by co-culturing with autologous dendritic cells pulsed with DMSO (vehicle) or mutant p53-R273C peptide SGNLLGRNSFEVCVCACPGRDRRTE (SEQ ID NO: 117). IFN-γ production was measured by ELISpot assay. The results are shown in FIG. 1B. Fragment number F7 was identified to contain TIL which recognized p53-R273C.

Figure 1C:
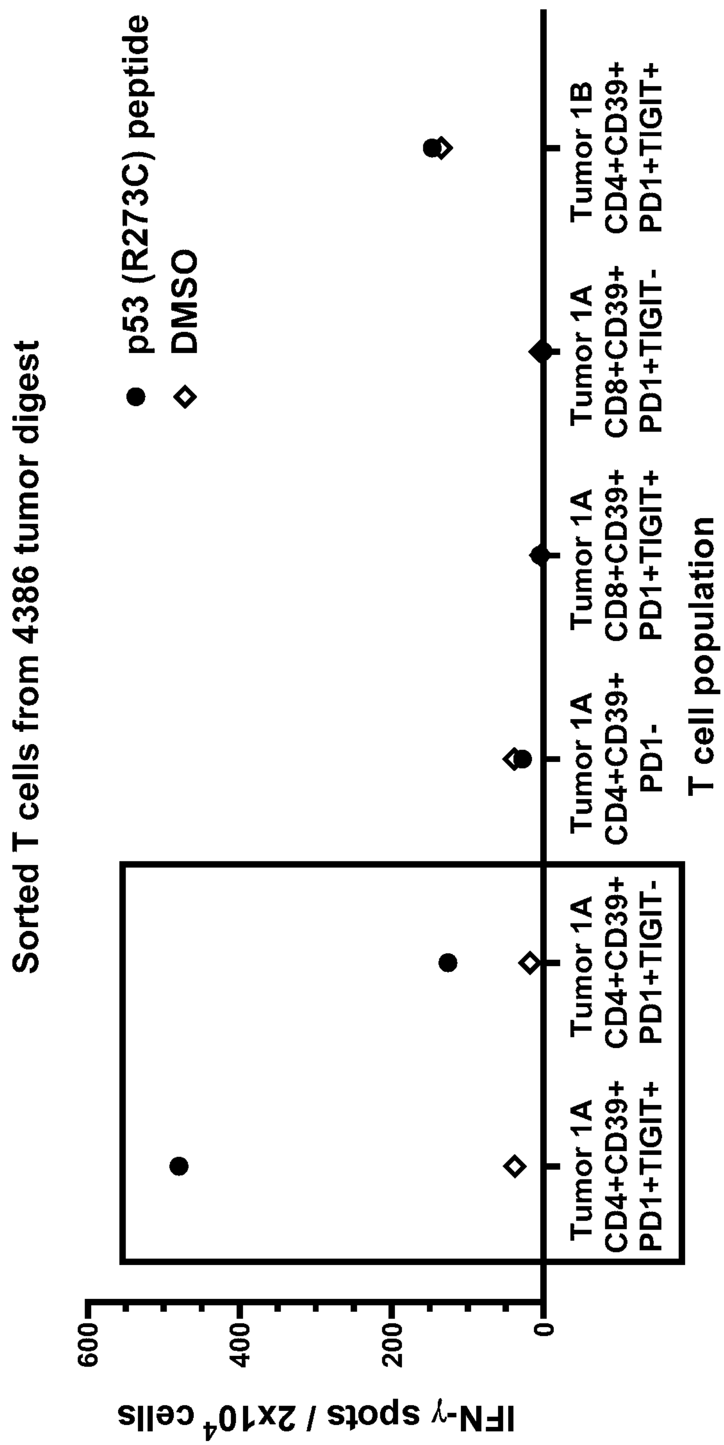
FIG. 1C is a graph showing the number of IFN-γ spots (per 2e4 cells) measured following co-culture of sorted T cells from fresh tumor digest (of Tumor 1A or Tumor 1B) of Patient 4386 with autologous DCs pulsed with DMSO (vehicle) or mutant p53-R273C. The T cells were sorted based on expression of the indicated cell surface markers. Sorted T cell populations with mutant p53 reactivity are boxed.

T cells from fresh tumor digest of Patient 4386 (Tumor 1A or Tumor 1B) were sorted based on expression of CD3 and one or more of the cell surface markers CD4, CD8, CD39, PD-1 and TIGIT. The sorted cell populations were expanded and tested for reactivity against the mutant p53-R273C peptide or DMSO. IFN-γ production was measured by ELISpot assay. The results are shown in FIG. 1C. Two cell populations from Tumor 1A were identified to contain T cells which recognized p53-R273C: $CD3^+CD4^+CD39^+PD\text{-}1^+TIGIT^+$ and $CD3^+CD4^+CD39^+PD\text{-}1^+TIGIT^-$.

Figure 1D:
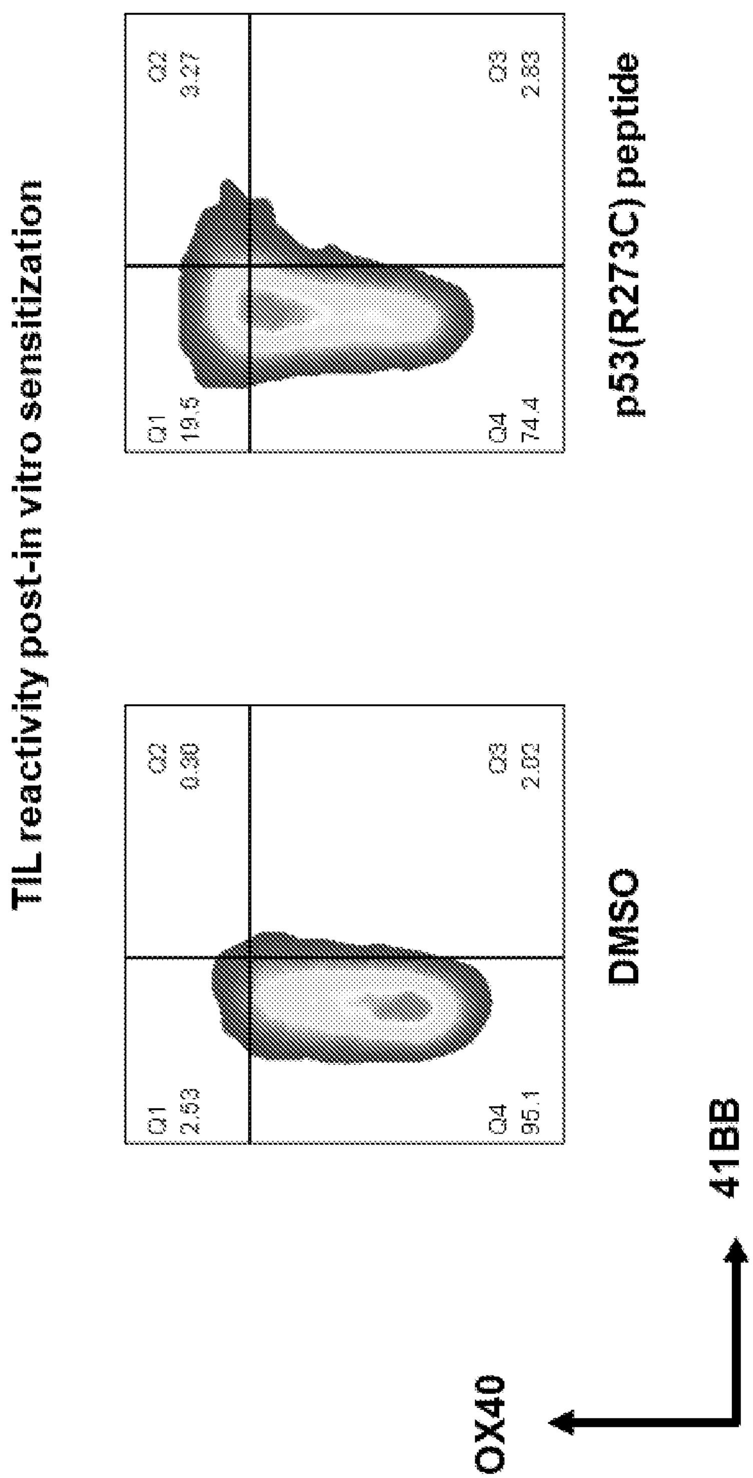
FIG. 1D shows the percentages of T cells expressing OX40 and 4-1BB following co-culture of TILs from patient 4386 with autologous DCs pulsed with DMSO (vehicle) or mutant p53-R273C peptide, as measured by flow cytometry.

TIL from patient 4386 were subjected to in vitro sensitization to enrich for neoantigen-reactive T cells, followed by testing against DMSO or the mutant p53-R273C peptide. T cell activation markers, 4-1BB and OX40, were measured by flow cytometry. The results are shown in FIG. 1D.

Example 3

This example demonstrates the isolation of an anti-p53-Y220C TCR from the reactive TIL of Example 1.

Reactive TIL were re-stimulated and sorted by 4-1BB upregulation into 96 well plates for single-cell T cell receptor (TCR) sequencing. A TCR was found, namely 4343-D TCR (TRAV12-3/TRBV27).

The sequences of the TCR alpha and beta chain variable regions were identified by single-cell TCR sequencing. The amino acid sequences of the alpha and beta chain variable regions are shown in Table 3. The CDRs are underlined. The N-terminal signal peptides are in bold font.

TABLE 3

| TCR name | TCR chain | Amino acid sequence |
|---|---|---|
| 4343-D TCR | Variable α (Predicted sequence without N-terminal signal peptide SignalP) | QQKEVEQDPGPLSVPEGAIVSLNCTYSNSAFQYFMWYRQYSRKGPELLMYTYSSGNKEDGRFTAQVDKSSKYISLFIRDSQPSDSATYLCAGGSYGKLTFGQGTILTVHP (SEQ ID NO: 8) |
| | Variable α (Predicted sequence without N-terminal signal peptide IMGT) | QKEVEQDPGPLSVPEGAIVSLNCTYSNSAFQYFMWYRQYSRKGPELLMYTYSSGNKEDGRFTAQVDKSSKYISLFIRDSQPSDSATYLCAGGSYGKLTFGQGTILTVHP (SEQ ID NO: 119) |
| | Variable β Predicted sequence without N-terminal signal peptide SignalP) | QVTQNPRYLITVTGKKLTVTCSQNMNHEYMSWYRQDPGLGLRQIYYSMNVEVTDKGDVPEGYKVSRKEKRNFPLILESPSPNQTSLYFCASSFISNQPQHFGDGTRLSIL (SEQ ID NO: 9) |
| | Variable β (Predicted sequence without N-terminal signal peptide IMGT) | EAQVTQNPRYLITVTGKKLTVTCSQNMNHEYMSWYRQDPGLGLRQIYYSMNVEVTDKGDVPEGYKVSRKEKRNFPLILESPSPNQTSLYFCASSFISNQPQHFGDGTRLSIL (SEQ ID NO: 120) |

TABLE 3-continued

| TCR name | TCR chain | Amino acid sequence |
|---|---|---|
| | Variable α (With N-terminal signal peptide with H at position 2) | **MHKSLRVLLVILWLQLSWVWS**QQKEVEQDPGPLSVPEGAIVSLNCTYSNSAFQYFMWYRQYSRKGPELLMYTYSSGNKEDGRFTAQVDKSSKYISLFIRDSQPSDSATYLCAGGSYGKLTFGQGTILTVHP (SEQ ID NO: 10) |
| | Variable α (With N-terminal signal peptide with A at position 2) | **MAKSLRVLLVILWLQLSWVWS**QQKEVEQDPGPLSVPEGAIVSLNCTYSNSAFQYFMWYRQYSRKGPELLMYTYSSGNKEDGRFTAQVDKSSKYISLFIRDSQPSDSATYLCAGGSYGKLTFGQGTILTVHP (SEQ ID NO: 121) |
| | Variable β (With N-terminal signal peptide with A at position 2) | **MAPQLLGYVVLCLLGAGPLEA**QVTQNPRYLITVTGKKLTVTCSQNMNHEYMSWYRQDPGLGLRQIYYSMNVEVTDKGDVPEGYKVSRKEKRNFPLILESPSPNQTSLYFCASSFISNQPQHFGDGTRLSIL (SEQ ID NO: 11) |
| | Variable β (With N-terminal signal peptide with H at position 2) | **MHPQLLGYVVLCLLGAGPLEA**QVTQNPRYLITVTGKKLTVTCSQNMNHEYMSWYRQDPGLGLRQIYYSMNVEVTDKGDVPEGYKVSRKEKRNFPLILESPSPNQTSLYFCASSFISNQPQHFGDGTRLSIL (SEQ ID NO: 122) |
| | Variable α (With WT N-terminal signal peptide) | **MMKSLRVLLVILWLQLSWVWS**QQKEVEQDPGPLSVPEGAIVSLNCTYSNSAFQYFMWYRQYSRKGPELLMYTYSSGNKEDGRFTAQVDKSSKYISLFIRDSQPSDSATYLCAGGSYGKLTFGQGTILTVHP (SEQ ID NO: 12) |
| | Variable β (With WT N-terminal signal peptide) | **MGPQLLGYVVLCLLGAGPLEA**QVTQNPRYLITVTGKKLTVTCSQNMNHEYMSWYRQDPGLGLRQIYYSMNVEVTDKGDVPEGYKVSRKEKRNFPLILESPSPNQTSLYFCASSFISNQPQHFGDGTRLSIL (SEQ ID NO: 13) |

Example 4

This example demonstrates the isolation of an anti-p53-R273C TCR from the reactive TIL of Example 2.

Reactive TIL were re-stimulated and sorted by 4-1BB upregulation into 96 well plates for single-cell T cell receptor (TCR) sequencing. Four TCRs were found, namely 4386-F TCR (TRAV13-2/TRBV4-3), 4386-G TCR (TRAV3/TRBV20-1), 4386-H TCR (TRAV23/TRBV7-2), and 4386-O TCR (TRAV13-2/TRBV7-3).

The sequences of the TCR alpha and beta chain variable regions were identified by single-cell TCR sequencing. The amino acid sequences of the alpha and beta chain variable regions are shown in Table 4. The CDRs are underlined. The N-terminal signal peptides are in bold font.

TABLE 4

| TCR Name | TCR chain | Amino acid sequence |
|---|---|---|
| 4386-F TCR | Variable α (Predicted sequence without N-terminal signal peptide SignalP) | ESVGLHLPTLSVQEGDNSIINCAYSNSASDYFIWYKQESGKGPQFIIDIRSNMDKRQGQRVTVLLNKTVKHLSLQIAATQPGDSAVYFCAEKSTGNQFYFGTGTSLTVIP (SEQ ID NO: 27) |
| | Variable α (Predicted sequence without N-terminal signal peptide IMGT) | GESVGLHLPTLSVQEGDNSIINCAYSNSASDYFIWYKQESGKGPQFIIDIRSNMDKRQGQRVTVLLNKTVKHLSLQIAATQPGDSAVYFCAEKSTGNQFYFGTGTSLTVIP (SEQ ID NO: 123) |
| | Variable β (Predicted sequence without N-terminal signal peptide SignalP) | METGVTQTPRHLVMGMTNKKSLKCEQHLGHNAMYWYKQSAKKPLELMFVYSLEERVENNSVPSRFSPECPNSSHLFLHLHTLQPEDSALYLCASSRVEGSDTQYFGPGTRLTVL (SEQ ID NO: 28) |
| | Variable β (Predicted sequence without N-terminal signal peptide IMGT) | ETGVTQTPRHLVMGMTNKKSLKCEQHLGHNAMYWYKQSAKKPLELMFVYSLEERVENNSVPSRFSPECPNSSHLFLHLHTLQPEDSALYLCASSRVEGSDTQYFGPGTRLTVL (SEQ ID NO: 124) |

TABLE 4-continued

| TCR Name | TCR chain | Amino acid sequence |
|---|---|---|
| | Variable α (With N-terminal signal peptide with H at position 2) | **MHGIRALFMYLWLQLDWVSRG**ESVGLHLPTLSVQEGDNSIINCAYSNSASDYFIWYKQESGKGPQFIIDIRSNMDKRQGQRVTVLLNKTVKHLSLQIAATQPGDSAVYFCAEKSTGNQFYFGTGTSLTVIP (SEQ ID NO: 29) |
| | Variable α (With N-terminal signal peptide with A at position | **MAGIRALFMYLWLQLDWVSRG**ESVGLHLPTLSVQEGDNSIINCAYSNSASDYFIWYKQESGKGPQFIIDIRSNMDKRQGQRVTVLLNKTVKHLSLQIAATQPGDSAVYFCAEKSTGNQFYFGTGTSLTVIP (SEQ ID NO: 125) |
| | Variable β (With N-terminal signal peptide with A at position | **MACRLLCCAVLCLLGAVP**METGVTQTPRHLVMGMTNKKSLKCEQHLGHNAMYWYKQSAKKPLELMFVYSLEERVENNSVPSRFSPECPNSSHLFLHLHTLQPEDSALYLCASSRVEGSDTQYFGPGTRLTVL (SEQ ID NO: 30) |
| | Variable β (With N-terminal signal peptide with H at position 2 | **MHCRLLCCAVLCLLGAVP**METGVTQTPRHLVMGMTNKKSLKCEQHLGHNAMYWYKQSAKKPLELMFVYSLEERVENNSVPSRFSPECPNSSHLFLHLHTLQPEDSALYLCASSRVEGSDTQYFGPGTRLTVL (SEQ ID NO: 126) |
| | Variable α (With WT N-terminal signal peptide) | **MAGIRALFMYLWLQLDWVSRG**ESVGLHLPTLSVQEGDNSIINCAYSNSASDYFIWYKQESGKGPQFIIDIRSNMDKRQGQRVTVLLNKTVKHLSLQIAATQPGDSAVYFCAEKSTGNQFYFGTGTSLTVIP (SEQ ID NO: 31) |
| | Variable β (With WT N-terminal signal peptide) | **MGCRLLCCAVLCLLGAVP**METGVTQTPRHLVMGMTNKKSLKCEQHLGHNAMYWYKQSAKKPLELMFVYSLEERVENNSVPSRFSPECPNSSHLFLHLHTLQPEDSALYLCASSRVEGSDTQYFGPGTRLTVL (SEQ ID NO: 32) |
| 4386-G TCR | Variable α (Predicted sequence without N-terminal signal peptide SignalP) | QSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDPTVSGTYKYIFGTGTRLKVLA (SEQ ID NO: 46) |
| | Variable α (Predicted sequence without N-terminal signal peptide IMGT) | AQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDPTVSGTYKYIFGTGTRLKVLA (SEQ ID NO: 127) |
| | Variable β (Predicted sequence without N-terminal signal peptide SignalP) | AVVSQHPSRVICKSGTSVKIECRSLDFQATTMFWYRQFPKQSLMLMATSNEGSKATYEQGVEKDKFLINHASLTLSTLTVTSAHPEDSSFYICSAIRDRSGGETQYFGPGTRLLVL (SEQ ID NO: 47) |
| | Variable β (Predicted sequence without N-terminal signal peptide IMGT) | GAVVSQHPSRVICKSGTSVKIECRSLDFQATTMFWYRQFPKQSLMLMATSNEGSKATYEQGVEKDKFLINHASLTLSTLTVTSAHPEDSSFYICSAIRDRSGGETQYFGPGTRLLVL (SEQ ID NO: 128) |
| | Variable α (With N-terminal signal peptide with H at position 2 | **MHSAPISMLAMLFTLSGLRA**QSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDPTVSGTYKYIFGTGTRLKVLA (SEQ ID NO: 48) |
| | Variable α (With N-terminal signal peptide with A at position | **MASAPISMLAMLFTLSGLRA**QSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDPTVSGTYKYIFGTGTRLKVLA (SEQ ID NO: 129) |
| | Variable β (With N-terminal signal peptide with A at position 2) | **MALLLLLLGPGSGLG**AVVSQHPSRVICKSGTSVKIECRSLDFQATTMFWYRQFPKQSLMLMATSNEGSKATYEQGVEKDKFLINHASLTLSTLTVTSAHPEDSSFYICSAIRDRSGGETQYFGPGTRLLVL (SEQ ID NO: 49) |
| | Variable β (With N-terminal signal peptide with H at position 2) | **MHLLLLLLGPGSGLG**AVVSQHPSRVICKSGTSVKIECRSLDFQATTMFWYRQFPKQSLMLMATSNEGSKATYEQGVEKDKFLINHASLTLSTLTVTSAHPEDSSFYICSAIRDRSGGETQYFGPGTRLLVL (SEQ ID NO: 130) |

TABLE 4-continued

| TCR Name | TCR chain | Amino acid sequence |
|---|---|---|
| | Variable α (With WT N-terminal signal peptide) | **MASAPISMLAMLFTLSGLRA**QSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDPTVSGTYKYIFGTGTRLKVLA (SEQ ID NO: 50) |
| | Variable β (With WT N-terminal signal peptide) | **MLLLLLLLGPGSGLG**AVVSQHPSRVICKSGTSVKIECRSLDFQATTMFWYRQFPKQSLMLMATSNEGSKATYEQGVEKDKFLINHASLTLSTLTVTSAHPEDSSFYICSAIRDRSGGETQYFGPGTRLLVL (SEQ ID NO: 51) |
| 4386-H TCR | Variable α (Predicted sequence without N-terminal signal peptide SignalP) | QQKEKSDQQQVKQSPQSLIVQKGGISIINCAYENTAFDYFPWYQQFPGKGPALLIAIRPDVSEKKEGRFTISFNKSAKQFSLHIMDSQPGDSATYFCAAKRQGGSEKLVFGKGTKLTVNP (SEQ ID NO: 65) |
| | Variable α (Predicted sequence without N-terminal signal peptide IMGT) | QQQVKQSPQSLIVQKGGISIINCAYENTAFDYFPWYQQFPGKGPALLIAIRPDVSEKKEGRFTISFNKSAKQFSLHIMDSQPGDSATYFCAAKRQGGSEKLVFGKGTKLTVNP (SEQ ID NO: 131) |
| | Variable β (Predicted sequence without N-terminal signal peptide SignalP) | GVSQSPSNKVTEKGKDVELRCDPISGHTALYWYRQSLGQGLEFLIYFQGNSAPDKSGLPSDRFSAERTGGSVSTLTIQRTQQEDSAVYLCASSLGGSSETQYFGPGTRLLVL (SEQ ID NO: 66) |
| | Variable β (Predicted sequence without N-terminal signal peptide IMGT) | GAGVSQSPSNKVTEKGKDVELRCDPISGHTALYWYRQSLGQGLEFLIYFQGNSAPDKSGLPSDRFSAERTGGSVSTLTIQRTQQEDSAVYLCASSLGGSSETQYFGPGTRLLVL (SEQ ID NO: 132) |
| | Variable α (With N-terminal signal peptide with H at position 2) | **MHKILGASFLVLWLQLCWVSG**QQKEKSDQQQVKQSPQSLIVQKGGISIINCAYENTAFDYFPWYQQFPGKGPALLIAIRPDVSEKKEGRFTISFNKSAKQFSLHIMDSQPGDSATYFCAAKRQGGSEKLVFGKGTKLTVNP (SEQ ID NO: 67) |
| | Variable α (With N-terminal signal peptide with A at position 2) | **MAKILGASFLVLWLQLCWVSG**QQKEKSDQQQVKQSPQSLIVQKGGISIINCAYENTAFDYFPWYQQFPGKGPALLIAIRPDVSEKKEGRFTISFNKSAKQFSLHIMDSQPGDSATYFCAAKRQGGSEKLVFGKGTKLTVNP (SEQ ID NO: 133) |
| | Variable β (With N-terminal signal peptide with A at position 2) | **MATRLLFWVAFCLLGADHTGA**GVSQSPSNKVTEKGKDVELRCDPISGHTALYWYRQSLGQGLEFLIYFQGNSAPDKSGLPSDRFSAERTGGSVSTLTIQRTQQEDSAVYLCASSLGGSSETQYFGPGTRLLVL (SEQ ID NO: 68) |
| | Variable β (With N-terminal signal peptide with H at position 2) | **MHTRLLFWVAFCLLGADHTGA**GVSQSPSNKVTEKGKDVELRCDPISGHTALYWYRQSLGQGLEFLIYFQGNSAPDKSGLPSDRFSAERTGGSVSTLTIQRTQQEDSAVYLCASSLGGSSETQYFGPGTRLLVL (SEQ ID NO: 134) |
| | Variable α (With WT N-terminal signal peptide) | **MDKILGASFLVLWLQLCWVSG**QQKEKSDQQQVKQSPQSLIVQKGGISIINCAYENTAFDYFPWYQQFPGKGPALLIAIRPDVSEKKEGRFTISFNKSAKQFSLHIMDSQPGDSATYFCAAKRQGGSEKLVFGKGTKLTVNP (SEQ ID NO: 69) |
| | Variable β (With WT N-terminal signal peptide) | **MGTRLLFWVAFCLLGADHTGA**GVSQSPSNKVTEKGKDVELRCDPISGHTALYWYRQSLGQGLEFLIYFQGNSAPDKSGLPSDRFSAERTGGSVSTLTIQRTQQEDSAVYLCASSLGGSSETQYFGPGTRLLVL (SEQ ID NO: 70) |

TABLE 4-continued

| TCR Name | TCR chain | Amino acid sequence |
|---|---|---|
| 4386-O TCR | Variable α (Predicted sequence without N-terminal signal peptide SignalP) | ESVGLHLPTLSVQEGDNSIINCAYSNSASDYFIWYKQESGKGP QFIIDIRSNMDKRQGQRVTVLLNKTVKHLSLQIAATQPGDSAV YFCAEKRRGGSEKLVFGKGTKLTVNP (SEQ ID NO: 84) |
| | Variable α (Predicted sequence without N-terminal signal peptide IMGT) | GESVGLHLPTLSVQEGDNSIINCAYSNSASDYFIWYKQESGKG PQFIIDIRSNMDKRQGQRVTVLLNKTVKHLSLQIAATQPGDSA VYFCAEKRRGGSEKLVFGKGTKLTVNP (SEQ ID NO: 135) |
| | Variable β (Predicted sequence without N-terminal signal peptide SignalP) | GVSQTPSNKVTEKGKYVELRCDPISGHTALYWYRQSLGQGPE FLIYFQGTGAADDSGLPNDRFFAVRPEGSVSTLKIQRTERGDSA VYLCASSPGGSQETQYFGPGTRLLVL (SEQ ID NO: 85) |
| | Variable β (Predicted sequence without N-terminal signal peptide IMGT) | GAGVSQTPSNKVTEKGKYVELRCDPISGHTALYWYRQSLGQG PEFLIYFQGTGAADDSGLPNDRFFAVRPEGSVSTLKIQRTERGD SAVYLCASSPGGSQETQYFGPGTRLLVL (SEQ ID NO: 136) |
| | Variable α (With N-terminal signal peptide with H at position | MHGIRALFMYLWLQLDWVSRGESVGLHLPTLSVQEGDNSII NCAYSNSASDYFIWYKQESGKGPQFIIDIRSNMDKRQGQRVTV LLNKTVKHLSLQIAATQPGDSAVYFCAEKRRGGSEKLVFGKG TKLTVNP (SEQ ID NO: 86) |
| | Variable α (With N-terminal signal peptide with A at position 2) | MAGIRALFMYLWLQLDWVSRGESVGLHLPTLSVQEGDNSII NCAYSNSASDYFIWYKQESGKGPQFIIDIRSNMDKRQGQRVTV LLNKTVKHLSLQIAATQPGDSAVYFCAEKRRGGSEKLVFGKG TKLTVNP (SEQ ID NO: 137) |
| | Variable β (With N-terminal signal peptide with A at position 2) | MATRLLCWAALCLLGADHTGAGVSQTPSNKVTEKGKYVEL RCDPISGHTALYWYRQSLGQGPEFLIYFQGTGAADDSGLPNDR FFAVRPEGSVSTLKIQRTERGDSAVYLCASSPGGSQETQYFGPG TRLLVL (SEQ ID NO: 87) |
| | Variable β (With N-terminal signal peptide with H at position 2) | MHTRLLCWAALCLLGADHTGAGVSQTPSNKVTEKGKYVEL RCDPISGHTALYWYRQSLGQGPEFLIYFQGTGAADDSGLPNDR FFAVRPEGSVSTLKIQRTERGDSAVYLCASSPGGSQETQYFGPG TRLLVL (SEQ ID NO: 138) |
| | Variable α (With WT N-terminal signal peptide) | MAGIRALFMYLWLQLDWVSRGESVGLHLPTLSVQEGDNSII NCAYSNSASDYFIWYKQESGKGPQFIIDIRSNMDKRQGQRVTV LLNKTVKHLSLQIAATQPGDSAVYFCAEKRRGGSEKLVFGKG TKLTVNP (SEQ ID NO: 88) |
| | Variable β (With WT N-terminal signal peptide) | MGTRLLCWAALCLLGADHTGAGVSQTPSNKVTEKGKYVEL RCDPISGHTALYWYRQSLGQGPEFLIYFQGTGAADDSGLPNDR FFAVRPEGSVSTLKIQRTERGDSAVYLCASSPGGSQETQYFGPG TRLLVL (SEQ ID NO: 89) |

Example 5

This example demonstrates the construction of retroviral vectors encoding the respective TCRs of Examples 3-4.

Nucleotide sequences encoding the variable regions of the α and β chains of the TCRs of Tables 3-4 were obtained and codon optimized. The TCRβ VDJ regions were fused to the mouse TCRβ constant chain. The TCRα VJ regions were fused to the mouse TCRα constant chain. Without being bound to a particular theory or mechanism, it is believed that replacing the constant regions of the human TCRα and TCRPβ chains with the corresponding murine constant regions improves TCR expression and functionality (Cohen et al., *Cancer Res.,* 66(17): 8878-86 (2006)).

In addition, the murine TCRα and TCRβ constant chains were cysteine-modified. Transmembrane hydrophobic mutations were introduced into the murine TCRα constant chain. Without being bound to a particular theory or mechanism, it is believed that these modifications result in preferential pairing of the introduced TCR chains and enhanced TCR surface expression and functionality (Cohen et al., *Cancer Res.,* 67(8):3898-903 (2007); Haga-Friedman et al., *J. Immu.,* 188: 5538-5546 (2012)).

To facilitate cloning of the TCR expression cassette into the MSGV1 vector 5'NcoI site, and to introduce a Kozak sequence, the second amino acid in the N-terminal signal peptide of the TCRVα chain was changed to an histidine (H), and the second amino acid in the N-terminal signal peptide of the TCRVβ chain was changed to an alanine (A).

The full length α and β chains of each of the five TCRs, including these modifications to the constant region, are shown in Table 5. In Table 5, the CDRs are underlined, the constant region is in italics, and the modified amino acid residues of the constant region are underlined and in bold.

TABLE 5

| TCR Name | TCR chain | Amino acid sequence |
|---|---|---|
| 4343-D TCR | Cys-substituted, LVL-modified α chain with N-terminal signal peptide | MHKSLRVLLVILWLQLSWVWSQQKEVEQDPGPLSVPEGAIVSLNCTYSNSAFQYFMWYRQYSRKGPELLMYTYSSGNKEDGRFTAQVDKSSKYISLFIRDSQPSDSATYLCAGGSYGKLTFGQGTILTVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSS (SEQ ID NO: 14) |
| | Cys-substituted, LVL-modified β chain with N-terminal signal peptide | MAPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASSFISNQPQHFGDGTRLSILEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 15) |
| | Cys-substituted, LVL-modified α chain with WT N-terminal signal peptide | MMKSLRVLLVILWLQLSWVWSQQKEVEQDPGPLSVPEGAIVSLNCTYSNSAFQYFMWYRQYSRKGPELLMYTYSSGNKEDGRFTAQVDKSSKYISLFIRDSQPSDSATYLCAGGSYGKLTFGQGTILTVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSS (SEQ ID NO: 16) |
| | Cys-substituted, LVL-modified β chain with WT N-terminal signal peptide | MGPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYFCASSFISNQPQHFGDGTRLSILEDLRNVTPPKVSLFEPSKAELANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 17) |
| | Cys-substituted, LVL-modified α chain predicted sequence without N-terminal signal peptide | QQKEVEQDPGPLSVPEGAIVSLNCTYSNSAFQYFMWYRQYSRKGPELLMYTYSSGNKEDGRFTAQVDKSSKYISLFIRDSQPSDSATYLCAGGSYGKLTFGQGTILTVHPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSS (SEQ ID NO: 18) |
| | Cys-substituted, LVL-modified β chain predicted sequence without N-terminal signal peptide | QVTQNPRYLITVTGKKLTVTCSQNMNHEYMSWYRQDPGLGLRQIYYSMNVEVTDKGDVPEGYKVSRKEKRNFPLILESPSPNQTSLYFCASSFISNQPQHFGDGTRLSILEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 19) |
| 4386-F | Cys-substituted, LVL-modified α chain with N-terminal signal peptide | MHGIRALFMYLWLQLDWVSRGESVGLHLPTLSVQEGDNSIINCAYSNSASDYFIWYKQESGKGPQFIIDIRSNMDKRQGQRVTVLLNKTVKHLSLQIAATQPGDSAVYFCAEKSTGNQFYFGTGTSLTVIPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSS (SEQ ID NO: 33) |
| | Cys-substituted, LVL-modified β chain with N-terminal signal peptide | MACRLLCCAVLCLLGAVPMETGVTQTPRHLVMGMTNKKSLKCEQHLGHNAMYWYKQSAKKPLELMFVYSLEERVENNSVPSRFSPECPNSSHLFLHLHTLQPEDSALYLCASSRVEGSDTQYFGPGTRLTVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS (SEQ ID NO: 34) |
| | Cys-substituted, LVL-modified α chain with WT N-terminal signal peptide | MAGIRALFMYLWLQLDWVSRGESVGLHLPTLSVQEGDNSIINCAYSNSASDYFIWYKQESGKGPQFIIDIRSNMDKRQGQRVTVLLNKTVKHLSLQIAATQPGDSAVYFCAEKSTGNQFYFGTGTSLTVIPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSS (SEQ ID NO: 35) |

TABLE 5-continued

| TCR Name | TCR chain | Amino acid sequence |
|---|---|---|
| | Cys-substituted, LVL-modified β chain with WT N-terminal signal peptide | MGCRLLCCAVLCLLGAVPMETGVTQTPRHLVMGMTNKKSLKCEQH LGHNAMYWYKQSAKKPLELMFVYSLEERVENNSVPSRFSPECPNSSH LFLHLHTLQPEDSALYLCASSRVEGSDTQYFGPGTRLTVL*EDLRNVTPP KVSLFEPSKAEIANKQKATLVCLARGFFPDHVELSWWVNGKEVHSGV**C**TD PQAYKESNYSYCLSSRLRVSATFWHNPRNHFRCQVQFHGLSEEDKWPEGS PKPVTQNISAEAWGRADCGITSASYQQGVLSATILYEILLGKATLYAVLVSTL VVMAMVKRKNS* (SEQ ID NO: 36) |
| | Cys-substituted, LVL-modified α chain predicted sequence without N-terminal signal peptide | ESVGLHLPTLSVQEGDNSIINCAYSNSASDYFIWYKQESGKGPQFIIDIR SNMDKRQGQRVTVLLNKTVKHLSLQIAATQPGDSAVYFCAEKSTGN QFYFGTGTSLTVIP*NIQNPEPAVYQLKDPRSQDSTLCLFTDFDSQINVPKT MESGTFITDK**C**VLDMKAMDSKSNGAIAWSNQTSFTCQDIFKETNATYPSS DVPCDATLTEKSFETDMNLNFQNL**L**V**IV**LRILLLKVAGFNLLMTLRLWSS* (SEQ ID NO: 37) |
| | Cys-substituted, LVL-modified β chain predicted sequence without N-terminal signal peptide | METGVTQTPRHLVMGMTNKKSLKCEQHLGHNAMYWYKQSAKKPLE LMFVYSLEERVENNSVPSRFSPECPNSSHLFLHLHTLQPEDSALYLCAS SRVEGSDTQYFGPGTRLTVL*EDLRNVTPPKVSLFEPSKAEIANKQKATLV CLARGFFPDHVELSWWVNGKEVHSGV**C**TDPQAYKESNYSYCLSSRLRVSA TFWHNPRNHFRCQVQFHGLSEEDKWPEGSPKPVTQNISAEAWGRADCGI TSASYQQGVLSATILYEILLGKATLYAVLVSTLVVMAMVKRKNS* (SEQ ID NO: 38) |
| 4386-G | Cys-substituted, LVL-modified α chain with N-terminal signal peptide | MHSAPISMLAMLFTLSGLRAQSVAQPEDQVNVAEGNPLTVKCTYSVS GNPYLFWYVQYPNRGLQFLLKYITGDNLVKGSYGFEAEFNKSQTSFH LKKPSALVSDSALYFCAVRDPTVSGTYKYIFGTGTRLKVLA*NIQNPEP AVYQLKDPRSQDSTLCLFTDFDSQINVPKTMESGTFITDK**C**VLDMKAMDS KSNGAIAWSNQTSFTCQDIFKETNATYPSSDVPCDATLTEKSFETDMNLNF QN**L**LV**IV**LRILLLKVAGFNLLMTLRLWSS* (SEQ ID NO: 52) |
| | Cys-substituted, LVL-modified β chain with N-terminal signal peptide | MALLLLLLGPGSGLGAVVSQHPSRVICKSGTSVKIECRSLDFQATTMF WYRQFPKQSLMLMATSNEGSKATYEQGVEKDKFLINHASLTLSTLTV TSAHPEDSSFYICSAIRDRSGGETQYFGPGTRLLVL*EDLRNVTPPKVSLF EPSKAEIANKQKATLVCLARGFFPDHVELSWWVNGKEVHSGV**C**TDPQAY KESNYSYCLSSRLRVSATFWHNPRNHFRCQVQFHGLSEEDKWPEGSPKPV TQNISAEAWGRADCGITSASYQQGVLSATILYEILLGKATLYAVLVSTLVVMA MVKRKNS* (SEQ ID NO: 53) |
| | Cys-substituted, LVL-modified α chain with WT N-terminal signal peptide | MASAPISMLAMLFTLSGLRAQSVAQPEDQVNVAEGNPLTVKCTYSVS GNPYLFWYVQYPNRGLQFLLKYITGDNLVKGSYGFEAEFNKSQTSFH LKKPSALVSDSALYFCAVRDPTVSGTYKYIFGTGTRLKVLA*NIQNPEP AVYQLKDPRSQDSTLCLFTDFDSQINVPKTMESGTFITDK**C**VLDMKAMDS KSNGAIAWSNQTSFTCQDIFKETNATYPSSDVPCDATLTEKSFETDMNLNF QN**L**LV**IV**LRILLLKVAGFNLLMTLRLWSS* (SEQ ID NO: 54) |
| | Cys-substituted, LVL-modified β chain with WT N-terminal signal peptide | MLLLLLLLGPGSGLGAVVSQHPSRVICKSGTSVKIECRSLDFQATTMF WYRQFPKQSLMLMATSNEGSKATYEQGVEKDKFLINHASLTLSTLTV TSAHPEDSSFYICSAIRDRSGGETQYFGPGTRLLVL*EDLRNVTPPKVSLF EPSKAEIANKQKATLVCLARGFFPDHVELSWWVNGKEVHSGV**C**TDPQAY KESNYSYCLSSRLRVSATFWHNPRNHFRCQVQFHGLSEEDKWPEGSPKPV TQNISAEAWGRADCGITSASYQQGVLSATILYEILLGKATLYAVLVSTLVVMA MVKRKNS* (SEQ ID NO: 55) |
| | Cys-substituted, LVL-modified α chain predicted sequence without N-terminal signal peptide | QSVAQPEDQVNVAEGNPLTVKCTYSVSGNPYLFWYVQYPNRGLQFL LKYITGDNLVKGSYGFEAEFNKSQTSFHLKKPSALVSDSALYFCAVRD PTVSGTYKYIFGTGTRLKVLA*NIQNPEPAVYQLKDPRSQDSTLCLFTDF DSQINVPKTMESGTFITDK**C**VLDMKAMDSKSNGAIAWSNQTSFTCQDIFK ETNATYPSSDVPCDATLTEKSFETDMNLNFQNL**L**V**IV**LRILLLKVAGFNLL MTLRLWSS* (SEQ ID NO: 56) |
| | Cys-substituted, LVL-modified ß chain predicted sequence without N-terminal signal peptide | AVVSQHPSRVICKSGTSVKIECRSLDFQATTMFWYRQFPKQSLMLMA TSNEGSKATYEQGVEKDKFLINHASLTLSTLTVTSAHPEDSSFYICSAI RDRSGGETQYFGPGTRLLVL*EDLRNVTPPKVSLFEPSKAEIANKQKATLV CLARGFFPDHVELSWWVNGKEVHSGV**C**TDPQAYKESNYSYCLSSRLRVSA TFWHNPRNHFRCQVQFHGLSEEDKWPEGSPKPVTQNISAEAWGRADCGI TSASYQQGVLSATILYEILLGKATLYAVLVSTLVVMAMVKRKNS* (SEQ ID NO: 57) |

TABLE 5-continued

| TCR Name | TCR chain | Amino acid sequence |
|---|---|---|
| 4386-H | Cys-substituted, LVL-modified α chain with N-terminal signal peptide | MHKILGASFLVLWLQLCWVSGQQKEKSDQQQVKQSPQSLIVQKGGIS IINCAYENTAFDYFPWYQQFPGKGPALLIAIRPDVSEKKEGRFTISFNK SAKQFSLHIMDSQPGDSATYFCAAKRQGGSEKLVFGKGTKLTVNPNI QNPEPAVYQLKDPRSQDSTLCLFTDFDSQINVPKTMESGTFITDKCVLDM KAMDSKSNGAIAWSNQTSFTCQDIFKETNATYPSSDVPCDATLTEKSFETD MNLNFQNLLVIVLRILLLKVAGFNLLMTLRLWSS (SEQ ID NO: 71) |
| | Cys-substituted, LVL-modified β chain with N-terminal signal peptide | MATRLLFWVAFCLLGADHTGAGVSQSPSNKVTEKGKDVELRCDPISG HTALYWYRQSLGQGLEFLIYFQGNSAPDKSGLPSDRFSAERTGGSVST LTIQRTQQEDSAVYLCASSLGGSSETQYFGPGTRLLVLEDLRNVTPPKV SLFEPSKAEIANKQKATLVCLARGFFPDHVELSWWVNGKEVHSGVCTDPQ AYKESNYSYCLSSRLRVSATFWHNPRNHFRCQVQFHGLSEEDKWPEGSPK PVTQNISAEAWGRADCGITSASYQQGVLSATILYEILLGKATLYAVLVSTLVV MAMVKRKNS (SEQ ID NO: 72) |
| | Cys-substituted, LVL-modified α chain with WT N-terminal signal peptide | MDKILGASFLVLWLQLCWVSGQQKEKSDQQQVKQSPQSLIVQKGGIS IINCAYENTAFDYFPWYQQFPGKGPALLIAIRPDVSEKKEGRFTISFNK SAKQFSLHIMDSQPGDSATYFCAAKRQGGSEKLVFGKGTKLTVNPNI QNPEPAVYQLKDPRSQDSTLCLFTDFDSQINVPKTMESGTFITDKCVLDM KAMDSKSNGAIAWSNQTSFTCQDIFKETNATYPSSDVPCDATLTEKSFETD MNLNFQNLLIVLRILLLKVAGFNLLMTLRLWSS (SEQ ID NO: 73) |
| | Cys-substituted, LVL-modified β chain with WT N-terminal signal peptide | MGTRLLFWVAFCLLGADHTGAGVSQSPSNKVTEKGKDVELRCDPISG HTALYWYRQSLGQGLEFLIYFQGNSAPDKSGLPSDRFSAERTGGSVST LTIQRTQQEDSAVYLCASSLGGSSETQYFGPGTRLLVLEDLRNVTPPKV SLFEPSKAEIANKQKATLVCLARGFFPDHVELSWWVNGKEVHSGVCTDPQ AYKESNYSYCLSSRLRVSATFWHNPRNHFRCQVQFHGLSEEDKWPEGSPK PVTQNISAEAWGRADCGITSASYQQGVLSATILYEILLGKATLYAVLVSTLVV MAMVKRKNS (SEQ ID NO: 74) |
| | Cys-substituted, LVL-modified α chain predicted sequence without N-terminal signal peptide | QQKEKSDQQQVKQSPQSLIVQKGGISIINCAYENTAFDYFPWYQQFPG KGPALLIAIRPDVSEKKEGRFTISFNKSAKQFSLHIMDSQPGDSATYFC AAKRQGGSEKLVFGKGTKLTVNPNIQNPEPAVYQLKDPRSQDSTLCLFT DFDSQINVPKTMESGTFITDKCVLDMKAMDSKSNGAIAWSNQTSFTCQDI FKETNATYPSSDVPCDATLTEKSFETDMNLNFQNLLIVLRILLLKVAGFN LLMTLRLWSS (SEQ ID NO: 75) |
| | Cys-substituted, LVL-modified β chain predicted sequence without N-terminal signal peptide | GVSQSPSNKVTEKGKDVELRCDPISGHTALYWYRQSLGQGLEFLIYFQ GNSAPDKSGLPSDRFSAERTGGSVSTLTIQRTQQEDSAVYLCASSLGG SSETQYFGPGTRLLVLEDLRNVTPPKVSLFEPSKAEIANKQKATLVCLAR GFFPDHVELSWWVNGKEVHSGVCTDPQAYKESNYSYCLSSRLRVSATFWH NPRNHFRCQVQFHGLSEEDKWPEGSPKPVTQNISAEAWGRADCGITSASY QQGVLSATILYEILLGKATLYAVLVSTLVVMAMVKRKNS (SEQ ID NO: 76) |
| 4386-O | Cys-substituted, LVL-modified α chain with N-terminal signal peptide | MHGIRALFMYLWLQLDWVSRGESVGLHLPTLSVQEGDNSIINCAYSN SASDYFIWYKQESGKGPQFIIDIRSNMDKRQGQRVTVLLNKTVKHLSL QIAATQPGDSAVYFCAEKRRGGSEKLVFGKGTKLTVNPNIQNPEPAVY QLKDPRSQDSTLCLFTDFDSQINVPKTMESGTFITDKCVLDMKAMDSKSN GAIAWSNQTSFTCQDIFKETNATYPSSDVPCDATLTEKSFETDMNLNFQNL LVIVLRILLLKVAGFNLLMTLRLWSS (SEQ ID NO: 90) |
| | Cys-substituted, LVL-modified β chain with N-terminal signal peptide | MATRLLCWAALCLLGADHTGAGVSQTPSNKVTEKGKYVELRCDPIS GHTALYWYRQSLGQGPEFLIYFQGTGAADDSGLPNDRFFAVRPEGSV STLKIQRTERGDSAVYLCASSPGGSQETQYFGPGTRLLVLEDLRNVTPP KVSLFEPSKAEIANKQKATLVCLARGFFPDHVELSWWVNGKEVHSGVCTD PQAYKESNYSYCLSSRLRVSATFWHNPRNHFRCQVQFHGLSEEDKWPEGS PKPVTQNISAEAWGRADCGITSASYQQGVLSATILYEILLGKATLYAVLVSTL VVMAMVKRKNS (SEQ ID NO: 91) |
| | Cys-substituted, LVL-modified α chain with WT N-terminal signal peptide | MAGIRALFMYLWLQLDWVSRGESVGLHLPTLSVQEGDNSIINCAYSN SASDYFIWYKQESGKGPQFIIDIRSNMDKRQGQRVTVLLNKTVKHLSL QIAATQPGDSAVYFCAEKRRGGSEKLVFGKGTKLTVNPNIQNPEPAVY QLKDPRSQDSTLCLFTDFDSQINVPKTMESGTFITDKCVLDMKAMDSKSN GAIAWSNQTSFTCQDIFKETNATYPSSDVPCDATLTEKSFETDMNLNFQNL LVIVLRILLLKVAGFNLLMTLRLWSS (SEQ ID NO: 92) |
| | Cys-substituted, LVL-modified β | MGTRLLCWAALCLLGADHTGAGVSQTPSNKVTEKGKYVELRCDPIS GHTALYWYRQSLGQGPEFLIYFQGTGAADDSGLPNDRFFAVRPEGSV |

TABLE 5-continued

| TCR Name | TCR chain | Amino acid sequence |
|---|---|---|
| | chain with WT N-terminal signal peptide | STLKIQRTERGDSAVYLCASSPGGSQETQYFGPGTRLLVL*EDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS* (SEQ ID NO: 93) |
| | Cys-substituted, LVL-modified α chain predicted sequence without N-terminal signal peptide | ESVGLHLPTLSVQEGDNSIINCAYSNSASDYFIWYKQESGKGPQFIIDIRSNMDKRQGQRVTVLLNKTVKHLSLQIAATQPGDSAVYFCAEKRRGGSEKLVFGKGTKLTVNP*NIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLIVLRILLLKVAGFNLLMTLRLWSS* (SEQ ID NO: 94) |
| | Cys-substituted, LVL-modified β chain predicted sequence without N-terminal signal peptide | GVSQTPSNKVTEKGKYVELRCDPISGHTALYWYRQSLGQGPEFLIYFQGTGAADDSGLPNDRFFAVRPEGSVSTLKIQRTERGDSAVYLCASSPGGSQETQYFGPGTRLLVL*EDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS* (SEQ ID NO: 95) |

Nucleotide sequences encoding the variable regions of the α and β chains of the TCRs of Table 5 were cloned into an MSGV1-based retroviral vector with the following expression cassette configuration: 5'NcoI-VDJβ-mCβ-Furin/Ser-Gly/P2A-VJα-mCα-EcoRI3'.

The TCRβ and TCRα chains were separated by a Furin Ser/Gly P2A linker RAKRSGSGATNFSLLKQAGDVEENPGP (SEQ ID NO: 100). Without being bound to a particular theory or mechanism, it is believed that the linker provides comparable expression efficiency of the two chains (Szymczak et al., *Nat. Biotechnol.,* 22(5):589-94 (2004)).

The TCR expression cassette of the retroviral vector encoded, from 5' to 3', the TCRβ and TCRα chains separated by the linker. The nucleotide sequences of the TCR expression cassettes are shown in Table 6.

TABLE 6

| TCR Name | TCR Expression Cassette |
|---|---|
| 4343-D | SEQ ID NO: 109 |
| 4386-F | SEQ ID NO: 110 |
| 4386-G | SEQ ID NO: 111 |
| 4386-H | SEQ ID NO: 112 |
| 4386-O | SEQ ID NO: 113 |

The amino acid sequences encoded by each respective TCR expression cassette is shown in Table 7. In Table 7, the CDRs are underlined, the constant regions are italicized, and the linker is shown in bold.

TABLE 7

| TCR Name | Amino acid sequence encoded by TCR Expression Cassette |
|---|---|
| 4343-D | MAPQLLGYVVLCLLGAGPLEAQVTQNPRYLITVTGKKLTVTCSQNMNHEYMSWYRQDPGLGLRQIYYSMNVEVTDKGDVPEGYKVSRKEKRNFPLILESPSPNQTSLYF*CASSFISNQPQHFGDGTRLSILEDLRNVTPPKVSLFEPSKAEIANKQKATLVCLARGFFPDHVELSWWVNGKEVHSGVCTDPQAYKESNYSYCLSSRLRVSATFWHNPRNHFRCQV* |

TABLE 7-continued

| TCR Name | Amino acid sequence encoded by TCR Expression Cassette |
|---|---|
| | *QFHGLSEEDKWPEGSPKPVTQNISAEAWGRADCGITSASYQQGVLSATILYEILLGKATLYAVLVSTLVVMAMVKRKNS***RAKRSGSGATNFSLLKQAGDVEENPGP**MHKSLRVLLVILWLQLSWVWSQQKEVEQDPGPLSVPEGAIVSLNCTYSNSAFQYFMWYRQYSRKGPELLMYTYSSGNKEDGRFTAQVDKSSKYISLFIRDSQPSDSATYLCAGGSYGKLTFGQGTILTVHP*NIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSS* (SEQ ID NO: 20) |
| 4386-F | MACRLLCCAVLCLLGAVPMETGVTQTPRHLVMGMTNKKSLKCEQHLGHNAMYWYKQSAKKPLELMFVYSLEERVENNSVPSRFSPECPNSSHLFLHLHTLQPEDSALYLCASSRVEGSDTQYFGPGTRLTVL*EDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNS***RAKRSGSGATNFSLLKQAGDVEENPGP**MHGIRALFMYLWLQLDWVSRGESVGLHLPTLSVQEGDNSIINCAYSNSASDYFIWYKQESGKGPQFIIDIRSNMDKRQGQRVTVLLNKTVKHLSLQIAATQPGDSAVYFCAEKSTGNQFYFGTGTSLTVIP*NIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSS* (SEQ ID NO: 39) |
| 4386-G | MALLLLLLGPGSGLGAVVSQHPSRVICKSGTSVKIECRSLDFQATTMFWY |

TABLE 7-continued

| TCR Name | Amino acid sequence encoded by TCR Expression Cassette |
|---|---|
| | RQFPKQSLMLMATSNEGSKATYEQGVEKDKFLINHASLTLSTLTVTSAHPEDSSFYICSAIRDRSGGETQYFGPGTRLLVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNSRAKRSGSGATNFSLLKQAGDVEENPGPMHSAPISMLAMLFTLSGLRAQSVAQPEDQVNVAEGNPLTVKCTYSVSGNPYLFWYVQYPNRGLQFLLKYITGDNLVKGSYGFEAEFNKSQTSFHLKKPSALVSDSALYFCAVRDPTVSGTYKYIFGTGTRLKVLANIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSS (SEQ ID NO: 58) |
| 4386-H | MATRLLFWVAFCLLGADHTGAGVSQSPSNKVTEKGKDVELRCDPISGHTALYWYRQSLGQGLEFLIYFQGNSAPDKSGLPSDRFSAERTGGSVSTLTIQRTQQEDSAVYLCASSLGGSSETQYFGPGTRLLVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNSRAKRSGSGATNFSLLKQAGDVEENPGPMHKILGASFLVLWLQLCWVSGQQKEKSDQQQVKQSPQSLIVQKGGISIINCAYENTAFDYFPWYQQFPGKGPALLIAIRPDVSEKKEGRFTISFNKSAKQFSLHIMDSQPGDSATYFCAAKRQGGSEKLVFGKGTKLTVNPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSS (SEQ ID NO: 77) |
| 4386-O | MATRLLCWAALCLLGADHTGAGVSQTPSNKVTEKGKYVELRCDPISGHTALYWYRQSLGQGPEFLIYFQGTGAADDSGLPNDRFFAVRPEGSVSTLKIQRTERGDSAVYLCASSPGGSQETQYFGPGTRLLVLEDLRNVTPPKVSLFEPSKAEIANKQKATLVCLARGFFPDHVELSWWVNGKEVHSGVCTDPQAYKESNYSYCLSSRLRVSATFWHNPRNHFRCQVQFHGLSEEDKWPEGSPKPVTQNISAEAWGRADCGITSASYQQGVLSATILYEILLGKATLYAVLVSTLVVMAMVKRKNSRAKRSGSGATNFSLLKQAGDVEENPGPMHGIRALFMYLWLQLDWVSRGESVGLHLPTLSVQEGDNSIINCAYSNSASDYFIWYKQESGKGPQFIIDIRSNMDKRQGQRVTVLLNKTVKHLSLQIAATQPGDSAVYFCAEKRRGGSEKLVFGKGTKLTVNPNIQNPEPAVYQLKDPRSQDSTLCLFTDFDSQINVPKTMESGTFITDKCVLDMKAMDSKSNGAIAWSNQTSFTCQDIFKETNATYPSSDVPCDATLTEKSFETDMNLNFQNLLVIVLRILLLKVAGFNLLMTLRLWSS (SEQ ID NO: 96) |

Example 6

This example demonstrates the avidity of the anti-p53-Y220C TCR expressed by the retroviral vector of Example 5.

Figure 3A:
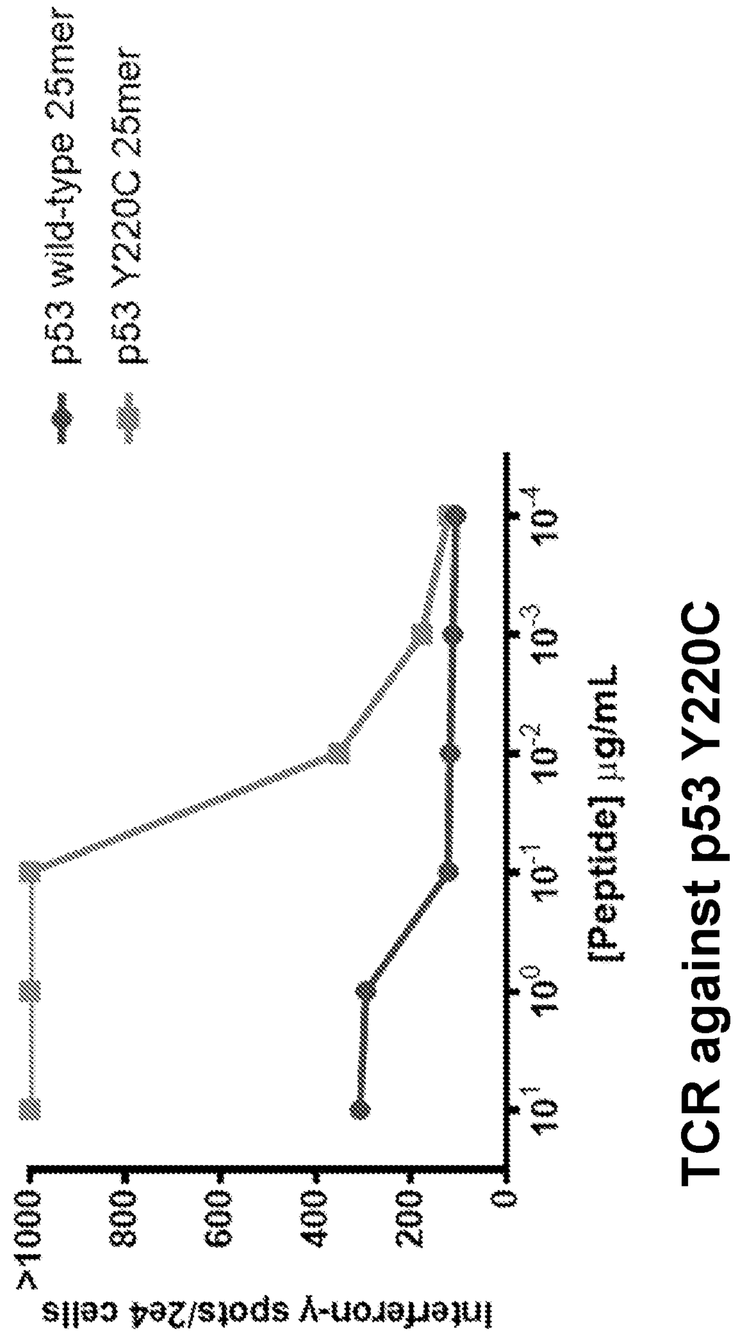
FIG. 3A is a graph showing IFN-γ secretion (number of spots/2e4 cells) measured following co-culture of target cells with effector cells. The effector cells were T cells transduced with the 4343-D TCR. The target cells were autologous DCs pulsed with p53-Y220C 25-mer peptide (squares) or the corresponding WT 25-mer peptide (circles) at the concentrations (μg/mL) shown.

Allogeneic PBL were independently transduced with the retroviral vector encoding the 4343-D TCR of Example 5. Autologous DCs were pulsed for two hours with the mutated p53-Y220C 25-mer peptide DRNTFRHSVVVPCEPPEVGSDCTTI (SEQ ID NO: 115) or the corresponding WT 25-mer peptide DRNTFRHSVVVPYEPPEVGSDCTTI (SEQ ID NO: 114) at one of the various concentrations shown in FIG. 3A. The cells were washed twice and co-cultured for 16 hours with transduced T cells at a ratio of 1:1. IFN-γ secretion was measured by ELISpot assay. As shown in FIG. 3A, the TCR-transduced cells demonstrated specific and avid recognition of the DC pulsed with the p53-Y220C 25-mer peptide.

Without being bound to a particular theory or mechanism, it is believed that the cysteine residues present in the WT 25-mer peptide (SEQ ID NO: 114) and the mutated p53 Y220C 25-mer peptide (SEQ ID NO: 115) may be susceptible to oxidation and homo-dimerization, which may eventually lead to reduced T cell potency (Sachs et al, *J Immunol.,* 205(2):539-549 (2020)). The Y220C mutation itself introduces an additional cysteine residue. It was hypothesized that the additional cysteine residue may affect the TCR's recognition of the mutant peptide.

This hypothesis was tested by modifying all of the cysteine residues in the original sequences of both the wild-type and mutant peptides into AABA, which no longer is susceptible to oxidation or dimerization. The modified peptides are shown in Table 8.

TABLE 8

| | | |
|---|---|---|
| Wild-type 25-mer with AABA substitution | **DRNTFRHSVVVPYEPPEVGSDXTTI** X at position 22 is AABA | SEQ ID NO: 150 |
| Mutated 25-mer with AABA substitutions | **DRNTFRHSVVVPXEPPEVGSDXTTI** X at position 13 is AABA X at position 22 is AABA | SEQ ID NO: 151 |

Allogeneic PBL were independently transduced with the retroviral vector encoding the 4343-D TCR of Example 5. Autologous B cells were pulsed for two hours with the mutated p53-Y220C 25-mer peptide with AABA substitutions (SEQ ID NO: 151) or the corresponding WT 25-mer peptide with AABA substitution (SEQ ID NO: 150) at one of the various concentrations shown in FIGS. 3B-3C. The cells were washed twice and co-cultured for 16 hours with transduced T cells at a ratio of 1:1. Reactivity was tested by measuring the upregulation of the T cell activation marker 4-1BB in murine TCR constant region positive cells by flow cytometry.

Figure 3B:
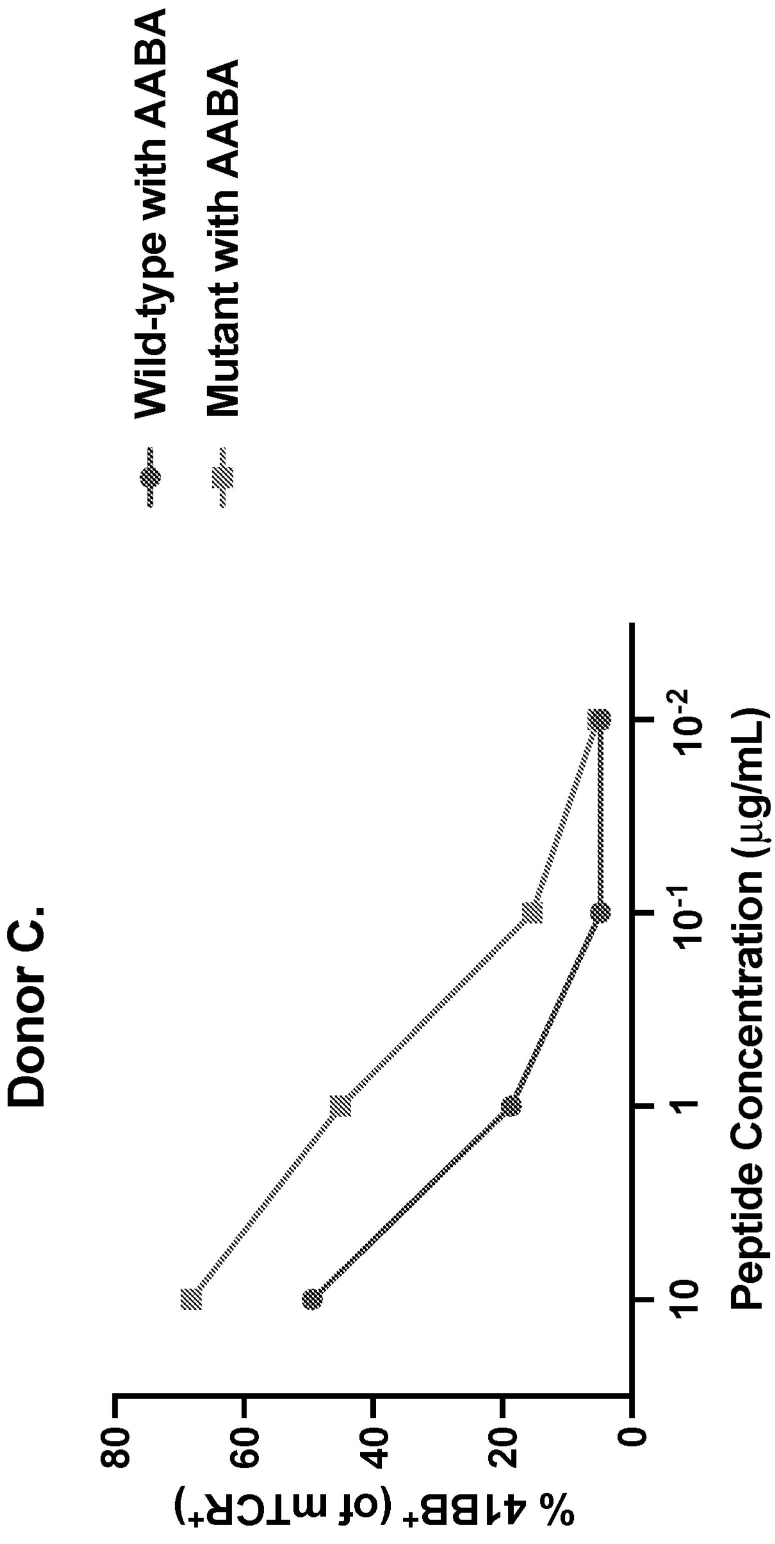
FIGS. 3B-3C are graphs showing the percentage of murine TCR constant region positive cells expressing 4-1BB following co-culture of target cells with effector cells. The effector cells were T cells from Donor C (3B) or Donor H (3C) transduced with the 4343-D TCR. The target cells were autologous B cells pulsed with the mutated p53-Y220C 25-mer peptide with alpha-aminobutyric acid (AABA) substitutions (squares) over the corresponding WT 25-mer peptide with AABA substitution (circles) at the concentrations (μg/mL) shown.
Figure 3C:
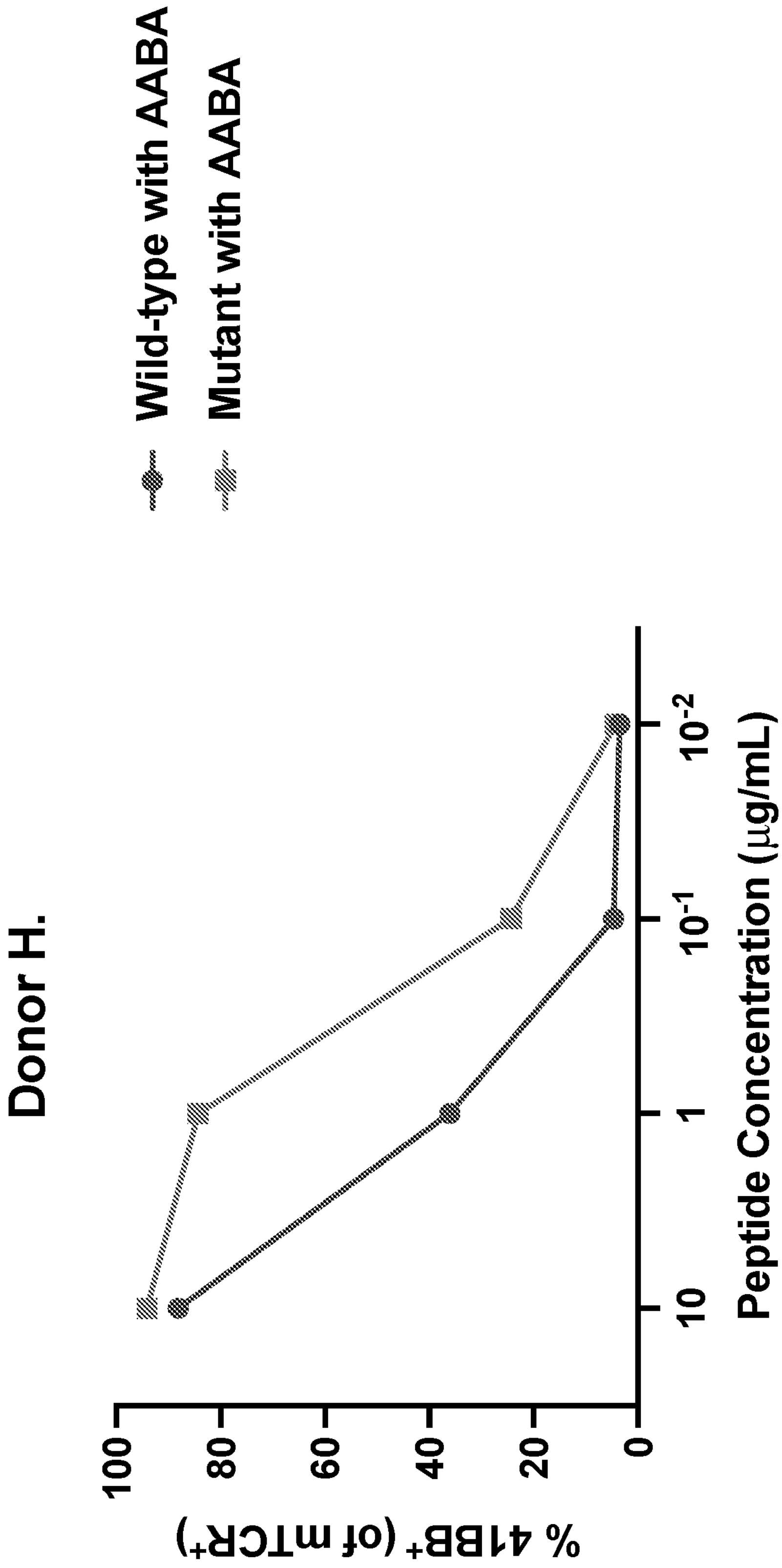
Figure 3D:
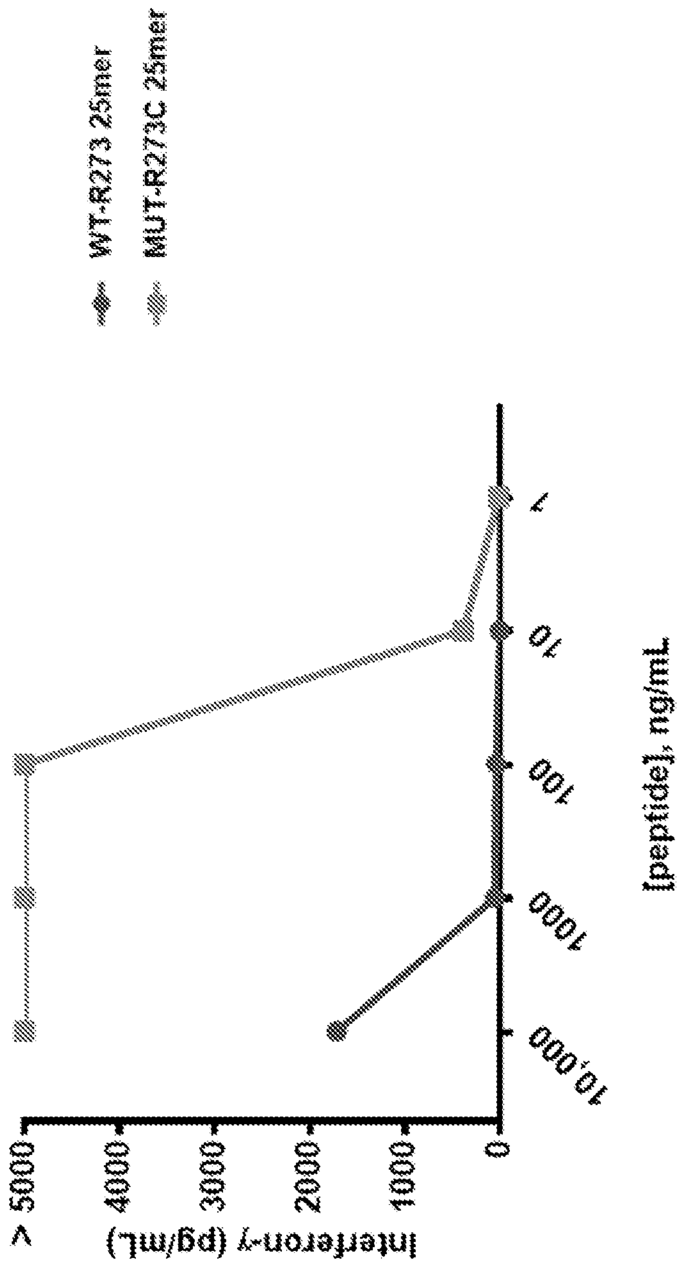
FIGS. 3D-3G are graphs showing IFN-γ secretion (pg/mL) measured following co-culture of target cells with effector cells. The effector cells were T cells independently transduced with the 4386-F TCR (FIG. 3D), the 4386-G TCR (FIG. 3E), the 4386-H TCR (FIG. 3F), or the 4386-O TCR (FIG. 3G). The target cells were autologous DCs pulsed with p53-R273C 25-mer peptide (squares) or the corresponding WT 25-mer peptide (circles) at the concentrations (ng/mL) shown.
Figure 3E:
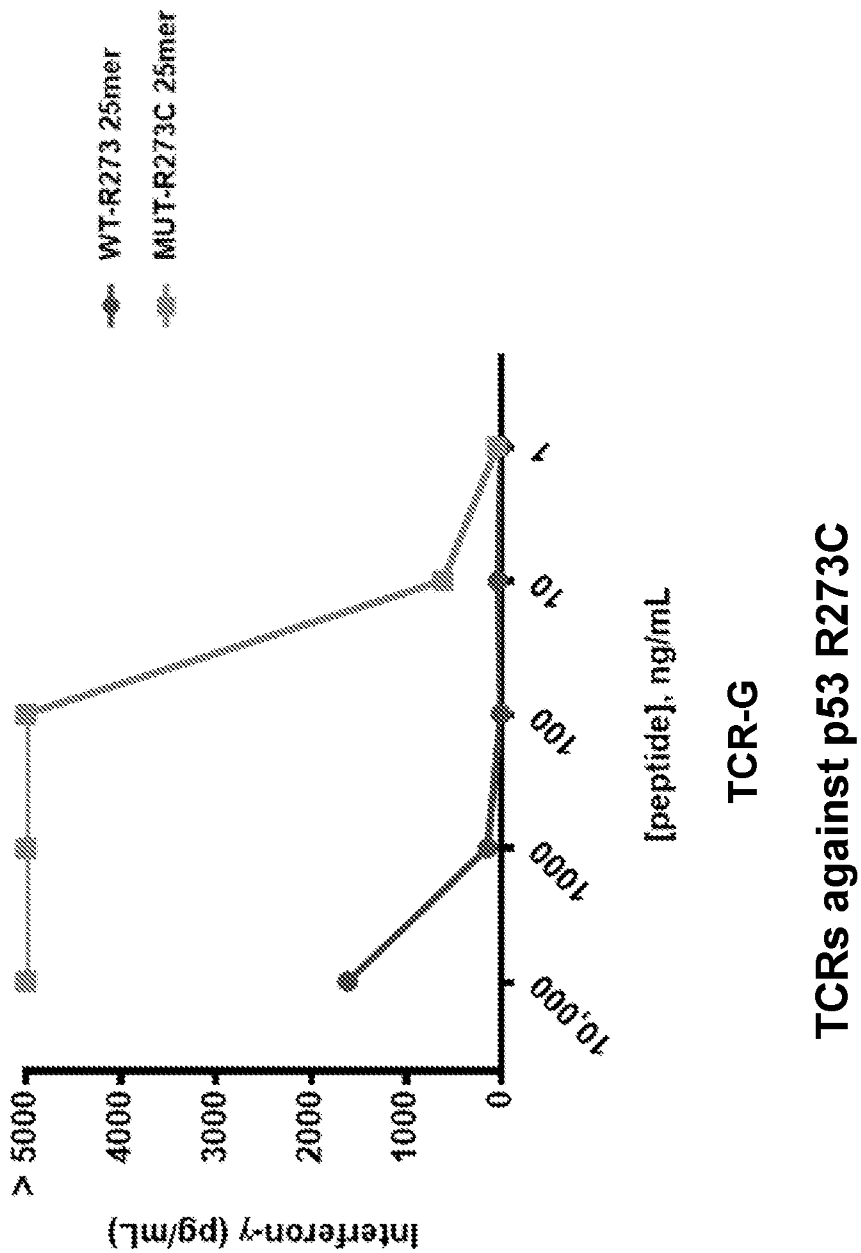
Figure 3F:
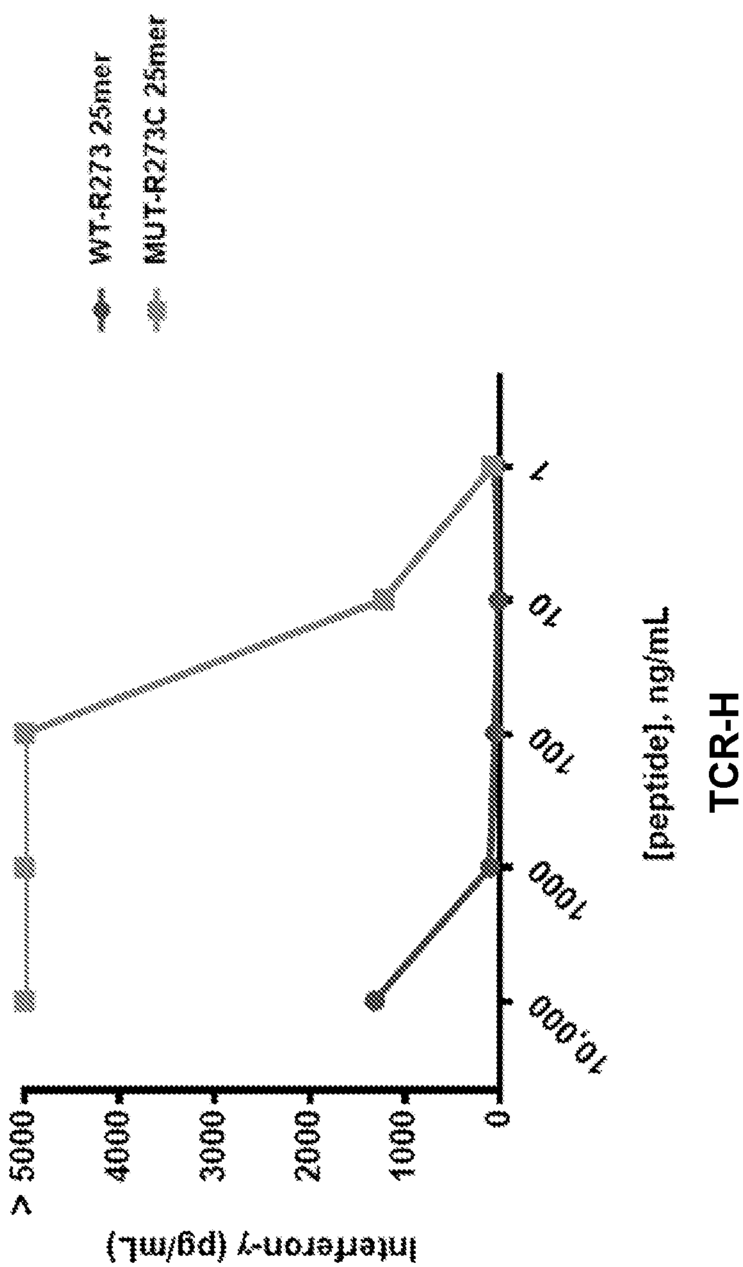
Figure 3G:
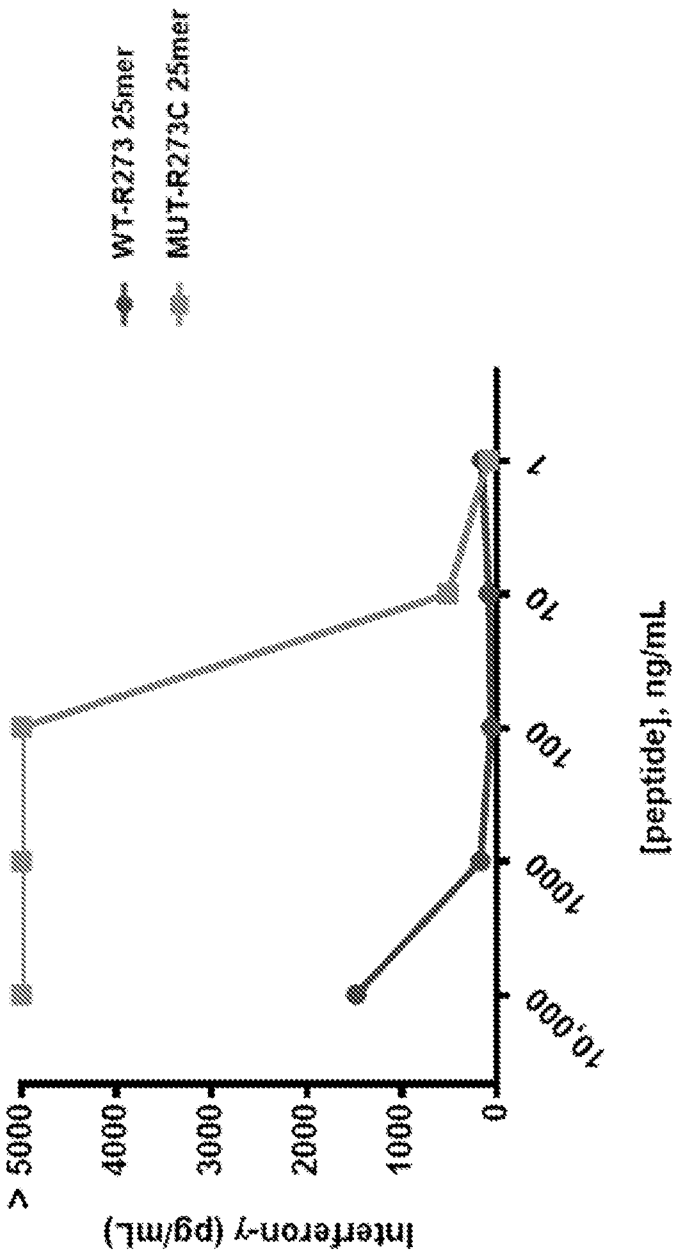

As shown in FIGS. 3B-3C, the results validated the hypothesis described above in this Example. A log or greater TCR potency was observed with the mutated p53-Y220C 25-mer peptide with AABA substitutions over the corresponding WT 25-mer peptide with AABA substitution.

Example 7

This example demonstrates the avidity of the anti-p53-R273C TCRs expressed by the retroviral vectors of Example 5.

Allogeneic PBL were independently transduced with the retroviral vector encoding the 4386-F TCR, 4386-G TCR, 4386-H TCR, or 4386-O TCR of Example 5. Autologous DCs were pulsed for two hours with the p53-R273C 25-mer peptide SGNLLGRNSFEVCVCACPGRDRRTE (SEQ ID NO: 117) or the corresponding WT 25-mer peptide SGNLLGRNSFEVRVCACPGRDRRTE (SEQ ID NO: 116) at one of the various concentrations shown in FIGS. 3D-3G. The cells were washed twice and co-cultured for 16 hours with transduced T cells at a ratio of 1:1. IFN-γ secretion was measured by ELISA (FIGS. 3D-3G). As shown in FIGS. 3D-3G, the TCR-transduced cells demonstrated specific and avid recognition of the DC pulsed with the mutated p53-R273C 25-mer peptide.

Example 8

This example demonstrates that the anti-p53-Y220C TCR expressed by the retroviral vector of Example 5 recognizes mutated p53 presented by an HLA-DRB3*02/HLA-DRA1*01 heterodimer.

Figure 2A:
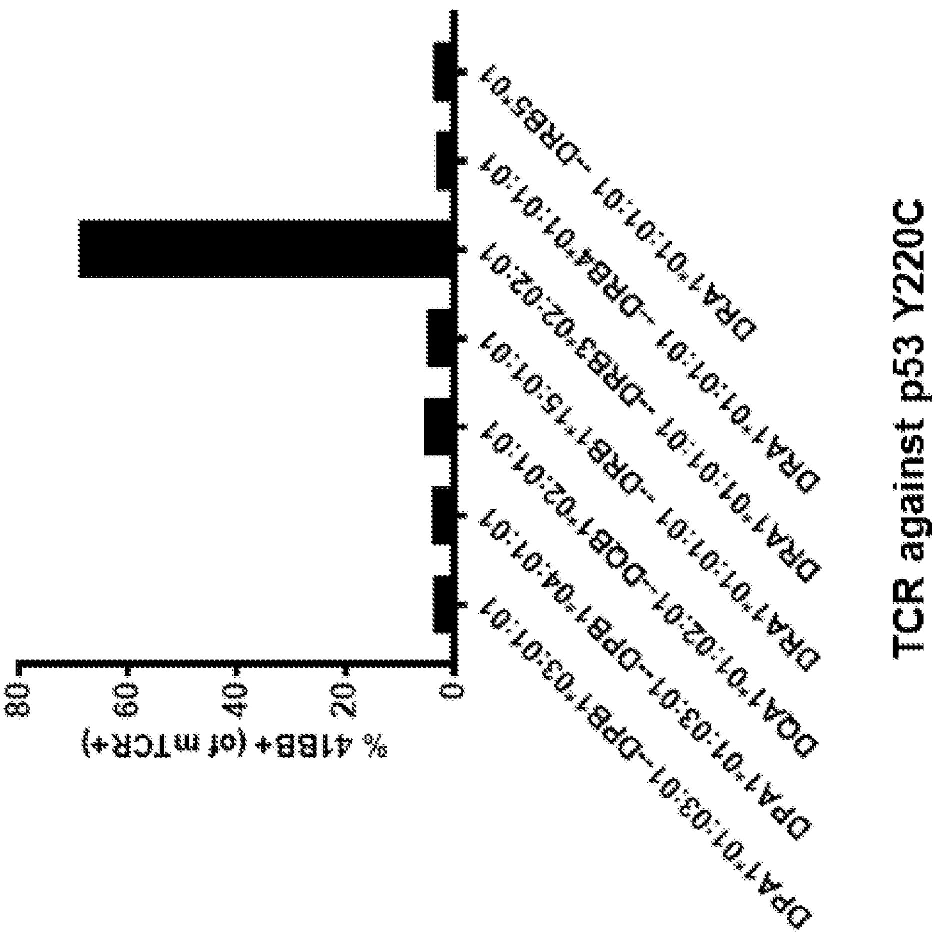
FIG. 2A is a graph showing the percentage of murine TCR constant region positive cells expressing 4-1BB upon co-culture of target cells with effector cells. The effector cells were transduced with the 4343-D TCR. The target cells were COS7 cells transfected with one of the HLA Class II heterodimers shown and pulsed with the p53-Y220C 25-mer peptide.

The MHC Class II molecules expressed by Patient 4343 were determined using exome and mRNA sequencing. The expressed MHC Class II molecules are shown in FIG. 2A.

Effector cells were allogeneic PBL transduced with the retroviral vector of Example 5 encoding the 4343-D TCR. Target cells were COS7 cells independently transfected with one of the HLA Class II heterodimers shown in FIG. 2A and pulsed with the p53-Y220C 25-mer peptide DRNTFRHSVVVPCEPPEVGSDCTTI (SEQ ID NO: 115).

Reactivity was tested by measuring the upregulation of the T cell activation marker 4-1BB in murine TCR constant region positive cells by flow cytometry. The results are shown in FIG. 2A. As shown in FIG. 2A, reactivity was observed only upon co-culture of the 4343-D TCR-transduced cells with the p53-Y220C 25-mer-loaded target cells which had been transduced with a nucleotide sequence encoding an HLA-DRA1*01:01:01/HLA-DRB3*02:02:01 heterodimer.

Example 9

This example demonstrates that the TIL of Example 2 recognized mutated p53 presented by an HLA-DPB1*04:02/HLA-DPA1*01 heterodimer.

Figure 2B:
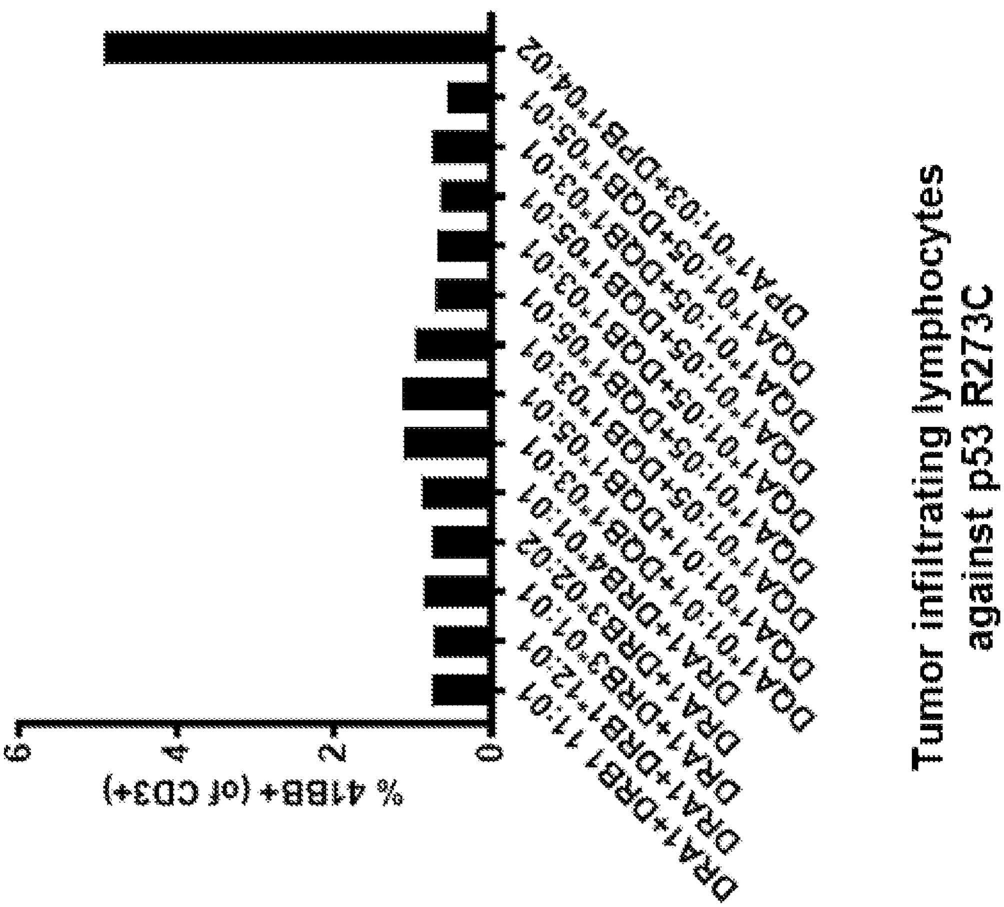
FIG. 2B is a graph showing the percentage of CD3 positive cells expressing 4-1BB upon co-culture of target cells with effector cells. The effector cells were TIL that contain T cells recognizing p53-R273C. The target cells were COS7 cells transfected with one of the HLA Class II heterodimers shown and pulsed with the p53-R273C 25-mer peptide.

The MHC Class II molecules expressed by Patient 4386 were determined using exome and mRNA sequencing. The expressed MHC Class II molecules are shown in FIG. 2B.

Effector cells were TIL that contain T cells recognizing p53-R273C identified in Example 2. Target cells were COS7 cells independently transfected with one of the HLA Class II heterodimers shown in FIG. 2B and pulsed with the p53-R273C 25-mer peptide SGNLLGRNSFEVCVCACPGRDRRTE (SEQ ID NO: 117).

Reactivity was tested by measuring the upregulation of the T cell activation marker 4-1BB in CD3 positive cells by flow cytometry. The results are shown in FIG. 2B. As shown in FIG. 2B, reactivity was observed only upon co-culture of the TIL with the p53-R273C 25-mer-loaded target cells which had been transduced with a nucleotide sequence encoding an HLA-DPA1*01:03/HLA-DPB1*04:02 heterodimer.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified nucleic acid comprising a nucleotide sequence encoding a T cell receptor (TCR) having antigenic specificity for a human $p53^{R273C}$ amino acid sequence, wherein the TCR comprises the amino acid sequences of all of SEQ ID NOs: 59-64.

2. An isolated or purified nucleic acid comprising a nucleotide sequence encoding a polypeptide, wherein the polypeptide comprises the amino acid sequences of all of SEQ ID NOs: 59-64.

3. An isolated or purified nucleic acid comprising a nucleotide sequence encoding a protein comprising a first polypeptide chain comprising the amino acid sequences of all of SEQ ID NOs: 59-61 and a second polypeptide chain comprising the amino acid sequences of all of SEQ ID NOs: 62-64.

4. An isolated or purified nucleic acid comprising, from 5' to 3', a first nucleotide sequence and a second nucleotide sequence, wherein the first and second nucleotide sequence, respectively, encode the amino sequences of SEQ ID NOs: 65 and 66; 66 and 65; 67 and 68; 68 and 67; 69 and 70; 70 and 69; 69 and 68; 68 and 69; 133 and 70; 70 and 133; 133 and 134; 134 and 133; 65 and 132; 132 and 65; 131 and 66; 66 and 131; 131 and 132; 132 and 131; 71 and 72; 72 and 71; 73 and 74; 74 and 73; 75 and 76; or 76 and 75.

5. The isolated or purified nucleic acid of claim 4, further comprising a third nucleotide sequence interposed between the first and second nucleotide sequence, wherein the third nucleotide sequence encodes a cleavable linker peptide.

6. The isolated or purified nucleic acid of claim 5, wherein the cleavable linker peptide comprises the amino acid sequence of (SEQ ID NO: 100)
RAKRSGSGATNFSLLKQAGDVEENPGP.

7. The isolated or purified nucleic acid of claim 6, which encodes an amino acid sequence of SEQ ID NO: 77.

8. A recombinant expression vector comprising the nucleic acid of claim 1.

9. The recombinant expression vector of claim 8, which is a transposon or a lentiviral vector.

10. A method of producing a host cell expressing a TCR that has antigenic specificity for the peptide of SGNLLGRNSFEVCVCACPGRDRRTE (SEQ ID NO: 117), the method comprising contacting a cell with the vector of claim 8 under conditions that allow introduction of the vector into the cell.

11. An isolated or purified host cell comprising the nucleic acid of claim 1.

12. The host cell of claim 11, wherein the cell is a human lymphocyte.

13. The host cell of claim 11, wherein the cell is selected from the group consisting of a T cell, a natural killer T (NKT) cell, an invariant natural killer T (iNKT) cell, and a natural killer (NK) cell.

14. An isolated or purified population of cells comprising the host cell of claim 11.

15. A method of producing a TCR, the method comprising culturing the host cell of claim 11 so that the TCR is produced.

16. A pharmaceutical composition comprising (a) the population of cells of claim 14 and (b) a pharmaceutically acceptable carrier.

* * * * *

SEQUENCE LISTING

<160> NUMBER OF SEQ ID NOS: 151

<210> SEQ ID NO 1
<211> LENGTH: 393
<212> TYPE: PRT
<213> ORGANISM: Homo sapiens

<400> SEQUENCE: 1

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365
```

```
Leu Lys Ser Lys Lys Gly Gln Ser Thr Ser Arg His Lys Lys Leu Met
    370                 375                 380

Phe Lys Thr Glu Gly Pro Asp Ser Asp
385                 390


<210> SEQ ID NO 2
<211> LENGTH: 6
<212> TYPE: PRT
<213> ORGANISM: Homo sapiens

<400> SEQUENCE: 2

Asn Ser Ala Phe Gln Tyr
1               5


<210> SEQ ID NO 3
<211> LENGTH: 6
<212> TYPE: PRT
<213> ORGANISM: Homo sapiens

<400> SEQUENCE: 3

Thr Tyr Ser Ser Gly Asn
1               5


<210> SEQ ID NO 4
<211> LENGTH: 11
<212> TYPE: PRT
<213> ORGANISM: Homo sapiens

<400> SEQUENCE: 4

Cys Ala Gly Gly Ser Tyr Gly Lys Leu Thr Phe
1               5                   10


<210> SEQ ID NO 5
<211> LENGTH: 5
<212> TYPE: PRT
<213> ORGANISM: Homo sapiens

<400> SEQUENCE: 5

Met Asn His Glu Tyr
1               5


<210> SEQ ID NO 6
<211> LENGTH: 6
<212> TYPE: PRT
<213> ORGANISM: Homo sapiens

<400> SEQUENCE: 6

Ser Met Asn Val Glu Val
1               5


<210> SEQ ID NO 7
<211> LENGTH: 13
<212> TYPE: PRT
<213> ORGANISM: Homo sapiens

<400> SEQUENCE: 7

Cys Ala Ser Ser Phe Ile Ser Asn Gln Pro Gln His Phe
1               5                   10


<210> SEQ ID NO 8
<211> LENGTH: 110
<212> TYPE: PRT
<213> ORGANISM: Homo sapiens

<400> SEQUENCE: 8
```

-continued

Gln Gln Lys Glu Val Glu Gln Asp Pro Gly Pro Leu Ser Val Pro Glu
1               5                   10                  15

Gly Ala Ile Val Ser Leu Asn Cys Thr Tyr Ser Asn Ser Ala Phe Gln
            20                  25                  30

Tyr Phe Met Trp Tyr Arg Gln Tyr Ser Arg Lys Gly Pro Glu Leu Leu
        35                  40                  45

Met Tyr Thr Tyr Ser Ser Gly Asn Lys Glu Asp Gly Arg Phe Thr Ala
    50                  55                  60

Gln Val Asp Lys Ser Ser Lys Tyr Ile Ser Leu Phe Ile Arg Asp Ser
65                  70                  75                  80

Gln Pro Ser Asp Ser Ala Thr Tyr Leu Cys Ala Gly Gly Ser Tyr Gly
                85                  90                  95

Lys Leu Thr Phe Gly Gln Gly Thr Ile Leu Thr Val His Pro
            100                 105                 110

<210> SEQ ID NO 9
<211> LENGTH: 110
<212> TYPE: PRT
<213> ORGANISM: Homo sapiens

<400> SEQUENCE: 9

Gln Val Thr Gln Asn Pro Arg Tyr Leu Ile Thr Val Thr Gly Lys Lys
1               5                   10                  15

Leu Thr Val Thr Cys Ser Gln Asn Met Asn His Glu Tyr Met Ser Trp
            20                  25                  30

Tyr Arg Gln Asp Pro Gly Leu Gly Leu Arg Gln Ile Tyr Tyr Ser Met
        35                  40                  45

Asn Val Glu Val Thr Asp Lys Gly Asp Val Pro Glu Gly Tyr Lys Val
    50                  55                  60

Ser Arg Lys Glu Lys Arg Asn Phe Pro Leu Ile Leu Glu Ser Pro Ser
65                  70                  75                  80

Pro Asn Gln Thr Ser Leu Tyr Phe Cys Ala Ser Ser Phe Ile Ser Asn
                85                  90                  95

Gln Pro Gln His Phe Gly Asp Gly Thr Arg Leu Ser Ile Leu
            100                 105                 110

<210> SEQ ID NO 10
<211> LENGTH: 131
<212> TYPE: PRT
<213> ORGANISM: Artificial Sequence
<220> FEATURE:
<223> OTHER INFORMATION: Synthetic

<400> SEQUENCE: 10

Met His Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

-continued

```
Phe Ile Arg Asp Ser Gln Pro Ser Asp Ser Ala Thr Tyr Leu Cys Ala
            100                 105                 110

Gly Gly Ser Tyr Gly Lys Leu Thr Phe Gly Gln Gly Thr Ile Leu Thr
        115                 120                 125

Val His Pro
    130


<210> SEQ ID NO 11
<211> LENGTH: 131
<212> TYPE: PRT
<213> ORGANISM: Artificial Sequence
<220> FEATURE:
<223> OTHER INFORMATION: Synthetic

<400> SEQUENCE: 11

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Phe Ile Ser Asn Gln Pro Gln His Phe Gly Asp Gly Thr Arg Leu
        115                 120                 125

Ser Ile Leu
    130


<210> SEQ ID NO 12
<211> LENGTH: 131
<212> TYPE: PRT
<213> ORGANISM: Homo sapiens

<400> SEQUENCE: 12

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Gly Gly Ser Tyr Gly Lys Leu Thr Phe Gly Gln Gly Thr Ile Leu Thr
        115                 120                 125

Val His Pro
```

130

<210> SEQ ID NO 13
<211> LENGTH: 131
<212> TYPE: PRT
<213> ORGANISM: Homo sapiens

<400> SEQUENCE: 13

```
Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Phe Ile Ser Asn Gln Pro Gln His Phe Gly Asp Gly Thr Arg Leu
        115                 120                 125

Ser Ile Leu
    130
```

<210> SEQ ID NO 14
<211> LENGTH: 268
<212> TYPE: PRT
<213> ORGANISM: Artificial Sequence
<220> FEATURE:
<223> OTHER INFORMATION: Synthetic

<400> SEQUENCE: 14

```
Met His Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Gly Gly Ser Tyr Gly Lys Leu Thr Phe Gly Gln Gly Thr Ile Leu Thr
        115                 120                 125

Val His Pro Asn Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175
```

-continued

Asp Lys Cys Val Leu Asp Met Lys Ala Met Asp Ser Lys Ser Asn Gly
180 185 190

Ala Ile Ala Trp Ser Asn Gln Thr Ser Phe Thr Cys Gln Asp Ile Phe
195 200 205

Lys Glu Thr Asn Ala Thr Tyr Pro Ser Ser Asp Val Pro Cys Asp Ala
210 215 220

Thr Leu Thr Glu Lys Ser Phe Glu Thr Asp Met Asn Leu Asn Phe Gln
225 230 235 240

Asn Leu Leu Val Ile Val Leu Arg Ile Leu Leu Leu Lys Val Ala Gly
245 250 255

Phe Asn Leu Leu Met Thr Leu Arg Leu Trp Ser Ser
260 265

<210> SEQ ID NO 15
<211> LENGTH: 304
<212> TYPE: PRT
<213> ORGANISM: Artificial Sequence
<220> FEATURE:
<223> OTHER INFORMATION: Synthetic

<400> SEQUENCE: 15

Met Ala Pro Gln Leu Leu Gly Tyr Val Val Leu Cys Leu Leu Gly Ala
1 5 10 15

Gly Pro Leu Glu Ala Gln Val Thr Gln Asn Pro Arg Tyr Leu Ile Thr
20 25 30

Val Thr Gly Lys Lys Leu Thr Val Thr Cys Ser Gln Asn Met Asn His
35 40 45

Glu Tyr Met Ser Trp Tyr Arg Gln Asp Pro Gly Leu Gly Leu Arg Gln
50 55 60

Ile Tyr Tyr Ser Met Asn Val Glu Val Thr Asp Lys Gly Asp Val Pro
65 70 75 80

Glu Gly Tyr Lys Val Ser Arg Lys Glu Lys Arg Asn Phe Pro Leu Ile
85 90 95

Leu Glu Ser Pro Ser Pro Asn Gln Thr Ser Leu Tyr Phe Cys Ala Ser
100 105 110

Ser Phe Ile Ser Asn Gln Pro Gln His Phe Gly Asp Gly Thr Arg Leu
115 120 125

Ser Ile Leu Glu Asp Leu Arg Asn Val Thr Pro Pro Lys Val Ser Leu
130 135 140

Phe Glu Pro Ser Lys Ala Glu Ile Ala Asn Lys Gln Lys Ala Thr Leu
145 150 155 160

Val Cys Leu Ala Arg Gly Phe Phe Pro Asp His Val Glu Leu Ser Trp
165 170 175

Trp Val Asn Gly Lys Glu Val His Ser Gly Val Cys Thr Asp Pro Gln
180 185 190

Ala Tyr Lys Glu Ser Asn Tyr Ser Tyr Cys Leu Ser Ser Arg Leu Arg
195 200 205

Val Ser Ala Thr Phe Trp His Asn Pro Arg Asn His Phe Arg Cys Gln
210 215 220

Val Gln Phe His Gly Leu Ser Glu Glu Asp Lys Trp Pro Glu Gly Ser
225 230 235 240

Pro Lys Pro Val Thr Gln Asn Ile Ser Ala Glu Ala Trp Gly Arg Ala
245 250 255

Asp Cys Gly Ile Thr Ser Ala Ser Tyr Gln Gln Gly Val Leu Ser Ala
260 265 270

```
Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300


<210> SEQ ID NO 16
<211> LENGTH: 268
<212> TYPE: PRT
<213> ORGANISM: Artificial Sequence
<220> FEATURE:
<223> OTHER INFORMATION: Synthetic

<400> SEQUENCE: 16

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Gly Gly Ser Tyr Gly Lys Leu Thr Phe Gly Gln Gly Thr Ile Leu Thr
        115                 120                 125

Val His Pro Asn Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Cys Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Leu Val Ile Val Leu Arg Ile Leu Leu Leu Lys Val Ala Gly
                245                 250                 255

Phe Asn Leu Leu Met Thr Leu Arg Leu Trp Ser Ser
            260                 265


<210> SEQ ID NO 17
<211> LENGTH: 304
<212> TYPE: PRT
<213> ORGANISM: Artificial Sequence
<220> FEATURE:
<223> OTHER INFORMATION: Synthetic

<400> SEQUENCE: 17

Met Gly Pro Gln Leu Leu Gly Tyr Val Val Leu Cys Leu Leu Gly Ala
```

-continued

```
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Phe Ile Ser Asn Gln Pro Gln His Phe Gly Asp Gly Thr Arg Leu
        115                 120                 125

Ser Ile Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300


<210> SEQ ID NO 18
<211> LENGTH: 247
<212> TYPE: PRT
<213> ORGANISM: Artificial Sequence
<220> FEATURE:
<223> OTHER INFORMATION: Synthetic

<400> SEQUENCE: 18

Gln Gln Lys Glu Val Glu Gln Asp Pro Gly Pro Leu Ser Val Pro Glu
1               5                   10                  15

Gly Ala Ile Val Ser Leu Asn Cys Thr Tyr Ser Asn Ser Ala Phe Gln
            20                  25                  30

Tyr Phe Met Trp Tyr Arg Gln Tyr Ser Arg Lys Gly Pro Glu Leu Leu
        35                  40                  45

Met Tyr Thr Tyr Ser Ser Gly Asn Lys Glu Asp Gly Arg Phe Thr Ala
    50                  55                  60

Gln Val Asp Lys Ser Ser Lys Tyr Ile Ser Leu Phe Ile Arg Asp Ser
```

```
65                  70                  75                  80

Gln Pro Ser Asp Ser Ala Thr Tyr Leu Cys Ala Gly Gly Ser Tyr Gly
                85                  90                  95

Lys Leu Thr Phe Gly Gln Gly Thr Ile Leu Thr Val His Pro Asn Ile
            100                 105                 110

Gln Asn Pro Glu Pro Ala Val Tyr Gln Leu Lys Asp Pro Arg Ser Gln
        115                 120                 125

Asp Ser Thr Leu Cys Leu Phe Thr Asp Phe Asp Ser Gln Ile Asn Val
    130                 135                 140

Pro Lys Thr Met Glu Ser Gly Thr Phe Ile Thr Asp Lys Cys Val Leu
145                 150                 155                 160

Asp Met Lys Ala Met Asp Ser Lys Ser Asn Gly Ala Ile Ala Trp Ser
                165                 170                 175

Asn Gln Thr Ser Phe Thr Cys Gln Asp Ile Phe Lys Glu Thr Asn Ala
            180                 185                 190

Thr Tyr Pro Ser Ser Asp Val Pro Cys Asp Ala Thr Leu Thr Glu Lys
        195                 200                 205

Ser Phe Glu Thr Asp Met Asn Leu Asn Phe Gln Asn Leu Leu Val Ile
    210                 215                 220

Val Leu Arg Ile Leu Leu Leu Lys Val Ala Gly Phe Asn Leu Leu Met
225                 230                 235                 240

Thr Leu Arg Leu Trp Ser Ser
                245


<210> SEQ ID NO 19
<211> LENGTH: 283
<212> TYPE: PRT
<213> ORGANISM: Artificial Sequence
<220> FEATURE:
<223> OTHER INFORMATION: Synthetic

<400> SEQUENCE: 19

Gln Val Thr Gln Asn Pro Arg Tyr Leu Ile Thr Val Thr Gly Lys Lys
1               5                   10                  15

Leu Thr Val Thr Cys Ser Gln Asn Met Asn His Glu Tyr Met Ser Trp
            20                  25                  30

Tyr Arg Gln Asp Pro Gly Leu Gly Leu Arg Gln Ile Tyr Tyr Ser Met
        35                  40                  45

Asn Val Glu Val Thr Asp Lys Gly Asp Val Pro Glu Gly Tyr Lys Val
    50                  55                  60

Ser Arg Lys Glu Lys Arg Asn Phe Pro Leu Ile Leu Glu Ser Pro Ser
65                  70                  75                  80

Pro Asn Gln Thr Ser Leu Tyr Phe Cys Ala Ser Ser Phe Ile Ser Asn
                85                  90                  95

Gln Pro Gln His Phe Gly Asp Gly Thr Arg Leu Ser Ile Leu Glu Asp
            100                 105                 110

Leu Arg Asn Val Thr Pro Pro Lys Val Ser Leu Phe Glu Pro Ser Lys
        115                 120                 125

Ala Glu Ile Ala Asn Lys Gln Lys Ala Thr Leu Val Cys Leu Ala Arg
    130                 135                 140

Gly Phe Phe Pro Asp His Val Glu Leu Ser Trp Trp Val Asn Gly Lys
145                 150                 155                 160

Glu Val His Ser Gly Val Cys Thr Asp Pro Gln Ala Tyr Lys Glu Ser
                165                 170                 175

Asn Tyr Ser Tyr Cys Leu Ser Ser Arg Leu Arg Val Ser Ala Thr Phe
```

```
            180                 185                 190

Trp His Asn Pro Arg Asn His Phe Arg Cys Gln Val Gln Phe His Gly
        195                 200                 205

Leu Ser Glu Glu Asp Lys Trp Pro Glu Gly Ser Pro Lys Pro Val Thr
    210                 215                 220

Gln Asn Ile Ser Ala Glu Ala Trp Gly Arg Ala Asp Cys Gly Ile Thr
225                 230                 235                 240

Ser Ala Ser Tyr Gln Gln Gly Val Leu Ser Ala Thr Ile Leu Tyr Glu
                245                 250                 255

Ile Leu Leu Gly Lys Ala Thr Leu Tyr Ala Val Leu Val Ser Thr Leu
            260                 265                 270

Val Val Met Ala Met Val Lys Arg Lys Asn Ser
        275                 280


<210> SEQ ID NO 20
<211> LENGTH: 599
<212> TYPE: PRT
<213> ORGANISM: Artificial Sequence
<220> FEATURE:
<223> OTHER INFORMATION: Synthetic

<400> SEQUENCE: 20

Met Ala Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Phe Ile Ser Asn Gln Pro Gln His Phe Gly Asp Gly Thr Arg Leu
        115                 120                 125

Ser Ile Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
```

-continued

```
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300

Arg Ala Lys Arg Ser Gly Ser Gly Ala Thr Asn Phe Ser Leu Leu Lys
305                 310                 315                 320

Gln Ala Gly Asp Val Glu Glu Asn Pro Gly Pro Met His Lys Ser Leu
                325                 330                 335

Arg Val Leu Leu Val Ile Leu Trp Leu Gln Leu Ser Trp Val Trp Ser
            340                 345                 350

Gln Gln Lys Glu Val Glu Gln Asp Pro Gly Pro Leu Ser Val Pro Glu
        355                 360                 365

Gly Ala Ile Val Ser Leu Asn Cys Thr Tyr Ser Asn Ser Ala Phe Gln
    370                 375                 380

Tyr Phe Met Trp Tyr Arg Gln Tyr Ser Arg Lys Gly Pro Glu Leu Leu
385                 390                 395                 400

Met Tyr Thr Tyr Ser Ser Gly Asn Lys Glu Asp Gly Arg Phe Thr Ala
                405                 410                 415

Gln Val Asp Lys Ser Ser Lys Tyr Ile Ser Leu Phe Ile Arg Asp Ser
            420                 425                 430

Gln Pro Ser Asp Ser Ala Thr Tyr Leu Cys Ala Gly Gly Ser Tyr Gly
        435                 440                 445

Lys Leu Thr Phe Gly Gln Gly Thr Ile Leu Thr Val His Pro Asn Ile
    450                 455                 460

Gln Asn Pro Glu Pro Ala Val Tyr Gln Leu Lys Asp Pro Arg Ser Gln
465                 470                 475                 480

Asp Ser Thr Leu Cys Leu Phe Thr Asp Phe Asp Ser Gln Ile Asn Val
                485                 490                 495

Pro Lys Thr Met Glu Ser Gly Thr Phe Ile Thr Asp Lys Cys Val Leu
            500                 505                 510

Asp Met Lys Ala Met Asp Ser Lys Ser Asn Gly Ala Ile Ala Trp Ser
        515                 520                 525

Asn Gln Thr Ser Phe Thr Cys Gln Asp Ile Phe Lys Glu Thr Asn Ala
    530                 535                 540

Thr Tyr Pro Ser Ser Asp Val Pro Cys Asp Ala Thr Leu Thr Glu Lys
545                 550                 555                 560

Ser Phe Glu Thr Asp Met Asn Leu Asn Phe Gln Asn Leu Leu Val Ile
                565                 570                 575

Val Leu Arg Ile Leu Leu Leu Lys Val Ala Gly Phe Asn Leu Leu Met
            580                 585                 590

Thr Leu Arg Leu Trp Ser Ser
        595


<210> SEQ ID NO 21
<211> LENGTH: 6
<212> TYPE: PRT
<213> ORGANISM: Homo sapiens

<400> SEQUENCE: 21

Asn Ser Ala Ser Asp Tyr
1               5


<210> SEQ ID NO 22
<211> LENGTH: 7
```

<212> TYPE: PRT
<213> ORGANISM: Homo sapiens

<400> SEQUENCE: 22

Ile Arg Ser Asn Met Asp Lys
1 5

<210> SEQ ID NO 23
<211> LENGTH: 12
<212> TYPE: PRT
<213> ORGANISM: Homo sapiens

<400> SEQUENCE: 23

Cys Ala Glu Lys Ser Thr Gly Asn Gln Phe Tyr Phe
1 5 10

<210> SEQ ID NO 24
<211> LENGTH: 5
<212> TYPE: PRT
<213> ORGANISM: Homo sapiens

<400> SEQUENCE: 24

Leu Gly His Asn Ala
1 5

<210> SEQ ID NO 25
<211> LENGTH: 6
<212> TYPE: PRT
<213> ORGANISM: Homo sapiens

<400> SEQUENCE: 25

Tyr Ser Leu Glu Glu Arg
1 5

<210> SEQ ID NO 26
<211> LENGTH: 14
<212> TYPE: PRT
<213> ORGANISM: Homo sapiens

<400> SEQUENCE: 26

Cys Ala Ser Ser Arg Val Glu Gly Ser Asp Thr Gln Tyr Phe
1 5 10

<210> SEQ ID NO 27
<211> LENGTH: 110
<212> TYPE: PRT
<213> ORGANISM: Homo sapiens

<400> SEQUENCE: 27

Glu Ser Val Gly Leu His Leu Pro Thr Leu Ser Val Gln Glu Gly Asp
1 5 10 15

Asn Ser Ile Ile Asn Cys Ala Tyr Ser Asn Ser Ala Ser Asp Tyr Phe
20 25 30

Ile Trp Tyr Lys Gln Glu Ser Gly Lys Gly Pro Gln Phe Ile Ile Asp
35 40 45

Ile Arg Ser Asn Met Asp Lys Arg Gln Gly Gln Arg Val Thr Val Leu
50 55 60

Leu Asn Lys Thr Val Lys His Leu Ser Leu Gln Ile Ala Ala Thr Gln
65 70 75 80

Pro Gly Asp Ser Ala Val Tyr Phe Cys Ala Glu Lys Ser Thr Gly Asn
85 90 95

Gln Phe Tyr Phe Gly Thr Gly Thr Ser Leu Thr Val Ile Pro 100 105 110

<210> SEQ ID NO 28
<211> LENGTH: 114
<212> TYPE: PRT
<213> ORGANISM: Homo sapiens

<400> SEQUENCE: 28

Met Glu Thr Gly Val Thr Gln Thr Pro Arg His Leu Val Met Gly Met
1 5 10 15

Thr Asn Lys Lys Ser Leu Lys Cys Glu Gln His Leu Gly His Asn Ala
20 25 30

Met Tyr Trp Tyr Lys Gln Ser Ala Lys Lys Pro Leu Glu Leu Met Phe
35 40 45

Val Tyr Ser Leu Glu Glu Arg Val Glu Asn Asn Ser Val Pro Ser Arg
50 55 60

Phe Ser Pro Glu Cys Pro Asn Ser Ser His Leu Phe Leu His Leu His
65 70 75 80

Thr Leu Gln Pro Glu Asp Ser Ala Leu Tyr Leu Cys Ala Ser Ser Arg
85 90 95

Val Glu Gly Ser Asp Thr Gln Tyr Phe Gly Pro Gly Thr Arg Leu Thr
100 105 110

Val Leu

<210> SEQ ID NO 29
<211> LENGTH: 131
<212> TYPE: PRT
<213> ORGANISM: Artificial Sequence
<220> FEATURE:
<223> OTHER INFORMATION: Synthetic

<400> SEQUENCE: 29

Met His Gly Ile Arg Ala Leu Phe Met Tyr Leu Trp Leu Gln Leu Asp
1 5 10 15

Trp Val Ser Arg Gly Glu Ser Val Gly Leu His Leu Pro Thr Leu Ser
20 25 30

Val Gln Glu Gly Asp Asn Ser Ile Ile Asn Cys Ala Tyr Ser Asn Ser
35 40 45

Ala Ser Asp Tyr Phe Ile Trp Tyr Lys Gln Glu Ser Gly Lys Gly Pro
50 55 60

Gln Phe Ile Ile Asp Ile Arg Ser Asn Met Asp Lys Arg Gln Gly Gln
65 70 75 80

Arg Val Thr Val Leu Leu Asn Lys Thr Val Lys His Leu Ser Leu Gln
85 90 95

Ile Ala Ala Thr Gln Pro Gly Asp Ser Ala Val Tyr Phe Cys Ala Glu
100 105 110

Lys Ser Thr Gly Asn Gln Phe Tyr Phe Gly Thr Gly Thr Ser Leu Thr
115 120 125

Val Ile Pro
130

<210> SEQ ID NO 30
<211> LENGTH: 132
<212> TYPE: PRT
<213> ORGANISM: Artificial Sequence
<220> FEATURE:
<223> OTHER INFORMATION: Synthetic

<400> SEQUENCE: 30

Met Ala Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
            20                  25                  30

Gly Met Thr Asn Lys Lys Ser Leu Lys Cys Glu Gln His Leu Gly His
        35                  40                  45

Asn Ala Met Tyr Trp Tyr Lys Gln Ser Ala Lys Lys Pro Leu Glu Leu
    50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110

Ser Arg Val Glu Gly Ser Asp Thr Gln Tyr Phe Gly Pro Gly Thr Arg
        115                 120                 125

Leu Thr Val Leu
    130

<210> SEQ ID NO 31
<211> LENGTH: 131
<212> TYPE: PRT
<213> ORGANISM: Homo sapiens

<400> SEQUENCE: 31

Met Ala Gly Ile Arg Ala Leu Phe Met Tyr Leu Trp Leu Gln Leu Asp
1               5                   10                  15

Trp Val Ser Arg Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Glu Ser Gly Lys Gly Pro
    50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Lys Ser Thr Gly Asn Gln Phe Tyr Phe Gly Thr Gly Thr Ser Leu Thr
        115                 120                 125

Val Ile Pro
    130

<210> SEQ ID NO 32
<211> LENGTH: 132
<212> TYPE: PRT
<213> ORGANISM: Homo sapiens

<400> SEQUENCE: 32

Met Gly Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
            20                  25                  30

Gly Met Thr Asn Lys Lys Ser Leu Lys Cys Glu Gln His Leu Gly His
        35                  40                  45

```
Asn Ala Met Tyr Trp Tyr Lys Gln Ser Ala Lys Lys Pro Leu Glu Leu
    50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110

Ser Arg Val Glu Gly Ser Asp Thr Gln Tyr Phe Gly Pro Gly Thr Arg
        115                 120                 125

Leu Thr Val Leu
    130


<210> SEQ ID NO 33
<211> LENGTH: 268
<212> TYPE: PRT
<213> ORGANISM: Artificial Sequence
<220> FEATURE:
<223> OTHER INFORMATION: Synthetic

<400> SEQUENCE: 33

Met His Gly Ile Arg Ala Leu Phe Met Tyr Leu Trp Leu Gln Leu Asp
1               5                   10                  15

Trp Val Ser Arg Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Glu Ser Gly Lys Gly Pro
    50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Lys Ser Thr Gly Asn Gln Phe Tyr Phe Gly Thr Gly Thr Ser Leu Thr
        115                 120                 125

Val Ile Pro Asn Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Cys Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Leu Val Ile Val Leu Arg Ile Leu Leu Leu Lys Val Ala Gly
                245                 250                 255

Phe Asn Leu Leu Met Thr Leu Arg Leu Trp Ser Ser
            260                 265
```

<210> SEQ ID NO 34
<211> LENGTH: 305
<212> TYPE: PRT
<213> ORGANISM: Artificial Sequence
<220> FEATURE:
<223> OTHER INFORMATION: Synthetic

<400> SEQUENCE: 34

```
Met Ala Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
            20                  25                  30

Gly Met Thr Asn Lys Lys Ser Leu Lys Cys Glu Gln His Leu Gly His
        35                  40                  45

Asn Ala Met Tyr Trp Tyr Lys Gln Ser Ala Lys Lys Pro Leu Glu Leu
    50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110

Ser Arg Val Glu Gly Ser Asp Thr Gln Tyr Phe Gly Pro Gly Thr Arg
        115                 120                 125

Leu Thr Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305
```

<210> SEQ ID NO 35
<211> LENGTH: 268
<212> TYPE: PRT
<213> ORGANISM: Artificial Sequence
<220> FEATURE:
<223> OTHER INFORMATION: Synthetic

<400> SEQUENCE: 35

```
Met Ala Gly Ile Arg Ala Leu Phe Met Tyr Leu Trp Leu Gln Leu Asp
1               5                   10                  15

Trp Val Ser Arg Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Glu Ser Gly Lys Gly Pro
    50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Lys Ser Thr Gly Asn Gln Phe Tyr Phe Gly Thr Gly Thr Ser Leu Thr
        115                 120                 125

Val Ile Pro Asn Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Cys Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Leu Val Ile Val Leu Arg Ile Leu Leu Leu Lys Val Ala Gly
                245                 250                 255

Phe Asn Leu Leu Met Thr Leu Arg Leu Trp Ser Ser
            260                 265
```

<210> SEQ ID NO 36
<211> LENGTH: 305
<212> TYPE: PRT
<213> ORGANISM: Artificial Sequence
<220> FEATURE:
<223> OTHER INFORMATION: Synthetic

<400> SEQUENCE: 36

```
Met Gly Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
            20                  25                  30

Gly Met Thr Asn Lys Lys Ser Leu Lys Cys Glu Gln His Leu Gly His
        35                  40                  45

Asn Ala Met Tyr Trp Tyr Lys Gln Ser Ala Lys Lys Pro Leu Glu Leu
    50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
```

```
                85                  90                  95

Leu His Thr Leu Gln Pro Glu Asp Ser Ala Leu Tyr Leu Cys Ala Ser
            100                 105                 110

Ser Arg Val Glu Gly Ser Asp Thr Gln Tyr Phe Gly Pro Gly Thr Arg
        115                 120                 125

Leu Thr Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305


<210> SEQ ID NO 37
<211> LENGTH: 247
<212> TYPE: PRT
<213> ORGANISM: Artificial Sequence
<220> FEATURE:
<223> OTHER INFORMATION: Synthetic

<400> SEQUENCE: 37

Glu Ser Val Gly Leu His Leu Pro Thr Leu Ser Val Gln Glu Gly Asp
1               5                   10                  15

Asn Ser Ile Ile Asn Cys Ala Tyr Ser Asn Ser Ala Ser Asp Tyr Phe
            20                  25                  30

Ile Trp Tyr Lys Gln Glu Ser Gly Lys Gly Pro Gln Phe Ile Ile Asp
        35                  40                  45

Ile Arg Ser Asn Met Asp Lys Arg Gln Gly Gln Arg Val Thr Val Leu
    50                  55                  60

Leu Asn Lys Thr Val Lys His Leu Ser Leu Gln Ile Ala Ala Thr Gln
65                  70                  75                  80

Pro Gly Asp Ser Ala Val Tyr Phe Cys Ala Glu Lys Ser Thr Gly Asn
                85                  90                  95

Gln Phe Tyr Phe Gly Thr Gly Thr Ser Leu Thr Val Ile Pro Asn Ile
            100                 105                 110

Gln Asn Pro Glu Pro Ala Val Tyr Gln Leu Lys Asp Pro Arg Ser Gln
        115                 120                 125

Asp Ser Thr Leu Cys Leu Phe Thr Asp Phe Asp Ser Gln Ile Asn Val
```

```
    130                 135                 140

Pro Lys Thr Met Glu Ser Gly Thr Phe Ile Thr Asp Lys Cys Val Leu
145                 150                 155                 160

Asp Met Lys Ala Met Asp Ser Lys Ser Asn Gly Ala Ile Ala Trp Ser
                165                 170                 175

Asn Gln Thr Ser Phe Thr Cys Gln Asp Ile Phe Lys Glu Thr Asn Ala
            180                 185                 190

Thr Tyr Pro Ser Ser Asp Val Pro Cys Asp Ala Thr Leu Thr Glu Lys
        195                 200                 205

Ser Phe Glu Thr Asp Met Asn Leu Asn Phe Gln Asn Leu Leu Val Ile
    210                 215                 220

Val Leu Arg Ile Leu Leu Leu Lys Val Ala Gly Phe Asn Leu Leu Met
225                 230                 235                 240

Thr Leu Arg Leu Trp Ser Ser
                245


<210> SEQ ID NO 38
<211> LENGTH: 287
<212> TYPE: PRT
<213> ORGANISM: Artificial Sequence
<220> FEATURE:
<223> OTHER INFORMATION: Synthetic

<400> SEQUENCE: 38

Met Glu Thr Gly Val Thr Gln Thr Pro Arg His Leu Val Met Gly Met
1               5                   10                  15

Thr Asn Lys Lys Ser Leu Lys Cys Glu Gln His Leu Gly His Asn Ala
            20                  25                  30

Met Tyr Trp Tyr Lys Gln Ser Ala Lys Lys Pro Leu Glu Leu Met Phe
        35                  40                  45

Val Tyr Ser Leu Glu Glu Arg Val Glu Asn Asn Ser Val Pro Ser Arg
    50                  55                  60

Phe Ser Pro Glu Cys Pro Asn Ser Ser His Leu Phe Leu His Leu His
65                  70                  75                  80

Thr Leu Gln Pro Glu Asp Ser Ala Leu Tyr Leu Cys Ala Ser Ser Arg
                85                  90                  95

Val Glu Gly Ser Asp Thr Gln Tyr Phe Gly Pro Gly Thr Arg Leu Thr
            100                 105                 110

Val Leu Glu Asp Leu Arg Asn Val Thr Pro Pro Lys Val Ser Leu Phe
        115                 120                 125

Glu Pro Ser Lys Ala Glu Ile Ala Asn Lys Gln Lys Ala Thr Leu Val
    130                 135                 140

Cys Leu Ala Arg Gly Phe Phe Pro Asp His Val Glu Leu Ser Trp Trp
145                 150                 155                 160

Val Asn Gly Lys Glu Val His Ser Gly Val Cys Thr Asp Pro Gln Ala
                165                 170                 175

Tyr Lys Glu Ser Asn Tyr Ser Tyr Cys Leu Ser Ser Arg Leu Arg Val
            180                 185                 190

Ser Ala Thr Phe Trp His Asn Pro Arg Asn His Phe Arg Cys Gln Val
        195                 200                 205

Gln Phe His Gly Leu Ser Glu Glu Asp Lys Trp Pro Glu Gly Ser Pro
    210                 215                 220

Lys Pro Val Thr Gln Asn Ile Ser Ala Glu Ala Trp Gly Arg Ala Asp
225                 230                 235                 240

Cys Gly Ile Thr Ser Ala Ser Tyr Gln Gln Gly Val Leu Ser Ala Thr
```

```
                245                 250                 255

Ile Leu Tyr Glu Ile Leu Leu Gly Lys Ala Thr Leu Tyr Ala Val Leu
            260                 265                 270

Val Ser Thr Leu Val Val Met Ala Met Val Lys Arg Lys Asn Ser
        275                 280                 285


<210> SEQ ID NO 39
<211> LENGTH: 600
<212> TYPE: PRT
<213> ORGANISM: Artificial Sequence
<220> FEATURE:
<223> OTHER INFORMATION: Synthetic

<400> SEQUENCE: 39

Met Ala Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
            20                  25                  30

Gly Met Thr Asn Lys Lys Ser Leu Lys Cys Glu Gln His Leu Gly His
        35                  40                  45

Asn Ala Met Tyr Trp Tyr Lys Gln Ser Ala Lys Lys Pro Leu Glu Leu
    50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110

Ser Arg Val Glu Gly Ser Asp Thr Gln Tyr Phe Gly Pro Gly Thr Arg
        115                 120                 125

Leu Thr Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser Arg Ala Lys Arg Ser Gly Ser Gly Ala Thr Asn Phe Ser Leu Leu
305                 310                 315                 320

Lys Gln Ala Gly Asp Val Glu Glu Asn Pro Gly Pro Met His Gly Ile
```

```
                325                 330                 335

Arg Ala Leu Phe Met Tyr Leu Trp Leu Gln Leu Asp Trp Val Ser Arg
            340                 345                 350

Gly Glu Ser Val Gly Leu His Leu Pro Thr Leu Ser Val Gln Glu Gly
        355                 360                 365

Asp Asn Ser Ile Ile Asn Cys Ala Tyr Ser Asn Ser Ala Ser Asp Tyr
    370                 375                 380

Phe Ile Trp Tyr Lys Gln Glu Ser Gly Lys Gly Pro Gln Phe Ile Ile
385                 390                 395                 400

Asp Ile Arg Ser Asn Met Asp Lys Arg Gln Gly Gln Arg Val Thr Val
                405                 410                 415

Leu Leu Asn Lys Thr Val Lys His Leu Ser Leu Gln Ile Ala Ala Thr
            420                 425                 430

Gln Pro Gly Asp Ser Ala Val Tyr Phe Cys Ala Glu Lys Ser Thr Gly
        435                 440                 445

Asn Gln Phe Tyr Phe Gly Thr Gly Thr Ser Leu Thr Val Ile Pro Asn
    450                 455                 460

Ile Gln Asn Pro Glu Pro Ala Val Tyr Gln Leu Lys Asp Pro Arg Ser
465                 470                 475                 480

Gln Asp Ser Thr Leu Cys Leu Phe Thr Asp Phe Asp Ser Gln Ile Asn
                485                 490                 495

Val Pro Lys Thr Met Glu Ser Gly Thr Phe Ile Thr Asp Lys Cys Val
            500                 505                 510

Leu Asp Met Lys Ala Met Asp Ser Lys Ser Asn Gly Ala Ile Ala Trp
        515                 520                 525

Ser Asn Gln Thr Ser Phe Thr Cys Gln Asp Ile Phe Lys Glu Thr Asn
    530                 535                 540

Ala Thr Tyr Pro Ser Ser Asp Val Pro Cys Asp Ala Thr Leu Thr Glu
545                 550                 555                 560

Lys Ser Phe Glu Thr Asp Met Asn Leu Asn Phe Gln Asn Leu Leu Val
                565                 570                 575

Ile Val Leu Arg Ile Leu Leu Leu Lys Val Ala Gly Phe Asn Leu Leu
            580                 585                 590

Met Thr Leu Arg Leu Trp Ser Ser
        595                 600


<210> SEQ ID NO 40
<211> LENGTH: 6
<212> TYPE: PRT
<213> ORGANISM: Homo sapiens

<400> SEQUENCE: 40

Val Ser Gly Asn Pro Tyr
1               5


<210> SEQ ID NO 41
<211> LENGTH: 8
<212> TYPE: PRT
<213> ORGANISM: Homo sapiens

<400> SEQUENCE: 41

Tyr Ile Thr Gly Asp Asn Leu Val
1               5


<210> SEQ ID NO 42
<211> LENGTH: 16
<212> TYPE: PRT
```

<213> ORGANISM: Homo sapiens

<400> SEQUENCE: 42

Cys Ala Val Arg Asp Pro Thr Val Ser Gly Thr Tyr Lys Tyr Ile Phe
1 5 10 15

<210> SEQ ID NO 43
<211> LENGTH: 6
<212> TYPE: PRT
<213> ORGANISM: Homo sapiens

<400> SEQUENCE: 43

Asp Phe Gln Ala Thr Thr
1 5

<210> SEQ ID NO 44
<211> LENGTH: 7
<212> TYPE: PRT
<213> ORGANISM: Homo sapiens

<400> SEQUENCE: 44

Ser Asn Glu Gly Ser Lys Ala
1 5

<210> SEQ ID NO 45
<211> LENGTH: 15
<212> TYPE: PRT
<213> ORGANISM: Homo sapiens

<400> SEQUENCE: 45

Cys Ser Ala Ile Arg Asp Arg Ser Gly Gly Glu Thr Gln Tyr Phe
1 5 10 15

<210> SEQ ID NO 46
<211> LENGTH: 115
<212> TYPE: PRT
<213> ORGANISM: Homo sapiens

<400> SEQUENCE: 46

Gln Ser Val Ala Gln Pro Glu Asp Gln Val Asn Val Ala Glu Gly Asn
1 5 10 15

Pro Leu Thr Val Lys Cys Thr Tyr Ser Val Ser Gly Asn Pro Tyr Leu
20 25 30

Phe Trp Tyr Val Gln Tyr Pro Asn Arg Gly Leu Gln Phe Leu Leu Lys
35 40 45

Tyr Ile Thr Gly Asp Asn Leu Val Lys Gly Ser Tyr Gly Phe Glu Ala
50 55 60

Glu Phe Asn Lys Ser Gln Thr Ser Phe His Leu Lys Lys Pro Ser Ala
65 70 75 80

Leu Val Ser Asp Ser Ala Leu Tyr Phe Cys Ala Val Arg Asp Pro Thr
85 90 95

Val Ser Gly Thr Tyr Lys Tyr Ile Phe Gly Thr Gly Thr Arg Leu Lys
100 105 110

Val Leu Ala
115

<210> SEQ ID NO 47
<211> LENGTH: 116
<212> TYPE: PRT
<213> ORGANISM: Homo sapiens

<400> SEQUENCE: 47

```
Ala Val Val Ser Gln His Pro Ser Arg Val Ile Cys Lys Ser Gly Thr
1               5                   10                  15

Ser Val Lys Ile Glu Cys Arg Ser Leu Asp Phe Gln Ala Thr Thr Met
            20                  25                  30

Phe Trp Tyr Arg Gln Phe Pro Lys Gln Ser Leu Met Leu Met Ala Thr
        35                  40                  45

Ser Asn Glu Gly Ser Lys Ala Thr Tyr Glu Gln Gly Val Glu Lys Asp
    50                  55                  60

Lys Phe Leu Ile Asn His Ala Ser Leu Thr Leu Ser Thr Leu Thr Val
65                  70                  75                  80

Thr Ser Ala His Pro Glu Asp Ser Ser Phe Tyr Ile Cys Ser Ala Ile
                85                  90                  95

Arg Asp Arg Ser Gly Gly Glu Thr Gln Tyr Phe Gly Pro Gly Thr Arg
            100                 105                 110

Leu Leu Val Leu
        115


<210> SEQ ID NO 48
<211> LENGTH: 135
<212> TYPE: PRT
<213> ORGANISM: Artificial Sequence
<220> FEATURE:
<223> OTHER INFORMATION: Synthetic

<400> SEQUENCE: 48

Met His Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Pro Thr Val Ser Gly Thr Tyr Lys Tyr Ile Phe Gly Thr Gly
        115                 120                 125

Thr Arg Leu Lys Val Leu Ala
    130                 135


<210> SEQ ID NO 49
<211> LENGTH: 131
<212> TYPE: PRT
<213> ORGANISM: Artificial Sequence
<220> FEATURE:
<223> OTHER INFORMATION: Synthetic

<400> SEQUENCE: 49

Met Ala Leu Leu Leu Leu Leu Leu Gly Pro Gly Ser Gly Leu Gly Ala
1               5                   10                  15

Val Val Ser Gln His Pro Ser Arg Val Ile Cys Lys Ser Gly Thr Ser
            20                  25                  30

Val Lys Ile Glu Cys Arg Ser Leu Asp Phe Gln Ala Thr Thr Met Phe
```

```
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Ile Arg
            100                 105                 110

Asp Arg Ser Gly Gly Glu Thr Gln Tyr Phe Gly Pro Gly Thr Arg Leu
        115                 120                 125

Leu Val Leu
    130


<210> SEQ ID NO 50
<211> LENGTH: 135
<212> TYPE: PRT
<213> ORGANISM: Homo sapiens

<400> SEQUENCE: 50

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Pro Thr Val Ser Gly Thr Tyr Lys Tyr Ile Phe Gly Thr Gly
        115                 120                 125

Thr Arg Leu Lys Val Leu Ala
    130                 135


<210> SEQ ID NO 51
<211> LENGTH: 131
<212> TYPE: PRT
<213> ORGANISM: Homo sapiens

<400> SEQUENCE: 51

Met Leu Leu Leu Leu Leu Leu Leu Gly Pro Gly Ser Gly Leu Gly Ala
1               5                   10                  15

Val Val Ser Gln His Pro Ser Arg Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
```

```
                85                  90                  95

Ser Ala His Pro Glu Asp Ser Ser Phe Tyr Ile Cys Ser Ala Ile Arg
            100                 105                 110

Asp Arg Ser Gly Gly Glu Thr Gln Tyr Phe Gly Pro Gly Thr Arg Leu
        115                 120                 125

Leu Val Leu
    130


<210> SEQ ID NO 52
<211> LENGTH: 272
<212> TYPE: PRT
<213> ORGANISM: Artificial Sequence
<220> FEATURE:
<223> OTHER INFORMATION: Synthetic

<400> SEQUENCE: 52

Met His Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Pro Thr Val Ser Gly Thr Tyr Lys Tyr Ile Phe Gly Thr Gly
        115                 120                 125

Thr Arg Leu Lys Val Leu Ala Asn Ile Gln Asn Pro Glu Pro Ala Val
    130                 135                 140

Tyr Gln Leu Lys Asp Pro Arg Ser Gln Asp Ser Thr Leu Cys Leu Phe
145                 150                 155                 160

Thr Asp Phe Asp Ser Gln Ile Asn Val Pro Lys Thr Met Glu Ser Gly
                165                 170                 175

Thr Phe Ile Thr Asp Lys Cys Val Leu Asp Met Lys Ala Met Asp Ser
            180                 185                 190

Lys Ser Asn Gly Ala Ile Ala Trp Ser Asn Gln Thr Ser Phe Thr Cys
        195                 200                 205

Gln Asp Ile Phe Lys Glu Thr Asn Ala Thr Tyr Pro Ser Ser Asp Val
    210                 215                 220

Pro Cys Asp Ala Thr Leu Thr Glu Lys Ser Phe Glu Thr Asp Met Asn
225                 230                 235                 240

Leu Asn Phe Gln Asn Leu Leu Val Ile Val Leu Arg Ile Leu Leu Leu
                245                 250                 255

Lys Val Ala Gly Phe Asn Leu Leu Met Thr Leu Arg Leu Trp Ser Ser
            260                 265                 270


<210> SEQ ID NO 53
<211> LENGTH: 304
<212> TYPE: PRT
<213> ORGANISM: Artificial Sequence
<220> FEATURE:
<223> OTHER INFORMATION: Synthetic
```

<400> SEQUENCE: 53

Met Ala Leu Leu Leu Leu Leu Leu Gly Pro Gly Ser Gly Leu Gly Ala
1 5 10 15

Val Val Ser Gln His Pro Ser Arg Val Ile Cys Lys Ser Gly Thr Ser
20 25 30

Val Lys Ile Glu Cys Arg Ser Leu Asp Phe Gln Ala Thr Thr Met Phe
35 40 45

Trp Tyr Arg Gln Phe Pro Lys Gln Ser Leu Met Leu Met Ala Thr Ser
50 55 60

Asn Glu Gly Ser Lys Ala Thr Tyr Glu Gln Gly Val Glu Lys Asp Lys
65 70 75 80

Phe Leu Ile Asn His Ala Ser Leu Thr Leu Ser Thr Leu Thr Val Thr
85 90 95

Ser Ala His Pro Glu Asp Ser Ser Phe Tyr Ile Cys Ser Ala Ile Arg
100 105 110

Asp Arg Ser Gly Gly Glu Thr Gln Tyr Phe Gly Pro Gly Thr Arg Leu
115 120 125

Leu Val Leu Glu Asp Leu Arg Asn Val Thr Pro Pro Lys Val Ser Leu
130 135 140

Phe Glu Pro Ser Lys Ala Glu Ile Ala Asn Lys Gln Lys Ala Thr Leu
145 150 155 160

Val Cys Leu Ala Arg Gly Phe Phe Pro Asp His Val Glu Leu Ser Trp
165 170 175

Trp Val Asn Gly Lys Glu Val His Ser Gly Val Cys Thr Asp Pro Gln
180 185 190

Ala Tyr Lys Glu Ser Asn Tyr Ser Tyr Cys Leu Ser Ser Arg Leu Arg
195 200 205

Val Ser Ala Thr Phe Trp His Asn Pro Arg Asn His Phe Arg Cys Gln
210 215 220

Val Gln Phe His Gly Leu Ser Glu Glu Asp Lys Trp Pro Glu Gly Ser
225 230 235 240

Pro Lys Pro Val Thr Gln Asn Ile Ser Ala Glu Ala Trp Gly Arg Ala
245 250 255

Asp Cys Gly Ile Thr Ser Ala Ser Tyr Gln Gln Gly Val Leu Ser Ala
260 265 270

Thr Ile Leu Tyr Glu Ile Leu Leu Gly Lys Ala Thr Leu Tyr Ala Val
275 280 285

Leu Val Ser Thr Leu Val Val Met Ala Met Val Lys Arg Lys Asn Ser
290 295 300

<210> SEQ ID NO 54
<211> LENGTH: 272
<212> TYPE: PRT
<213> ORGANISM: Artificial Sequence
<220> FEATURE:
<223> OTHER INFORMATION: Synthetic

<400> SEQUENCE: 54

Met Ala Ser Ala Pro Ile Ser Met Leu Ala Met Leu Phe Thr Leu Ser
1 5 10 15

Gly Leu Arg Ala Gln Ser Val Ala Gln Pro Glu Asp Gln Val Asn Val
20 25 30

Ala Glu Gly Asn Pro Leu Thr Val Lys Cys Thr Tyr Ser Val Ser Gly
35 40 45

-continued

```
Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Pro Thr Val Ser Gly Thr Tyr Lys Tyr Ile Phe Gly Thr Gly
        115                 120                 125

Thr Arg Leu Lys Val Leu Ala Asn Ile Gln Asn Pro Glu Pro Ala Val
    130                 135                 140

Tyr Gln Leu Lys Asp Pro Arg Ser Gln Asp Ser Thr Leu Cys Leu Phe
145                 150                 155                 160

Thr Asp Phe Asp Ser Gln Ile Asn Val Pro Lys Thr Met Glu Ser Gly
                165                 170                 175

Thr Phe Ile Thr Asp Lys Cys Val Leu Asp Met Lys Ala Met Asp Ser
            180                 185                 190

Lys Ser Asn Gly Ala Ile Ala Trp Ser Asn Gln Thr Ser Phe Thr Cys
        195                 200                 205

Gln Asp Ile Phe Lys Glu Thr Asn Ala Thr Tyr Pro Ser Ser Asp Val
    210                 215                 220

Pro Cys Asp Ala Thr Leu Thr Glu Lys Ser Phe Glu Thr Asp Met Asn
225                 230                 235                 240

Leu Asn Phe Gln Asn Leu Leu Val Ile Val Leu Arg Ile Leu Leu Leu
                245                 250                 255

Lys Val Ala Gly Phe Asn Leu Leu Met Thr Leu Arg Leu Trp Ser Ser
            260                 265                 270


<210> SEQ ID NO 55
<211> LENGTH: 304
<212> TYPE: PRT
<213> ORGANISM: Artificial Sequence
<220> FEATURE:
<223> OTHER INFORMATION: Synthetic

<400> SEQUENCE: 55

Met Leu Leu Leu Leu Leu Leu Leu Gly Pro Gly Ser Gly Leu Gly Ala
1               5                   10                  15

Val Val Ser Gln His Pro Ser Arg Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Ile Arg
            100                 105                 110

Asp Arg Ser Gly Gly Glu Thr Gln Tyr Phe Gly Pro Gly Thr Arg Leu
        115                 120                 125

Leu Val Leu Glu Asp Leu Arg Asn Val Thr Pro Pro Lys Val Ser Leu
    130                 135                 140
```

-continued

```
Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300


<210> SEQ ID NO 56
<211> LENGTH: 252
<212> TYPE: PRT
<213> ORGANISM: Artificial Sequence
<220> FEATURE:
<223> OTHER INFORMATION: Synthetic

<400> SEQUENCE: 56

Gln Ser Val Ala Gln Pro Glu Asp Gln Val Asn Val Ala Glu Gly Asn
1               5                   10                  15

Pro Leu Thr Val Lys Cys Thr Tyr Ser Val Ser Gly Asn Pro Tyr Leu
            20                  25                  30

Phe Trp Tyr Val Gln Tyr Pro Asn Arg Gly Leu Gln Phe Leu Leu Lys
        35                  40                  45

Tyr Ile Thr Gly Asp Asn Leu Val Lys Gly Ser Tyr Gly Phe Glu Ala
    50                  55                  60

Glu Phe Asn Lys Ser Gln Thr Ser Phe His Leu Lys Lys Pro Ser Ala
65                  70                  75                  80

Leu Val Ser Asp Ser Ala Leu Tyr Phe Cys Ala Val Arg Asp Pro Thr
                85                  90                  95

Val Ser Gly Thr Tyr Lys Tyr Ile Phe Gly Thr Gly Thr Arg Leu Lys
            100                 105                 110

Val Leu Ala Asn Ile Gln Asn Pro Glu Pro Ala Val Tyr Gln Leu Lys
        115                 120                 125

Asp Pro Arg Ser Gln Asp Ser Thr Leu Cys Leu Phe Thr Asp Phe Asp
    130                 135                 140

Ser Gln Ile Asn Val Pro Lys Thr Met Glu Ser Gly Thr Phe Ile Thr
145                 150                 155                 160

Asp Lys Cys Val Leu Asp Met Lys Ala Met Asp Ser Lys Ser Asn Gly
                165                 170                 175

Ala Ile Ala Trp Ser Asn Gln Thr Ser Phe Thr Cys Gln Asp Ile Phe
            180                 185                 190

Lys Glu Thr Asn Ala Thr Tyr Pro Ser Ser Asp Val Pro Cys Asp Ala
        195                 200                 205
```

-continued

```
Thr Leu Thr Glu Lys Ser Phe Glu Thr Asp Met Asn Leu Asn Phe Gln
    210                 215                 220

Asn Leu Leu Val Ile Val Leu Arg Ile Leu Leu Leu Lys Val Ala Gly
225                 230                 235                 240

Phe Asn Leu Leu Met Thr Leu Arg Leu Trp Ser Ser
                245                 250


<210> SEQ ID NO 57
<211> LENGTH: 289
<212> TYPE: PRT
<213> ORGANISM: Artificial Sequence
<220> FEATURE:
<223> OTHER INFORMATION: Synthetic

<400> SEQUENCE: 57

Ala Val Val Ser Gln His Pro Ser Arg Val Ile Cys Lys Ser Gly Thr
1               5                   10                  15

Ser Val Lys Ile Glu Cys Arg Ser Leu Asp Phe Gln Ala Thr Thr Met
            20                  25                  30

Phe Trp Tyr Arg Gln Phe Pro Lys Gln Ser Leu Met Leu Met Ala Thr
        35                  40                  45

Ser Asn Glu Gly Ser Lys Ala Thr Tyr Glu Gln Gly Val Glu Lys Asp
    50                  55                  60

Lys Phe Leu Ile Asn His Ala Ser Leu Thr Leu Ser Thr Leu Thr Val
65                  70                  75                  80

Thr Ser Ala His Pro Glu Asp Ser Ser Phe Tyr Ile Cys Ser Ala Ile
                85                  90                  95

Arg Asp Arg Ser Gly Gly Glu Thr Gln Tyr Phe Gly Pro Gly Thr Arg
            100                 105                 110

Leu Leu Val Leu Glu Asp Leu Arg Asn Val Thr Pro Pro Lys Val Ser
        115                 120                 125

Leu Phe Glu Pro Ser Lys Ala Glu Ile Ala Asn Lys Gln Lys Ala Thr
    130                 135                 140

Leu Val Cys Leu Ala Arg Gly Phe Phe Pro Asp His Val Glu Leu Ser
145                 150                 155                 160

Trp Trp Val Asn Gly Lys Glu Val His Ser Gly Val Cys Thr Asp Pro
                165                 170                 175

Gln Ala Tyr Lys Glu Ser Asn Tyr Ser Tyr Cys Leu Ser Ser Arg Leu
            180                 185                 190

Arg Val Ser Ala Thr Phe Trp His Asn Pro Arg Asn His Phe Arg Cys
        195                 200                 205

Gln Val Gln Phe His Gly Leu Ser Glu Glu Asp Lys Trp Pro Glu Gly
    210                 215                 220

Ser Pro Lys Pro Val Thr Gln Asn Ile Ser Ala Glu Ala Trp Gly Arg
225                 230                 235                 240

Ala Asp Cys Gly Ile Thr Ser Ala Ser Tyr Gln Gln Gly Val Leu Ser
                245                 250                 255

Ala Thr Ile Leu Tyr Glu Ile Leu Leu Gly Lys Ala Thr Leu Tyr Ala
            260                 265                 270

Val Leu Val Ser Thr Leu Val Val Met Ala Met Val Lys Arg Lys Asn
        275                 280                 285

Ser


<210> SEQ ID NO 58
<211> LENGTH: 603
<212> TYPE: PRT
```

```
<213> ORGANISM: Artificial Sequence
<220> FEATURE:
<223> OTHER INFORMATION: Synthetic

<400> SEQUENCE: 58

Met Ala Leu Leu Leu Leu Leu Leu Gly Pro Gly Ser Gly Leu Gly Ala
1               5                   10                  15

Val Val Ser Gln His Pro Ser Arg Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Ile Arg
            100                 105                 110

Asp Arg Ser Gly Gly Glu Thr Gln Tyr Phe Gly Pro Gly Thr Arg Leu
        115                 120                 125

Leu Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300

Arg Ala Lys Arg Ser Gly Ser Gly Ala Thr Asn Phe Ser Leu Leu Lys
305                 310                 315                 320

Gln Ala Gly Asp Val Glu Glu Asn Pro Gly Pro Met His Ser Ala Pro
                325                 330                 335

Ile Ser Met Leu Ala Met Leu Phe Thr Leu Ser Gly Leu Arg Ala Gln
            340                 345                 350

Ser Val Ala Gln Pro Glu Asp Gln Val Asn Val Ala Glu Gly Asn Pro
        355                 360                 365

Leu Thr Val Lys Cys Thr Tyr Ser Val Ser Gly Asn Pro Tyr Leu Phe
    370                 375                 380

Trp Tyr Val Gln Tyr Pro Asn Arg Gly Leu Gln Phe Leu Leu Lys Tyr
```

```
385                 390                 395                 400

Ile Thr Gly Asp Asn Leu Val Lys Gly Ser Tyr Gly Phe Glu Ala Glu
                405                 410                 415

Phe Asn Lys Ser Gln Thr Ser Phe His Leu Lys Lys Pro Ser Ala Leu
            420                 425                 430

Val Ser Asp Ser Ala Leu Tyr Phe Cys Ala Val Arg Asp Pro Thr Val
        435                 440                 445

Ser Gly Thr Tyr Lys Tyr Ile Phe Gly Thr Gly Thr Arg Leu Lys Val
    450                 455                 460

Leu Ala Asn Ile Gln Asn Pro Glu Pro Ala Val Tyr Gln Leu Lys Asp
465                 470                 475                 480

Pro Arg Ser Gln Asp Ser Thr Leu Cys Leu Phe Thr Asp Phe Asp Ser
                485                 490                 495

Gln Ile Asn Val Pro Lys Thr Met Glu Ser Gly Thr Phe Ile Thr Asp
            500                 505                 510

Lys Cys Val Leu Asp Met Lys Ala Met Asp Ser Lys Ser Asn Gly Ala
        515                 520                 525

Ile Ala Trp Ser Asn Gln Thr Ser Phe Thr Cys Gln Asp Ile Phe Lys
    530                 535                 540

Glu Thr Asn Ala Thr Tyr Pro Ser Ser Asp Val Pro Cys Asp Ala Thr
545                 550                 555                 560

Leu Thr Glu Lys Ser Phe Glu Thr Asp Met Asn Leu Asn Phe Gln Asn
                565                 570                 575

Leu Leu Val Ile Val Leu Arg Ile Leu Leu Leu Lys Val Ala Gly Phe
            580                 585                 590

Asn Leu Leu Met Thr Leu Arg Leu Trp Ser Ser
        595                 600


<210> SEQ ID NO 59
<211> LENGTH: 6
<212> TYPE: PRT
<213> ORGANISM: Homo sapiens

<400> SEQUENCE: 59

Asn Thr Ala Phe Asp Tyr
1               5


<210> SEQ ID NO 60
<211> LENGTH: 7
<212> TYPE: PRT
<213> ORGANISM: Homo sapiens

<400> SEQUENCE: 60

Ile Arg Pro Asp Val Ser Glu
1               5


<210> SEQ ID NO 61
<211> LENGTH: 14
<212> TYPE: PRT
<213> ORGANISM: Homo sapiens

<400> SEQUENCE: 61

Cys Ala Ala Lys Arg Gln Gly Gly Ser Glu Lys Leu Val Phe
1               5                   10


<210> SEQ ID NO 62
<211> LENGTH: 5
<212> TYPE: PRT
<213> ORGANISM: Homo sapiens
```

<400> SEQUENCE: 62

Ser Gly His Thr Ala
1 5

<210> SEQ ID NO 63
<211> LENGTH: 6
<212> TYPE: PRT
<213> ORGANISM: Homo sapiens

<400> SEQUENCE: 63

Phe Gln Gly Asn Ser Ala
1 5

<210> SEQ ID NO 64
<211> LENGTH: 14
<212> TYPE: PRT
<213> ORGANISM: Homo sapiens

<400> SEQUENCE: 64

Cys Ala Ser Ser Leu Gly Gly Ser Ser Glu Thr Gln Tyr Phe
1 5 10

<210> SEQ ID NO 65
<211> LENGTH: 120
<212> TYPE: PRT
<213> ORGANISM: Homo sapiens

<400> SEQUENCE: 65

Gln Gln Lys Glu Lys Ser Asp Gln Gln Gln Val Lys Gln Ser Pro Gln
1 5 10 15

Ser Leu Ile Val Gln Lys Gly Gly Ile Ser Ile Ile Asn Cys Ala Tyr
20 25 30

Glu Asn Thr Ala Phe Asp Tyr Phe Pro Trp Tyr Gln Gln Phe Pro Gly
35 40 45

Lys Gly Pro Ala Leu Leu Ile Ala Ile Arg Pro Asp Val Ser Glu Lys
50 55 60

Lys Glu Gly Arg Phe Thr Ile Ser Phe Asn Lys Ser Ala Lys Gln Phe
65 70 75 80

Ser Leu His Ile Met Asp Ser Gln Pro Gly Asp Ser Ala Thr Tyr Phe
85 90 95

Cys Ala Ala Lys Arg Gln Gly Gly Ser Glu Lys Leu Val Phe Gly Lys
100 105 110

Gly Thr Lys Leu Thr Val Asn Pro
115 120

<210> SEQ ID NO 66
<211> LENGTH: 112
<212> TYPE: PRT
<213> ORGANISM: Homo sapiens

<400> SEQUENCE: 66

Gly Val Ser Gln Ser Pro Ser Asn Lys Val Thr Glu Lys Gly Lys Asp
1 5 10 15

Val Glu Leu Arg Cys Asp Pro Ile Ser Gly His Thr Ala Leu Tyr Trp
20 25 30

Tyr Arg Gln Ser Leu Gly Gln Gly Leu Glu Phe Leu Ile Tyr Phe Gln
35 40 45

Gly Asn Ser Ala Pro Asp Lys Ser Gly Leu Pro Ser Asp Arg Phe Ser
50 55 60

```
Ala Glu Arg Thr Gly Gly Ser Val Ser Thr Leu Thr Ile Gln Arg Thr
65                  70                  75                  80

Gln Gln Glu Asp Ser Ala Val Tyr Leu Cys Ala Ser Ser Leu Gly Gly
                85                  90                  95

Ser Ser Glu Thr Gln Tyr Phe Gly Pro Gly Thr Arg Leu Leu Val Leu
            100                 105                 110


<210> SEQ ID NO 67
<211> LENGTH: 141
<212> TYPE: PRT
<213> ORGANISM: Artificial Sequence
<220> FEATURE:
<223> OTHER INFORMATION: Synthetic

<400> SEQUENCE: 67

Met His Lys Ile Leu Gly Ala Ser Phe Leu Val Leu Trp Leu Gln Leu
1               5                   10                  15

Cys Trp Val Ser Gly Gln Gln Lys Glu Lys Ser Asp Gln Gln Gln Val
            20                  25                  30

Lys Gln Ser Pro Gln Ser Leu Ile Val Gln Lys Gly Gly Ile Ser Ile
        35                  40                  45

Ile Asn Cys Ala Tyr Glu Asn Thr Ala Phe Asp Tyr Phe Pro Trp Tyr
    50                  55                  60

Gln Gln Phe Pro Gly Lys Gly Pro Ala Leu Leu Ile Ala Ile Arg Pro
65                  70                  75                  80

Asp Val Ser Glu Lys Lys Glu Gly Arg Phe Thr Ile Ser Phe Asn Lys
                85                  90                  95

Ser Ala Lys Gln Phe Ser Leu His Ile Met Asp Ser Gln Pro Gly Asp
            100                 105                 110

Ser Ala Thr Tyr Phe Cys Ala Ala Lys Arg Gln Gly Gly Ser Glu Lys
        115                 120                 125

Leu Val Phe Gly Lys Gly Thr Lys Leu Thr Val Asn Pro
    130                 135                 140


<210> SEQ ID NO 68
<211> LENGTH: 133
<212> TYPE: PRT
<213> ORGANISM: Artificial Sequence
<220> FEATURE:
<223> OTHER INFORMATION: Synthetic

<400> SEQUENCE: 68

Met Ala Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ser Leu Gly Gly Ser Ser Glu Thr Gln Tyr Phe Gly Pro Gly Thr
```

```
        115                 120                 125

Arg Leu Leu Val Leu
    130


<210> SEQ ID NO 69
<211> LENGTH: 141
<212> TYPE: PRT
<213> ORGANISM: Homo sapiens

<400> SEQUENCE: 69

Met Asp Lys Ile Leu Gly Ala Ser Phe Leu Val Leu Trp Leu Gln Leu
1               5                   10                  15

Cys Trp Val Ser Gly Gln Gln Lys Glu Lys Ser Asp Gln Gln Gln Val
            20                  25                  30

Lys Gln Ser Pro Gln Ser Leu Ile Val Gln Lys Gly Gly Ile Ser Ile
        35                  40                  45

Ile Asn Cys Ala Tyr Glu Asn Thr Ala Phe Asp Tyr Phe Pro Trp Tyr
    50                  55                  60

Gln Gln Phe Pro Gly Lys Gly Pro Ala Leu Leu Ile Ala Ile Arg Pro
65                  70                  75                  80

Asp Val Ser Glu Lys Lys Glu Gly Arg Phe Thr Ile Ser Phe Asn Lys
                85                  90                  95

Ser Ala Lys Gln Phe Ser Leu His Ile Met Asp Ser Gln Pro Gly Asp
            100                 105                 110

Ser Ala Thr Tyr Phe Cys Ala Ala Lys Arg Gln Gly Gly Ser Glu Lys
        115                 120                 125

Leu Val Phe Gly Lys Gly Thr Lys Leu Thr Val Asn Pro
    130                 135                 140


<210> SEQ ID NO 70
<211> LENGTH: 133
<212> TYPE: PRT
<213> ORGANISM: Homo sapiens

<400> SEQUENCE: 70

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ser Leu Gly Gly Ser Ser Glu Thr Gln Tyr Phe Gly Pro Gly Thr
        115                 120                 125

Arg Leu Leu Val Leu
    130


<210> SEQ ID NO 71
<211> LENGTH: 278
<212> TYPE: PRT
```

<213> ORGANISM: Artificial Sequence
<220> FEATURE:
<223> OTHER INFORMATION: Synthetic

<400> SEQUENCE: 71

```
Met His Lys Ile Leu Gly Ala Ser Phe Leu Val Leu Trp Leu Gln Leu
1               5                   10                  15

Cys Trp Val Ser Gly Gln Gln Lys Glu Lys Ser Asp Gln Gln Gln Val
            20                  25                  30

Lys Gln Ser Pro Gln Ser Leu Ile Val Gln Lys Gly Gly Ile Ser Ile
        35                  40                  45

Ile Asn Cys Ala Tyr Glu Asn Thr Ala Phe Asp Tyr Phe Pro Trp Tyr
    50                  55                  60

Gln Gln Phe Pro Gly Lys Gly Pro Ala Leu Leu Ile Ala Ile Arg Pro
65                  70                  75                  80

Asp Val Ser Glu Lys Lys Glu Gly Arg Phe Thr Ile Ser Phe Asn Lys
                85                  90                  95

Ser Ala Lys Gln Phe Ser Leu His Ile Met Asp Ser Gln Pro Gly Asp
            100                 105                 110

Ser Ala Thr Tyr Phe Cys Ala Ala Lys Arg Gln Gly Gly Ser Glu Lys
        115                 120                 125

Leu Val Phe Gly Lys Gly Thr Lys Leu Thr Val Asn Pro Asn Ile Gln
    130                 135                 140

Asn Pro Glu Pro Ala Val Tyr Gln Leu Lys Asp Pro Arg Ser Gln Asp
145                 150                 155                 160

Ser Thr Leu Cys Leu Phe Thr Asp Phe Asp Ser Gln Ile Asn Val Pro
                165                 170                 175

Lys Thr Met Glu Ser Gly Thr Phe Ile Thr Asp Lys Cys Val Leu Asp
            180                 185                 190

Met Lys Ala Met Asp Ser Lys Ser Asn Gly Ala Ile Ala Trp Ser Asn
        195                 200                 205

Gln Thr Ser Phe Thr Cys Gln Asp Ile Phe Lys Glu Thr Asn Ala Thr
    210                 215                 220

Tyr Pro Ser Ser Asp Val Pro Cys Asp Ala Thr Leu Thr Glu Lys Ser
225                 230                 235                 240

Phe Glu Thr Asp Met Asn Leu Asn Phe Gln Asn Leu Leu Val Ile Val
                245                 250                 255

Leu Arg Ile Leu Leu Leu Lys Val Ala Gly Phe Asn Leu Leu Met Thr
            260                 265                 270

Leu Arg Leu Trp Ser Ser
        275
```

<210> SEQ ID NO 72
<211> LENGTH: 306
<212> TYPE: PRT
<213> ORGANISM: Artificial Sequence
<220> FEATURE:
<223> OTHER INFORMATION: Synthetic

<400> SEQUENCE: 72

```
Met Ala Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45
```

```
Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ser Leu Gly Gly Ser Ser Glu Thr Gln Tyr Phe Gly Pro Gly Thr
        115                 120                 125

Arg Leu Leu Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300

Asn Ser
305


<210> SEQ ID NO 73
<211> LENGTH: 278
<212> TYPE: PRT
<213> ORGANISM: Artificial Sequence
<220> FEATURE:
<223> OTHER INFORMATION: Synthetic

<400> SEQUENCE: 73

Met Asp Lys Ile Leu Gly Ala Ser Phe Leu Val Leu Trp Leu Gln Leu
1               5                   10                  15

Cys Trp Val Ser Gly Gln Gln Lys Glu Lys Ser Asp Gln Gln Gln Val
            20                  25                  30

Lys Gln Ser Pro Gln Ser Leu Ile Val Gln Lys Gly Gly Ile Ser Ile
        35                  40                  45

Ile Asn Cys Ala Tyr Glu Asn Thr Ala Phe Asp Tyr Phe Pro Trp Tyr
    50                  55                  60

Gln Gln Phe Pro Gly Lys Gly Pro Ala Leu Leu Ile Ala Ile Arg Pro
65                  70                  75                  80

Asp Val Ser Glu Lys Lys Glu Gly Arg Phe Thr Ile Ser Phe Asn Lys
                85                  90                  95
```

-continued

```
Ser Ala Lys Gln Phe Ser Leu His Ile Met Asp Ser Gln Pro Gly Asp
            100                 105                 110

Ser Ala Thr Tyr Phe Cys Ala Ala Lys Arg Gln Gly Gly Ser Glu Lys
        115                 120                 125

Leu Val Phe Gly Lys Gly Thr Lys Leu Thr Val Asn Pro Asn Ile Gln
    130                 135                 140

Asn Pro Glu Pro Ala Val Tyr Gln Leu Lys Asp Pro Arg Ser Gln Asp
145                 150                 155                 160

Ser Thr Leu Cys Leu Phe Thr Asp Phe Asp Ser Gln Ile Asn Val Pro
                165                 170                 175

Lys Thr Met Glu Ser Gly Thr Phe Ile Thr Asp Lys Cys Val Leu Asp
            180                 185                 190

Met Lys Ala Met Asp Ser Lys Ser Asn Gly Ala Ile Ala Trp Ser Asn
        195                 200                 205

Gln Thr Ser Phe Thr Cys Gln Asp Ile Phe Lys Glu Thr Asn Ala Thr
    210                 215                 220

Tyr Pro Ser Ser Asp Val Pro Cys Asp Ala Thr Leu Thr Glu Lys Ser
225                 230                 235                 240

Phe Glu Thr Asp Met Asn Leu Asn Phe Gln Asn Leu Leu Val Ile Val
                245                 250                 255

Leu Arg Ile Leu Leu Leu Lys Val Ala Gly Phe Asn Leu Leu Met Thr
            260                 265                 270

Leu Arg Leu Trp Ser Ser
        275


<210> SEQ ID NO 74
<211> LENGTH: 306
<212> TYPE: PRT
<213> ORGANISM: Artificial Sequence
<220> FEATURE:
<223> OTHER INFORMATION: Synthetic

<400> SEQUENCE: 74

Met Gly Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ser Leu Gly Gly Ser Ser Glu Thr Gln Tyr Phe Gly Pro Gly Thr
        115                 120                 125

Arg Leu Leu Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175
```

```
Ser Trp Trp Val Asn Gly Lys Glu Val His Ser Gly Val Cys Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300

Asn Ser
305


<210> SEQ ID NO 75
<211> LENGTH: 257
<212> TYPE: PRT
<213> ORGANISM: Artificial Sequence
<220> FEATURE:
<223> OTHER INFORMATION: Synthetic

<400> SEQUENCE: 75

Gln Gln Lys Glu Lys Ser Asp Gln Gln Gln Val Lys Gln Ser Pro Gln
1               5                   10                  15

Ser Leu Ile Val Gln Lys Gly Gly Ile Ser Ile Ile Asn Cys Ala Tyr
            20                  25                  30

Glu Asn Thr Ala Phe Asp Tyr Phe Pro Trp Tyr Gln Gln Phe Pro Gly
        35                  40                  45

Lys Gly Pro Ala Leu Leu Ile Ala Ile Arg Pro Asp Val Ser Glu Lys
    50                  55                  60

Lys Glu Gly Arg Phe Thr Ile Ser Phe Asn Lys Ser Ala Lys Gln Phe
65                  70                  75                  80

Ser Leu His Ile Met Asp Ser Gln Pro Gly Asp Ser Ala Thr Tyr Phe
                85                  90                  95

Cys Ala Ala Lys Arg Gln Gly Gly Ser Glu Lys Leu Val Phe Gly Lys
            100                 105                 110

Gly Thr Lys Leu Thr Val Asn Pro Asn Ile Gln Asn Pro Glu Pro Ala
        115                 120                 125

Val Tyr Gln Leu Lys Asp Pro Arg Ser Gln Asp Ser Thr Leu Cys Leu
    130                 135                 140

Phe Thr Asp Phe Asp Ser Gln Ile Asn Val Pro Lys Thr Met Glu Ser
145                 150                 155                 160

Gly Thr Phe Ile Thr Asp Lys Cys Val Leu Asp Met Lys Ala Met Asp
                165                 170                 175

Ser Lys Ser Asn Gly Ala Ile Ala Trp Ser Asn Gln Thr Ser Phe Thr
            180                 185                 190

Cys Gln Asp Ile Phe Lys Glu Thr Asn Ala Thr Tyr Pro Ser Ser Asp
        195                 200                 205

Val Pro Cys Asp Ala Thr Leu Thr Glu Lys Ser Phe Glu Thr Asp Met
    210                 215                 220
```

```
Asn Leu Asn Phe Gln Asn Leu Leu Val Ile Val Leu Arg Ile Leu Leu
225                 230                 235                 240

Leu Lys Val Ala Gly Phe Asn Leu Leu Met Thr Leu Arg Leu Trp Ser
                245                 250                 255

Ser


<210> SEQ ID NO 76
<211> LENGTH: 285
<212> TYPE: PRT
<213> ORGANISM: Artificial Sequence
<220> FEATURE:
<223> OTHER INFORMATION: Synthetic

<400> SEQUENCE: 76

Gly Val Ser Gln Ser Pro Ser Asn Lys Val Thr Glu Lys Gly Lys Asp
1               5                   10                  15

Val Glu Leu Arg Cys Asp Pro Ile Ser Gly His Thr Ala Leu Tyr Trp
            20                  25                  30

Tyr Arg Gln Ser Leu Gly Gln Gly Leu Glu Phe Leu Ile Tyr Phe Gln
        35                  40                  45

Gly Asn Ser Ala Pro Asp Lys Ser Gly Leu Pro Ser Asp Arg Phe Ser
    50                  55                  60

Ala Glu Arg Thr Gly Gly Ser Val Ser Thr Leu Thr Ile Gln Arg Thr
65                  70                  75                  80

Gln Gln Glu Asp Ser Ala Val Tyr Leu Cys Ala Ser Ser Leu Gly Gly
                85                  90                  95

Ser Ser Glu Thr Gln Tyr Phe Gly Pro Gly Thr Arg Leu Leu Val Leu
            100                 105                 110

Glu Asp Leu Arg Asn Val Thr Pro Pro Lys Val Ser Leu Phe Glu Pro
        115                 120                 125

Ser Lys Ala Glu Ile Ala Asn Lys Gln Lys Ala Thr Leu Val Cys Leu
    130                 135                 140

Ala Arg Gly Phe Phe Pro Asp His Val Glu Leu Ser Trp Trp Val Asn
145                 150                 155                 160

Gly Lys Glu Val His Ser Gly Val Cys Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
        195                 200                 205

His Gly Leu Ser Glu Glu Asp Lys Trp Pro Glu Gly Ser Pro Lys Pro
    210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
            260                 265                 270

Thr Leu Val Val Met Ala Met Val Lys Arg Lys Asn Ser
        275                 280                 285


<210> SEQ ID NO 77
<211> LENGTH: 611
<212> TYPE: PRT
<213> ORGANISM: Artificial Sequence
<220> FEATURE:
<223> OTHER INFORMATION: Synthetic
```

<400> SEQUENCE: 77

Met Ala Thr Arg Leu Leu Phe Trp Val Ala Phe Cys Leu Leu Gly Ala
1 5 10 15

Asp His Thr Gly Ala Gly Val Ser Gln Ser Pro Ser Asn Lys Val Thr
20 25 30

Glu Lys Gly Lys Asp Val Glu Leu Arg Cys Asp Pro Ile Ser Gly His
35 40 45

Thr Ala Leu Tyr Trp Tyr Arg Gln Ser Leu Gly Gln Gly Leu Glu Phe
50 55 60

Leu Ile Tyr Phe Gln Gly Asn Ser Ala Pro Asp Lys Ser Gly Leu Pro
65 70 75 80

Ser Asp Arg Phe Ser Ala Glu Arg Thr Gly Gly Ser Val Ser Thr Leu
85 90 95

Thr Ile Gln Arg Thr Gln Gln Glu Asp Ser Ala Val Tyr Leu Cys Ala
100 105 110

Ser Ser Leu Gly Gly Ser Ser Glu Thr Gln Tyr Phe Gly Pro Gly Thr
115 120 125

Arg Leu Leu Val Leu Glu Asp Leu Arg Asn Val Thr Pro Pro Lys Val
130 135 140

Ser Leu Phe Glu Pro Ser Lys Ala Glu Ile Ala Asn Lys Gln Lys Ala
145 150 155 160

Thr Leu Val Cys Leu Ala Arg Gly Phe Phe Pro Asp His Val Glu Leu
165 170 175

Ser Trp Trp Val Asn Gly Lys Glu Val His Ser Gly Val Cys Thr Asp
180 185 190

Pro Gln Ala Tyr Lys Glu Ser Asn Tyr Ser Tyr Cys Leu Ser Ser Arg
195 200 205

Leu Arg Val Ser Ala Thr Phe Trp His Asn Pro Arg Asn His Phe Arg
210 215 220

Cys Gln Val Gln Phe His Gly Leu Ser Glu Glu Asp Lys Trp Pro Glu
225 230 235 240

Gly Ser Pro Lys Pro Val Thr Gln Asn Ile Ser Ala Glu Ala Trp Gly
245 250 255

Arg Ala Asp Cys Gly Ile Thr Ser Ala Ser Tyr Gln Gln Gly Val Leu
260 265 270

Ser Ala Thr Ile Leu Tyr Glu Ile Leu Leu Gly Lys Ala Thr Leu Tyr
275 280 285

Ala Val Leu Val Ser Thr Leu Val Val Met Ala Met Val Lys Arg Lys
290 295 300

Asn Ser Arg Ala Lys Arg Ser Gly Ser Gly Ala Thr Asn Phe Ser Leu
305 310 315 320

Leu Lys Gln Ala Gly Asp Val Glu Glu Asn Pro Gly Pro Met His Lys
325 330 335

Ile Leu Gly Ala Ser Phe Leu Val Leu Trp Leu Gln Leu Cys Trp Val
340 345 350

Ser Gly Gln Gln Lys Glu Lys Ser Asp Gln Gln Gln Val Lys Gln Ser
355 360 365

Pro Gln Ser Leu Ile Val Gln Lys Gly Gly Ile Ser Ile Ile Asn Cys
370 375 380

Ala Tyr Glu Asn Thr Ala Phe Asp Tyr Phe Pro Trp Tyr Gln Gln Phe
385 390 395 400

Pro Gly Lys Gly Pro Ala Leu Leu Ile Ala Ile Arg Pro Asp Val Ser

```
                405                 410                 415

Glu Lys Lys Glu Gly Arg Phe Thr Ile Ser Phe Asn Lys Ser Ala Lys
            420                 425                 430

Gln Phe Ser Leu His Ile Met Asp Ser Gln Pro Gly Asp Ser Ala Thr
        435                 440                 445

Tyr Phe Cys Ala Ala Lys Arg Gln Gly Gly Ser Glu Lys Leu Val Phe
    450                 455                 460

Gly Lys Gly Thr Lys Leu Thr Val Asn Pro Asn Ile Gln Asn Pro Glu
465                 470                 475                 480

Pro Ala Val Tyr Gln Leu Lys Asp Pro Arg Ser Gln Asp Ser Thr Leu
                485                 490                 495

Cys Leu Phe Thr Asp Phe Asp Ser Gln Ile Asn Val Pro Lys Thr Met
            500                 505                 510

Glu Ser Gly Thr Phe Ile Thr Asp Lys Cys Val Leu Asp Met Lys Ala
        515                 520                 525

Met Asp Ser Lys Ser Asn Gly Ala Ile Ala Trp Ser Asn Gln Thr Ser
    530                 535                 540

Phe Thr Cys Gln Asp Ile Phe Lys Glu Thr Asn Ala Thr Tyr Pro Ser
545                 550                 555                 560

Ser Asp Val Pro Cys Asp Ala Thr Leu Thr Glu Lys Ser Phe Glu Thr
                565                 570                 575

Asp Met Asn Leu Asn Phe Gln Asn Leu Leu Val Ile Val Leu Arg Ile
            580                 585                 590

Leu Leu Leu Lys Val Ala Gly Phe Asn Leu Leu Met Thr Leu Arg Leu
        595                 600                 605

Trp Ser Ser
    610


<210> SEQ ID NO 78
<211> LENGTH: 6
<212> TYPE: PRT
<213> ORGANISM: Homo sapiens

<400> SEQUENCE: 78

Asn Ser Ala Ser Asp Tyr
1               5


<210> SEQ ID NO 79
<211> LENGTH: 7
<212> TYPE: PRT
<213> ORGANISM: Homo sapiens

<400> SEQUENCE: 79

Ile Arg Ser Asn Met Asp Lys
1               5


<210> SEQ ID NO 80
<211> LENGTH: 14
<212> TYPE: PRT
<213> ORGANISM: Homo sapiens

<400> SEQUENCE: 80

Cys Ala Glu Lys Arg Arg Gly Gly Ser Glu Lys Leu Val Phe
1               5                   10


<210> SEQ ID NO 81
<211> LENGTH: 5
<212> TYPE: PRT
<213> ORGANISM: Homo sapiens
```

<400> SEQUENCE: 81

Ser Gly His Thr Ala
1 5

<210> SEQ ID NO 82
<211> LENGTH: 6
<212> TYPE: PRT
<213> ORGANISM: Homo sapiens

<400> SEQUENCE: 82

Phe Gln Gly Thr Gly Ala
1 5

<210> SEQ ID NO 83
<211> LENGTH: 14
<212> TYPE: PRT
<213> ORGANISM: Homo sapiens

<400> SEQUENCE: 83

Cys Ala Ser Ser Pro Gly Gly Ser Gln Glu Thr Gln Tyr Phe
1 5 10

<210> SEQ ID NO 84
<211> LENGTH: 112
<212> TYPE: PRT
<213> ORGANISM: Homo sapiens

<400> SEQUENCE: 84

Glu Ser Val Gly Leu His Leu Pro Thr Leu Ser Val Gln Glu Gly Asp
1 5 10 15

Asn Ser Ile Ile Asn Cys Ala Tyr Ser Asn Ser Ala Ser Asp Tyr Phe
20 25 30

Ile Trp Tyr Lys Gln Glu Ser Gly Lys Gly Pro Gln Phe Ile Ile Asp
35 40 45

Ile Arg Ser Asn Met Asp Lys Arg Gln Gly Gln Arg Val Thr Val Leu
50 55 60

Leu Asn Lys Thr Val Lys His Leu Ser Leu Gln Ile Ala Ala Thr Gln
65 70 75 80

Pro Gly Asp Ser Ala Val Tyr Phe Cys Ala Glu Lys Arg Arg Gly Gly
85 90 95

Ser Glu Lys Leu Val Phe Gly Lys Gly Thr Lys Leu Thr Val Asn Pro
100 105 110

<210> SEQ ID NO 85
<211> LENGTH: 112
<212> TYPE: PRT
<213> ORGANISM: Homo sapiens

<400> SEQUENCE: 85

Gly Val Ser Gln Thr Pro Ser Asn Lys Val Thr Glu Lys Gly Lys Tyr
1 5 10 15

Val Glu Leu Arg Cys Asp Pro Ile Ser Gly His Thr Ala Leu Tyr Trp
20 25 30

Tyr Arg Gln Ser Leu Gly Gln Gly Pro Glu Phe Leu Ile Tyr Phe Gln
35 40 45

Gly Thr Gly Ala Ala Asp Asp Ser Gly Leu Pro Asn Asp Arg Phe Phe
50 55 60

Ala Val Arg Pro Glu Gly Ser Val Ser Thr Leu Lys Ile Gln Arg Thr
65 70 75 80

```
Glu Arg Gly Asp Ser Ala Val Tyr Leu Cys Ala Ser Ser Pro Gly Gly
                85                  90                  95

Ser Gln Glu Thr Gln Tyr Phe Gly Pro Gly Thr Arg Leu Leu Val Leu
            100                 105                 110


<210> SEQ ID NO 86
<211> LENGTH: 133
<212> TYPE: PRT
<213> ORGANISM: Artificial Sequence
<220> FEATURE:
<223> OTHER INFORMATION: Synthetic

<400> SEQUENCE: 86

Met His Gly Ile Arg Ala Leu Phe Met Tyr Leu Trp Leu Gln Leu Asp
1               5                   10                  15

Trp Val Ser Arg Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Glu Ser Gly Lys Gly Pro
    50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Lys Arg Arg Gly Gly Ser Glu Lys Leu Val Phe Gly Lys Gly Thr Lys
        115                 120                 125

Leu Thr Val Asn Pro
    130


<210> SEQ ID NO 87
<211> LENGTH: 133
<212> TYPE: PRT
<213> ORGANISM: Artificial Sequence
<220> FEATURE:
<223> OTHER INFORMATION: Synthetic

<400> SEQUENCE: 87

Met Ala Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
        35                  40                  45

Thr Ala Leu Tyr Trp Tyr Arg Gln Ser Leu Gly Gln Gly Pro Glu Phe
    50                  55                  60

Leu Ile Tyr Phe Gln Gly Thr Gly Ala Ala Asp Asp Ser Gly Leu Pro
65                  70                  75                  80

Asn Asp Arg Phe Phe Ala Val Arg Pro Glu Gly Ser Val Ser Thr Leu
                85                  90                  95

Lys Ile Gln Arg Thr Glu Arg Gly Asp Ser Ala Val Tyr Leu Cys Ala
            100                 105                 110

Ser Ser Pro Gly Gly Ser Gln Glu Thr Gln Tyr Phe Gly Pro Gly Thr
        115                 120                 125

Arg Leu Leu Val Leu
```

130

<210> SEQ ID NO 88
<211> LENGTH: 133
<212> TYPE: PRT
<213> ORGANISM: Homo sapiens

<400> SEQUENCE: 88

```
Met Ala Gly Ile Arg Ala Leu Phe Met Tyr Leu Trp Leu Gln Leu Asp
1               5                   10                  15

Trp Val Ser Arg Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Glu Ser Gly Lys Gly Pro
    50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Lys Arg Arg Gly Gly Ser Glu Lys Leu Val Phe Gly Lys Gly Thr Lys
        115                 120                 125

Leu Thr Val Asn Pro
    130
```

<210> SEQ ID NO 89
<211> LENGTH: 133
<212> TYPE: PRT
<213> ORGANISM: Homo sapiens

<400> SEQUENCE: 89

```
Met Gly Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
        35                  40                  45

Thr Ala Leu Tyr Trp Tyr Arg Gln Ser Leu Gly Gln Gly Pro Glu Phe
    50                  55                  60

Leu Ile Tyr Phe Gln Gly Thr Gly Ala Ala Asp Asp Ser Gly Leu Pro
65                  70                  75                  80

Asn Asp Arg Phe Phe Ala Val Arg Pro Glu Gly Ser Val Ser Thr Leu
                85                  90                  95

Lys Ile Gln Arg Thr Glu Arg Gly Asp Ser Ala Val Tyr Leu Cys Ala
            100                 105                 110

Ser Ser Pro Gly Gly Ser Gln Glu Thr Gln Tyr Phe Gly Pro Gly Thr
        115                 120                 125

Arg Leu Leu Val Leu
    130
```

<210> SEQ ID NO 90
<211> LENGTH: 270
<212> TYPE: PRT
<213> ORGANISM: Artificial Sequence
<220> FEATURE:
<223> OTHER INFORMATION: Synthetic

<400> SEQUENCE: 90

Met His Gly Ile Arg Ala Leu Phe Met Tyr Leu Trp Leu Gln Leu Asp
1               5                   10                  15

Trp Val Ser Arg Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Glu Ser Gly Lys Gly Pro
    50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Lys Arg Arg Gly Gly Ser Glu Lys Leu Val Phe Gly Lys Gly Thr Lys
        115                 120                 125

Leu Thr Val Asn Pro Asn Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Cys Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Leu Val Ile Val Leu Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 91
<211> LENGTH: 306
<212> TYPE: PRT
<213> ORGANISM: Artificial Sequence
<220> FEATURE:
<223> OTHER INFORMATION: Synthetic

<400> SEQUENCE: 91

Met Ala Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
        35                  40                  45

Thr Ala Leu Tyr Trp Tyr Arg Gln Ser Leu Gly Gln Gly Pro Glu Phe
    50                  55                  60

Leu Ile Tyr Phe Gln Gly Thr Gly Ala Ala Asp Asp Ser Gly Leu Pro
65                  70                  75                  80

-continued

```
Asn Asp Arg Phe Phe Ala Val Arg Pro Glu Gly Ser Val Ser Thr Leu
            85                  90                  95

Lys Ile Gln Arg Thr Glu Arg Gly Asp Ser Ala Val Tyr Leu Cys Ala
            100                 105                 110

Ser Ser Pro Gly Gly Ser Gln Glu Thr Gln Tyr Phe Gly Pro Gly Thr
        115                 120                 125

Arg Leu Leu Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300

Asn Ser
305
```

<210> SEQ ID NO 92
<211> LENGTH: 270
<212> TYPE: PRT
<213> ORGANISM: Artificial Sequence
<220> FEATURE:
<223> OTHER INFORMATION: Synthetic

<400> SEQUENCE: 92

```
Met Ala Gly Ile Arg Ala Leu Phe Met Tyr Leu Trp Leu Gln Leu Asp
1               5                   10                  15

Trp Val Ser Arg Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Glu Ser Gly Lys Gly Pro
    50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Lys Arg Arg Gly Gly Ser Glu Lys Leu Val Phe Gly Lys Gly Thr Lys
        115                 120                 125
```

-continued

```
Leu Thr Val Asn Pro Asn Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Cys Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240

Phe Gln Asn Leu Leu Val Ile Val Leu Arg Ile Leu Leu Leu Lys Val
                245                 250                 255

Ala Gly Phe Asn Leu Leu Met Thr Leu Arg Leu Trp Ser Ser
            260                 265                 270


<210> SEQ ID NO 93
<211> LENGTH: 306
<212> TYPE: PRT
<213> ORGANISM: Artificial Sequence
<220> FEATURE:
<223> OTHER INFORMATION: Synthetic

<400> SEQUENCE: 93

Met Gly Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
        35                  40                  45

Thr Ala Leu Tyr Trp Tyr Arg Gln Ser Leu Gly Gln Gly Pro Glu Phe
    50                  55                  60

Leu Ile Tyr Phe Gln Gly Thr Gly Ala Ala Asp Asp Ser Gly Leu Pro
65                  70                  75                  80

Asn Asp Arg Phe Phe Ala Val Arg Pro Glu Gly Ser Val Ser Thr Leu
                85                  90                  95

Lys Ile Gln Arg Thr Glu Arg Gly Asp Ser Ala Val Tyr Leu Cys Ala
            100                 105                 110

Ser Ser Pro Gly Gly Ser Gln Glu Thr Gln Tyr Phe Gly Pro Gly Thr
        115                 120                 125

Arg Leu Leu Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220
```

-continued

```
Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300

Asn Ser
305


<210> SEQ ID NO 94
<211> LENGTH: 249
<212> TYPE: PRT
<213> ORGANISM: Artificial Sequence
<220> FEATURE:
<223> OTHER INFORMATION: Synthetic

<400> SEQUENCE: 94

Glu Ser Val Gly Leu His Leu Pro Thr Leu Ser Val Gln Glu Gly Asp
1               5                   10                  15

Asn Ser Ile Ile Asn Cys Ala Tyr Ser Asn Ser Ala Ser Asp Tyr Phe
            20                  25                  30

Ile Trp Tyr Lys Gln Glu Ser Gly Lys Gly Pro Gln Phe Ile Ile Asp
        35                  40                  45

Ile Arg Ser Asn Met Asp Lys Arg Gln Gly Gln Arg Val Thr Val Leu
    50                  55                  60

Leu Asn Lys Thr Val Lys His Leu Ser Leu Gln Ile Ala Ala Thr Gln
65                  70                  75                  80

Pro Gly Asp Ser Ala Val Tyr Phe Cys Ala Glu Lys Arg Arg Gly Gly
                85                  90                  95

Ser Glu Lys Leu Val Phe Gly Lys Gly Thr Lys Leu Thr Val Asn Pro
            100                 105                 110

Asn Ile Gln Asn Pro Glu Pro Ala Val Tyr Gln Leu Lys Asp Pro Arg
        115                 120                 125

Ser Gln Asp Ser Thr Leu Cys Leu Phe Thr Asp Phe Asp Ser Gln Ile
    130                 135                 140

Asn Val Pro Lys Thr Met Glu Ser Gly Thr Phe Ile Thr Asp Lys Cys
145                 150                 155                 160

Val Leu Asp Met Lys Ala Met Asp Ser Lys Ser Asn Gly Ala Ile Ala
                165                 170                 175

Trp Ser Asn Gln Thr Ser Phe Thr Cys Gln Asp Ile Phe Lys Glu Thr
            180                 185                 190

Asn Ala Thr Tyr Pro Ser Ser Asp Val Pro Cys Asp Ala Thr Leu Thr
        195                 200                 205

Glu Lys Ser Phe Glu Thr Asp Met Asn Leu Asn Phe Gln Asn Leu Leu
    210                 215                 220

Val Ile Val Leu Arg Ile Leu Leu Leu Lys Val Ala Gly Phe Asn Leu
225                 230                 235                 240

Leu Met Thr Leu Arg Leu Trp Ser Ser
                245


<210> SEQ ID NO 95
<211> LENGTH: 285
```

<212> TYPE: PRT
<213> ORGANISM: Artificial Sequence
<220> FEATURE:
<223> OTHER INFORMATION: Synthetic

<400> SEQUENCE: 95

```
Gly Val Ser Gln Thr Pro Ser Asn Lys Val Thr Glu Lys Gly Lys Tyr
1               5                   10                  15

Val Glu Leu Arg Cys Asp Pro Ile Ser Gly His Thr Ala Leu Tyr Trp
            20                  25                  30

Tyr Arg Gln Ser Leu Gly Gln Gly Pro Glu Phe Leu Ile Tyr Phe Gln
        35                  40                  45

Gly Thr Gly Ala Ala Asp Asp Ser Gly Leu Pro Asn Asp Arg Phe Phe
    50                  55                  60

Ala Val Arg Pro Glu Gly Ser Val Ser Thr Leu Lys Ile Gln Arg Thr
65                  70                  75                  80

Glu Arg Gly Asp Ser Ala Val Tyr Leu Cys Ala Ser Ser Pro Gly Gly
                85                  90                  95

Ser Gln Glu Thr Gln Tyr Phe Gly Pro Gly Thr Arg Leu Leu Val Leu
            100                 105                 110

Glu Asp Leu Arg Asn Val Thr Pro Pro Lys Val Ser Leu Phe Glu Pro
        115                 120                 125

Ser Lys Ala Glu Ile Ala Asn Lys Gln Lys Ala Thr Leu Val Cys Leu
    130                 135                 140

Ala Arg Gly Phe Phe Pro Asp His Val Glu Leu Ser Trp Trp Val Asn
145                 150                 155                 160

Gly Lys Glu Val His Ser Gly Val Cys Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
        195                 200                 205

His Gly Leu Ser Glu Glu Asp Lys Trp Pro Glu Gly Ser Pro Lys Pro
    210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
            260                 265                 270

Thr Leu Val Val Met Ala Met Val Lys Arg Lys Asn Ser
        275                 280                 285
```

<210> SEQ ID NO 96
<211> LENGTH: 603
<212> TYPE: PRT
<213> ORGANISM: Artificial Sequence
<220> FEATURE:
<223> OTHER INFORMATION: Synthetic

<400> SEQUENCE: 96

```
Met Ala Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
        35                  40                  45
```

-continued

```
Thr Ala Leu Tyr Trp Tyr Arg Gln Ser Leu Gly Gln Gly Pro Glu Phe
    50                  55                  60

Leu Ile Tyr Phe Gln Gly Thr Gly Ala Ala Asp Asp Ser Gly Leu Pro
65                  70                  75                  80

Asn Asp Arg Phe Phe Ala Val Arg Pro Glu Gly Ser Val Ser Thr Leu
                85                  90                  95

Lys Ile Gln Arg Thr Glu Arg Gly Asp Ser Ala Val Tyr Leu Cys Ala
            100                 105                 110

Ser Ser Pro Gly Gly Ser Gln Glu Thr Gln Tyr Phe Gly Pro Gly Thr
        115                 120                 125

Arg Leu Leu Val Leu Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300

Asn Ser Arg Ala Lys Arg Ser Gly Ser Gly Ala Thr Asn Phe Ser Leu
305                 310                 315                 320

Leu Lys Gln Ala Gly Asp Val Glu Glu Asn Pro Gly Pro Met His Gly
                325                 330                 335

Ile Arg Ala Leu Phe Met Tyr Leu Trp Leu Gln Leu Asp Trp Val Ser
            340                 345                 350

Arg Gly Glu Ser Val Gly Leu His Leu Pro Thr Leu Ser Val Gln Glu
        355                 360                 365

Gly Asp Asn Ser Ile Ile Asn Cys Ala Tyr Ser Asn Ser Ala Ser Asp
    370                 375                 380

Tyr Phe Ile Trp Tyr Lys Gln Glu Ser Gly Lys Gly Pro Gln Phe Ile
385                 390                 395                 400

Ile Asp Ile Arg Ser Asn Met Asp Lys Arg Gln Gly Gln Arg Val Thr
                405                 410                 415

Val Leu Leu Asn Lys Thr Val Lys His Leu Ser Leu Gln Ile Ala Ala
            420                 425                 430

Thr Gln Pro Gly Asp Ser Ala Val Tyr Phe Cys Ala Glu Lys Arg Arg
        435                 440                 445

Gly Gly Ser Glu Lys Leu Val Phe Gly Lys Gly Thr Lys Leu Thr Val
    450                 455                 460
```

```
Asn Pro Asn Ile Gln Asn Pro Glu Pro Ala Val Tyr Gln Leu Lys Asp
465                 470                 475                 480

Pro Arg Ser Gln Asp Ser Thr Leu Cys Leu Phe Thr Asp Phe Asp Ser
                485                 490                 495

Gln Ile Asn Val Pro Lys Thr Met Glu Ser Gly Thr Phe Ile Thr Asp
            500                 505                 510

Lys Cys Val Leu Asp Met Lys Ala Met Asp Ser Lys Ser Asn Gly Ala
        515                 520                 525

Ile Ala Trp Ser Asn Gln Thr Ser Phe Thr Cys Gln Asp Ile Phe Lys
    530                 535                 540

Glu Thr Asn Ala Thr Tyr Pro Ser Ser Asp Val Pro Cys Asp Ala Thr
545                 550                 555                 560

Leu Thr Glu Lys Ser Phe Glu Thr Asp Met Asn Leu Asn Phe Gln Asn
                565                 570                 575

Leu Leu Val Ile Val Leu Arg Ile Leu Leu Leu Lys Val Ala Gly Phe
            580                 585                 590

Asn Leu Leu Met Thr Leu Arg Leu Trp Ser Ser
        595                 600


<210> SEQ ID NO 97
<211> LENGTH: 137
<212> TYPE: PRT
<213> ORGANISM: Artificial Sequence
<220> FEATURE:
<223> OTHER INFORMATION: Synthetic

<400> SEQUENCE: 97

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 98
<211> LENGTH: 137
<212> TYPE: PRT
<213> ORGANISM: Artificial Sequence
<220> FEATURE:
<223> OTHER INFORMATION: Synthetic

<400> SEQUENCE: 98

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30
```

```
Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 99
<211> LENGTH: 173
<212> TYPE: PRT
<213> ORGANISM: Artificial Sequence
<220> FEATURE:
<223> OTHER INFORMATION: Synthetic

<400> SEQUENCE: 99

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Cys Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170


<210> SEQ ID NO 100
<211> LENGTH: 27
<212> TYPE: PRT
<213> ORGANISM: Artificial Sequence
<220> FEATURE:
<223> OTHER INFORMATION: Synthetic

<400> SEQUENCE: 100

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
```

```
            20                  25


<210> SEQ ID NO 101
<211> LENGTH: 341
<212> TYPE: PRT
<213> ORGANISM: Homo sapiens

<400> SEQUENCE: 101

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Asp Gln Thr Ser Phe
                325                 330                 335

Gln Lys Glu Asn Cys
            340


<210> SEQ ID NO 102
<211> LENGTH: 346
```

```
<212> TYPE: PRT
<213> ORGANISM: Homo sapiens

<400> SEQUENCE: 102

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Met Leu Leu Asp Leu
                325                 330                 335

Arg Trp Cys Tyr Phe Leu Ile Asn Ser Ser
            340                 345


<210> SEQ ID NO 103
<211> LENGTH: 354
<212> TYPE: PRT
<213> ORGANISM: Homo sapiens

<400> SEQUENCE: 103
```

-continued

```
Met Asp Asp Leu Met Leu Ser Pro Asp Asp Ile Glu Gln Trp Phe Thr
1               5                   10                  15

Glu Asp Pro Gly Pro Asp Glu Ala Pro Arg Met Pro Glu Ala Ala Pro
            20                  25                  30

Pro Val Ala Pro Ala Pro Ala Ala Pro Thr Pro Ala Ala Pro Ala Pro
        35                  40                  45

Ala Pro Ser Trp Pro Leu Ser Ser Ser Val Pro Ser Gln Lys Thr Tyr
    50                  55                  60

Gln Gly Ser Tyr Gly Phe Arg Leu Gly Phe Leu His Ser Gly Thr Ala
65                  70                  75                  80

Lys Ser Val Thr Cys Thr Tyr Ser Pro Ala Leu Asn Lys Met Phe Cys
                85                  90                  95

Gln Leu Ala Lys Thr Cys Pro Val Gln Leu Trp Val Asp Ser Thr Pro
            100                 105                 110

Pro Pro Gly Thr Arg Val Arg Ala Met Ala Ile Tyr Lys Gln Ser Gln
        115                 120                 125

His Met Thr Glu Val Val Arg Arg Cys Pro His His Glu Arg Cys Ser
    130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                165                 170                 175

Val Val Val Pro Tyr Glu Pro Pro Glu Val Gly Ser Asp Cys Thr Thr
            180                 185                 190

Ile His Tyr Asn Tyr Met Cys Asn Ser Ser Cys Met Gly Gly Met Asn
        195                 200                 205

Arg Arg Pro Ile Leu Thr Ile Ile Thr Leu Glu Asp Ser Ser Gly Asn
    210                 215                 220

Leu Leu Gly Arg Asn Ser Phe Glu Val Arg Val Cys Ala Cys Pro Gly
225                 230                 235                 240

Arg Asp Arg Arg Thr Glu Glu Glu Asn Leu Arg Lys Lys Gly Glu Pro
                245                 250                 255

His His Glu Leu Pro Pro Gly Ser Thr Lys Arg Ala Leu Pro Asn Asn
            260                 265                 270

Thr Ser Ser Ser Pro Gln Pro Lys Lys Lys Pro Leu Asp Gly Glu Tyr
        275                 280                 285

Phe Thr Leu Gln Ile Arg Gly Arg Glu Arg Phe Glu Met Phe Arg Glu
    290                 295                 300

Leu Asn Glu Ala Leu Glu Leu Lys Asp Ala Gln Ala Gly Lys Glu Pro
305                 310                 315                 320

Gly Gly Ser Arg Ala His Ser Ser His Leu Lys Ser Lys Lys Gly Gln
                325                 330                 335

Ser Thr Ser Arg His Lys Lys Leu Met Phe Lys Thr Glu Gly Pro Asp
            340                 345                 350

Ser Asp


<210> SEQ ID NO 104
<211> LENGTH: 302
<212> TYPE: PRT
<213> ORGANISM: Homo sapiens

<400> SEQUENCE: 104

Met Asp Asp Leu Met Leu Ser Pro Asp Asp Ile Glu Gln Trp Phe Thr
1               5                   10                  15
```

-continued

```
Glu Asp Pro Gly Pro Asp Glu Ala Pro Arg Met Pro Glu Ala Ala Pro
            20                  25                  30

Pro Val Ala Pro Ala Pro Ala Ala Pro Thr Pro Ala Ala Pro Ala Pro
        35                  40                  45

Ala Pro Ser Trp Pro Leu Ser Ser Ser Val Pro Ser Gln Lys Thr Tyr
    50                  55                  60

Gln Gly Ser Tyr Gly Phe Arg Leu Gly Phe Leu His Ser Gly Thr Ala
65                  70                  75                  80

Lys Ser Val Thr Cys Thr Tyr Ser Pro Ala Leu Asn Lys Met Phe Cys
                85                  90                  95

Gln Leu Ala Lys Thr Cys Pro Val Gln Leu Trp Val Asp Ser Thr Pro
            100                 105                 110

Pro Pro Gly Thr Arg Val Arg Ala Met Ala Ile Tyr Lys Gln Ser Gln
        115                 120                 125

His Met Thr Glu Val Val Arg Arg Cys Pro His His Glu Arg Cys Ser
    130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                165                 170                 175

Val Val Val Pro Tyr Glu Pro Pro Glu Val Gly Ser Asp Cys Thr Thr
            180                 185                 190

Ile His Tyr Asn Tyr Met Cys Asn Ser Ser Cys Met Gly Gly Met Asn
        195                 200                 205

Arg Arg Pro Ile Leu Thr Ile Ile Thr Leu Glu Asp Ser Ser Gly Asn
    210                 215                 220

Leu Leu Gly Arg Asn Ser Phe Glu Val Arg Val Cys Ala Cys Pro Gly
225                 230                 235                 240

Arg Asp Arg Arg Thr Glu Glu Glu Asn Leu Arg Lys Lys Gly Glu Pro
                245                 250                 255

His His Glu Leu Pro Pro Gly Ser Thr Lys Arg Ala Leu Pro Asn Asn
            260                 265                 270

Thr Ser Ser Ser Pro Gln Pro Lys Lys Lys Pro Leu Asp Gly Glu Tyr
        275                 280                 285

Phe Thr Leu Gln Asp Gln Thr Ser Phe Gln Lys Glu Asn Cys
    290                 295                 300


<210> SEQ ID NO 105
<211> LENGTH: 307
<212> TYPE: PRT
<213> ORGANISM: Homo sapiens

<400> SEQUENCE: 105

Met Asp Asp Leu Met Leu Ser Pro Asp Asp Ile Glu Gln Trp Phe Thr
1               5                   10                  15

Glu Asp Pro Gly Pro Asp Glu Ala Pro Arg Met Pro Glu Ala Ala Pro
            20                  25                  30

Pro Val Ala Pro Ala Pro Ala Ala Pro Thr Pro Ala Ala Pro Ala Pro
        35                  40                  45

Ala Pro Ser Trp Pro Leu Ser Ser Ser Val Pro Ser Gln Lys Thr Tyr
    50                  55                  60

Gln Gly Ser Tyr Gly Phe Arg Leu Gly Phe Leu His Ser Gly Thr Ala
65                  70                  75                  80

Lys Ser Val Thr Cys Thr Tyr Ser Pro Ala Leu Asn Lys Met Phe Cys
                85                  90                  95
```

```
Gln Leu Ala Lys Thr Cys Pro Val Gln Leu Trp Val Asp Ser Thr Pro
            100                 105                 110

Pro Pro Gly Thr Arg Val Arg Ala Met Ala Ile Tyr Lys Gln Ser Gln
        115                 120                 125

His Met Thr Glu Val Val Arg Arg Cys Pro His His Glu Arg Cys Ser
    130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                165                 170                 175

Val Val Val Pro Tyr Glu Pro Pro Glu Val Gly Ser Asp Cys Thr Thr
            180                 185                 190

Ile His Tyr Asn Tyr Met Cys Asn Ser Ser Cys Met Gly Gly Met Asn
        195                 200                 205

Arg Arg Pro Ile Leu Thr Ile Ile Thr Leu Glu Asp Ser Ser Gly Asn
    210                 215                 220

Leu Leu Gly Arg Asn Ser Phe Glu Val Arg Val Cys Ala Cys Pro Gly
225                 230                 235                 240

Arg Asp Arg Arg Thr Glu Glu Glu Asn Leu Arg Lys Lys Gly Glu Pro
                245                 250                 255

His His Glu Leu Pro Pro Gly Ser Thr Lys Arg Ala Leu Pro Asn Asn
            260                 265                 270

Thr Ser Ser Ser Pro Gln Pro Lys Lys Lys Pro Leu Asp Gly Glu Tyr
        275                 280                 285

Phe Thr Leu Gln Met Leu Leu Asp Leu Arg Trp Cys Tyr Phe Leu Ile
    290                 295                 300

Asn Ser Ser
305


<210> SEQ ID NO 106
<211> LENGTH: 261
<212> TYPE: PRT
<213> ORGANISM: Homo sapiens

<400> SEQUENCE: 106

Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
```

```
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Ile Arg Gly Arg Glu Arg Phe Glu Met
        195                 200                 205

Phe Arg Glu Leu Asn Glu Ala Leu Glu Leu Lys Asp Ala Gln Ala Gly
    210                 215                 220

Lys Glu Pro Gly Gly Ser Arg Ala His Ser Ser His Leu Lys Ser Lys
225                 230                 235                 240

Lys Gly Gln Ser Thr Ser Arg His Lys Lys Leu Met Phe Lys Thr Glu
                245                 250                 255

Gly Pro Asp Ser Asp
            260


<210> SEQ ID NO 107
<211> LENGTH: 209
<212> TYPE: PRT
<213> ORGANISM: Homo sapiens

<400> SEQUENCE: 107

Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Asp Gln Thr Ser Phe Gln Lys Glu Asn
        195                 200                 205

Cys


<210> SEQ ID NO 108
<211> LENGTH: 214
<212> TYPE: PRT
<213> ORGANISM: Homo sapiens

<400> SEQUENCE: 108
```

-continued

Met Phe Cys Gln Leu Ala Lys Thr Cys Pro Val Gln Leu Trp Val Asp
1               5                   10                  15

Ser Thr Pro Pro Pro Gly Thr Arg Val Arg Ala Met Ala Ile Tyr Lys
            20                  25                  30

Gln Ser Gln His Met Thr Glu Val Val Arg Arg Cys Pro His His Glu
        35                  40                  45

Arg Cys Ser Asp Ser Asp Gly Leu Ala Pro Pro Gln His Leu Ile Arg
    50                  55                  60

Val Glu Gly Asn Leu Arg Val Glu Tyr Leu Asp Asp Arg Asn Thr Phe
65                  70                  75                  80

Arg His Ser Val Val Val Pro Tyr Glu Pro Pro Glu Val Gly Ser Asp
                85                  90                  95

Cys Thr Thr Ile His Tyr Asn Tyr Met Cys Asn Ser Ser Cys Met Gly
            100                 105                 110

Gly Met Asn Arg Arg Pro Ile Leu Thr Ile Ile Thr Leu Glu Asp Ser
        115                 120                 125

Ser Gly Asn Leu Leu Gly Arg Asn Ser Phe Glu Val Arg Val Cys Ala
    130                 135                 140

Cys Pro Gly Arg Asp Arg Arg Thr Glu Glu Glu Asn Leu Arg Lys Lys
145                 150                 155                 160

Gly Glu Pro His His Glu Leu Pro Pro Gly Ser Thr Lys Arg Ala Leu
                165                 170                 175

Pro Asn Asn Thr Ser Ser Ser Pro Gln Pro Lys Lys Lys Pro Leu Asp
            180                 185                 190

Gly Glu Tyr Phe Thr Leu Gln Met Leu Leu Asp Leu Arg Trp Cys Tyr
        195                 200                 205

Phe Leu Ile Asn Ser Ser
    210

<210> SEQ ID NO 109
<211> LENGTH: 1797
<212> TYPE: DNA
<213> ORGANISM: Artificial Sequence
<220> FEATURE:
<223> OTHER INFORMATION: Synthetic

<400> SEQUENCE: 109
atggcgcccc agctgctggg ctacgtggtg ctgtgcctgc tgggagcagg accactggag 60
gcacaggtga cccagaaccc cagatatctg atcaccgtga caggcaagaa gctgaccgtg 120
acatgttccc agaacatgaa tcacgagtac atgtcttggt ataggcagga ccctggcctg 180
ggcctgaggc agatctacta ttctatgaat gtggaggtga cagacaaggg cgatgtgcct 240
gagggctaca aggtgagccg gaaggagaag agaaacttcc cactgatcct ggagtctccc 300
agccctaatc agaccagcct gtatttctgc gccagctcct ttatctccaa ccagccccag 360
cactttggcg atggcacaag gctgtccatc ctggaggatc tccggaatgt gacacccccct 420 aaggtgtctc tgttcgagcc aagcaaggcc gagatcgcca acaagcagaa ggccaccctg 480
gtgtgcctgg ccagaggctt ctttcccgat cacgtggagc tgtcctggtg ggtgaatggc 540
aaggaggtgc actctggcgt gtgcaccgac cctcaggcct ataaggagtc caactactct 600
tattgtctga gctcccggct gagagtgtcc gccacattct ggcacaatcc cagaaaccac 660
ttcagatgcc aggtgcagtt tcacggcctg tccgaggagg ataagtggcc tgagggctct 720
ccaaagcccg tgacccagaa tatcagcgcc gaggcatggg gaagggcaga ctgtggaatc 780
acctccgcct cttaccagca gggcgtgctg agcgccacaa tcctgtatga gatcctgctg 840
ggcaaggcca ccctgtacgc cgtgctggtg agcacactgg tggtcatggc tatggtgaag 900
aggaagaaca gccgggccaa gcgcagcggc tccggcgcaa ccaacttctc tctgctgaag 960
caggcaggcg acgtggagga gaatcctggc ccaatgcata agagcctgcg ggtgctgctg 1020
gtcatcctgt ggctccagct gtcttgggtg tggagccagc agaaggaggt ggagcaggac 1080
cccggccctc tgagcgtgcc tgagggagcc atcgtgtccc tgaactgcac ctactccaat 1140
tctgccttcc agtacttcat gtggtacagg cagtacagcc ggaagggccc cgagctgctg 1200
atgtacacct atagctccgg caacaaggag gacggcaggt tcacagccca ggtggataag 1260
tctagcaagt acatctccct gtttatccgc gactctcagc caagcgattc cgccacctac 1320
ctgtgcgcag gaggatccta tggcaagctg acattcggcc agggcaccat cctgacagtg 1380
caccccaata ttcagaatcc cgagcccgcg gtataccagc tgaaggaccc ccggagccag 1440
gatagcaccc tgtgcctgtt cacagacttt gattctcaga tcaacgtgcc caagacaatg 1500
gagagcggca cctttatcac agacaagtgc gtgctggaca tgaaggctat ggactctaag 1560
agcaatggcg ccatcgcctg gtccaaccag acctctttca catgccagga tatctttaag 1620
gagacaaatg ccacataccc cagctccgac gtgccttgtg atgccaccct gacagagaag 1680
agcttcgaga cagacatgaa tctgaacttt cagaacctgc tggtcatcgt gctgagaatc 1740
ctgctgctga aagtggctgg cttcaacctg ctgatgaccc tgcggctgtg gagtagc 1797

<210> SEQ ID NO 110
<211> LENGTH: 1800
<212> TYPE: DNA
<213> ORGANISM: Artificial Sequence
<220> FEATURE:
<223> OTHER INFORMATION: Synthetic

<400> SEQUENCE: 110
atggcgtgcc ggctgctgtg ctgtgccgtg ctgtgcctgc tgggagcagt gccaatggag 60
accggagtga cccagacacc caggcacctg gtcatgggca tgacaaacaa gaagtctctg 120
aagtgcgagc agcacctggg ccacaatgcc atgtactggt ataagcagtc cgccaagaag 180
cctctggagc tgatgttcgt gtactctctg gaggagcggg tggagaacaa ttccgtgcca 240
agccggttca gccccgagtg ccctaacagc tcccacctgt ttctgcacct gcacaccctc 300
cagccagagg acagcgccct gtacctgtgc gcctctagca gggtggaggg ctccgataca 360
cagtattttg gccctggcac ccgcctgaca gtgctggagg atctccggaa tgtgacaccc 420
cctaaggtgt ctctgttcga gccaagcaag gccgagatcg ccaacaagca gaaggccacc 480
ctggtgtgcc tggccagagg cttctttccc gatcacgtgg agctgtcctg gtgggtgaat 540
ggcaaggagg tgcactctgg cgtgtgcacc gaccctcagg cctataagga gtccaactac 600
tcttattgtc tgagctcccg gctgagagtg tccgccacat tctggcacaa tcccagaaac 660
cacttcagat gccaggtgca gtttcacggc ctgtccgagg aggataagtg gcctgagggc 720
tctccaaagc ccgtgaccca gaatatcagc gccgaggcat ggggaagggc agactgtgga 780
atcacctccg cctcttacca gcagggcgtg ctgagcgcca caatcctgta tgagatcctg 840
ctgggcaagg ccaccctgta cgccgtgctg gtgagcacac tggtggtcat ggctatggtg 900
aagaggaaga acagccgggc caagcgcagc ggctccggcg caaccaactt ctctctgctg 960
aagcaggcag gcgacgtgga ggagaatcct ggcccaatgc atggcatcag ggccctgttc 1020
atgtacctgt ggctccagct ggactgggtg agccggggcg agtccgtggg actgcacctg 1080
ccaaccctgt ctgtgcagga gggcgacaac agcatcatca attgcgccta tagcaactcc 1140
gcctctgatt acttcatctg gtataagcag gagagcggca agggccccca gtttatcatc 1200
gacatccggt ccaacatgga taagcggcag ggccagagag tgaccgtgct gctgaataag 1260
acagtgaagc acctgtctct ccagatcgca gcaacacagc ccggcgattc cgccgtgtac 1320
ttttgtgccg agaagtctac cggcaatcag ttctattttg gcaccggcac aagcctgaca 1380
gtgatcccta atattcagaa tcccgagccc gcggtatacc agctgaagga cccccggagc 1440
caggatagca ccctgtgcct gttcacagac tttgattctc agatcaacgt gcccaagaca 1500
atggagagcg gcacctttat cacagacaag tgcgtgctgg acatgaaggc tatggactct 1560
aagagcaatg gcgccatcgc ctggtccaac cagacctctt tcacatgcca ggatatcttt 1620
aaggagacaa atgccacata ccccagctcc gacgtgcctt gtgatgccac cctgacagag 1680
aagagcttcg agacagacat gaatctgaac tttcagaacc tgctggtcat cgtgctgaga 1740
atcctgctgc tgaaagtggc tggcttcaac ctgctgatga ccctgcggct gtggagtagc 1800

<210> SEQ ID NO 111
<211> LENGTH: 1809
<212> TYPE: DNA
<213> ORGANISM: Artificial Sequence
<220> FEATURE:
<223> OTHER INFORMATION: Synthetic

<400> SEQUENCE: 111
atggcgctgc tgctgctgct gctgggccct ggctctggcc tgggagcagt ggtgtcccag 60
caccctagca gagtgatctg caagtctggc acaagcgtga agatcgagtg taggagcctg 120
gacttccagg ccaccacaat gttctggtac cgccagtttc ccaagcagtc cctgatgctg 180
atggccacaa gcaacgaggg ctccaaggcc acctatgagc agggcgtgga gaaggataag 240
tttctgatca atcacgcctc tctgaccctg agcaccctga cagtgacctc cgcccaccca 300
gaggacagct ccttctacat ctgctccgcc atccgggata gatctggcgg cgagacacag 360
tattttggcc ctggcaccag gctgctggtg ctggaggatc tccggaatgt gacacccccct 420 aaggtgtctc tgttcgagcc aagcaaggcc gagatcgcca acaagcagaa ggccaccctg 480
gtgtgcctgg ccagaggctt ctttcccgat cacgtggagc tgtcctggtg ggtgaatggc 540
aaggaggtgc actctggcgt gtgcaccgac cctcaggcct ataaggagtc caactactct 600
tattgtctga gctcccggct gagagtgtcc gccacattct ggcacaatcc cagaaaccac 660
ttcagatgcc aggtgcagtt tcacggcctg tccgaggagg ataagtggcc tgagggctct 720
ccaaagcccg tgacccagaa tatcagcgcc gaggcatggg gaagggcaga ctgtggaatc 780
acctccgcct cttaccagca gggcgtgctg agcgccacaa tcctgtatga gatcctgctg 840
ggcaaggcca ccctgtacgc cgtgctggtg agcacactgg tggtcatggc tatggtgaag 900
aggaagaaca gccgggccaa gcgcagcggc tccggcgcaa ccaacttctc tctgctgaag 960
caggcaggcg acgtggagga gaatcctggc ccaatgcata gcgcccccat ctccatgctg 1020
gccatgctgt ttaccctgtc tggcctgagg gcacagagcg tggcacagcc agaggaccag 1080
gtgaacgtgg ccgagggcaa tcccctgacc gtgaagtgca catacagcgt gtccggcaac 1140
ccctatctgt tctggtacgt gcagtatcct aatcggggcc tccagttcct gctgaagtac 1200
atcaccggcg ataacctggt gaagggcagc tatggcttcg aggccgagtt taataagtcc 1260
cagacatctt tccacctgaa gaagccttcc gccctggtgt ctgacagcgc cctgtacttt 1320

-continued tgtgccgtgc gggatccaac cgtgtctggc acatacaagt atatcttcgg caccggcaca 1380
agactgaagg tgctggccaa tattcagaat cccgagcccg cggtatacca gctgaaggac 1440
ccccggagcc aggatagcac cctgtgcctg ttcacagact ttgattctca gatcaacgtg 1500
cccaagacaa tggagagcgg cacctttatc acagacaagt gcgtgctgga catgaaggct 1560
atggactcta agagcaatgg cgccatcgcc tggtccaacc agacctcttt cacatgccag 1620
gatatcttta aggagacaaa tgccacatac cccagctccg acgtgccttg tgatgccacc 1680
ctgacagaga agagcttcga gacagacatg aatctgaact ttcagaacct gctggtcatc 1740
gtgctgagaa tcctgctgct gaaagtggct ggcttcaacc tgctgatgac cctgcggctg 1800
tggagtagc 1809

<210> SEQ ID NO 112
<211> LENGTH: 1833
<212> TYPE: DNA
<213> ORGANISM: Artificial Sequence
<220> FEATURE:
<223> OTHER INFORMATION: Synthetic

<400> SEQUENCE: 112
atggcgaccc ggctgctgtt ctgggtggca ttttgcctgc tgggagcaga ccacaccgga 60
gcaggcgtgt cccagtctcc aagcaacaag gtgacagaga agggcaagga cgtggagctg 120
aggtgtgatc ccatcagcgg ccacacagcc ctgtactggt ataggcagtc cctgggacag 180
ggcctggagt tcctgatcta ctttcagggc aattctgccc ccgacaagag cggcctgcct 240
tccgatcggt tctctgccga gagaaccggc ggctccgtgt ctaccctgac aatccagcgg 300
acacagcagg aggattccgc cgtgtacctg tgcgccagct ccctgggagg atctagcgag 360
acccagtatt ttggccctgg cacaaggctg ctggtgctgg aggatctccg gaatgtgaca 420
ccccctaagg tgtctctgtt cgagccaagc aaggccgaga tcgccaacaa gcagaaggcc 480
accctggtgt gcctggccag aggcttcttt cccgatcacg tggagctgtc ctggtgggtg 540
aatggcaagg aggtgcactc tggcgtgtgc accgaccctc aggcctataa ggagtccaac 600
tactcttatt gtctgagctc ccggctgaga gtgtccgcca cattctggca caatcccaga 660
aaccacttca gatgccaggt gcagtttcac ggcctgtccg aggaggataa gtggcctgag 720
ggctctccaa agcccgtgac ccagaatatc agcgccgagg catggggaag ggcagactgt 780
ggaatcacct ccgcctctta ccagcagggc gtgctgagcg ccacaatcct gtatgagatc 840
ctgctgggca aggccaccct gtacgccgtg ctggtgagca cactggtggt catggctatg 900
gtgaagagga agaacagccg ggccaagcgc agcggctccg gcgcaaccaa cttctctctg 960
ctgaagcagg caggcgacgt ggaggagaat cctggcccaa tgcataagat cctgggcgcc 1020
tccttcctgg tgctgtggct ccagctgtgc tgggtgagcg gccagcagaa ggagaagtcc 1080
gaccagcagc aggtgaagca gagcccccag tccctgatcg tgcagaaggg cggcatctct 1140
atcatcaact gtgcctacga gaataccgcc ttcgactact ttccctggta tcagcagttc 1200
cccggcaagg gacctgccct gctgatcgca atccggcccg acgtgagcga gaagaaggag 1260
ggcagattca ccatctcttt taacaagagc gccaagcagt ttagcctgca catcatggac 1320
tcccagcctg gcgattctgc cacatatttc tgcgcagcaa agaggcaggg aggaagcgag 1380
aagctggtgt ttggcaaggg caccaagctg acagtgaatc caaatattca gaatcccgag 1440
cccgcggtat accagctgaa ggacccccgg agccaggata gcaccctgtg cctgttcaca 1500
gactttgatt ctcagatcaa cgtgcccaag acaatggaga gcggcacctt tatcacagac 1560

```
aagtgcgtgc tggacatgaa ggctatggac tctaagagca atggcgccat cgcctggtcc   1620

aaccagacct ctttcacatg ccaggatatc tttaaggaga caaatgccac ataccccagc   1680

tccgacgtgc cttgtgatgc caccctgaca gagaagagct tcgagacaga catgaatctg   1740

aactttcaga acctgctggt catcgtgctg agaatcctgc tgctgaaagt ggctggcttc   1800

aacctgctga tgaccctgcg gctgtggagt agc                                1833


<210> SEQ ID NO 113
<211> LENGTH: 1809
<212> TYPE: DNA
<213> ORGANISM: Artificial Sequence
<220> FEATURE:
<223> OTHER INFORMATION: Synthetic

<400> SEQUENCE: 113

atggcgacca ggctgctgtg ctgggccgcc ctgtgcctgc tgggagcaga ccacacagga     60

gcaggcgtgt cccagacccc ttctaacaag gtgacagaga agggcaagta cgtggagctg    120

cggtgcgatc caatcagcgg ccacaccgcc ctgtactggt atagacagtc cctgggacag    180

ggccccgagt tcctgatcta ttttcaggga acaggagccg ccgacgattc cggcctgccc    240

aatgacaggt tctttgccgt gcgccctgag ggatctgtga gcaccctgaa gatccagcgg    300

acagagagag gcgatagcgc cgtgtacctg tgcgccagct ccccaggcgg aagccaggag    360

acccagtatt tcggccctgg cacaagactg ctggtgctgg aggatctccg gaatgtgaca    420

ccccctaagg tgtctctgtt cgagccaagc aaggccgaga tcgccaacaa gcagaaggcc    480

accctggtgt gcctggccag aggcttcttt cccgatcacg tggagctgtc ctggtgggtg    540

aatggcaagg aggtgcactc tggcgtgtgc accgaccctc aggcctataa ggagtccaac    600

tactcttatt gtctgagctc ccggctgaga gtgtccgcca cattctggca caatcccaga    660

aaccacttca gatgccaggt gcagtttcac ggcctgtccg aggaggataa gtggcctgag    720

ggctctccaa agcccgtgac ccagaatatc agcgccgagg catggggaag ggcagactgt    780

ggaatcacct ccgcctctta ccagcagggc gtgctgagcg ccacaatcct gtatgagatc    840

ctgctgggca aggccaccct gtacgccgtg ctggtgagca cactggtggt catggctatg    900

gtgaagagga agaacagccg ggccaagcgc agcggctccg gcgcaaccaa cttctctctg    960

ctgaagcagg caggcgacgt ggaggagaat cctggcccaa tgcatggcat ccgggccctg   1020

ttcatgtacc tgtggctcca gctggactgg gtgagcaggg gcgagtccgt gggactgcac   1080

ctgccaaccc tgtctgtgca ggagggcgac aacagcatca tcaattgcgc ctatagcaac   1140

tccgcctctg attacttcat ctggtataag caggagagcg gcaagggccc ccagtttatc   1200

atcgacatcc ggtccaacat ggataagagg cagggacaga gggtgaccgt gctgctgaat   1260

aagacagtga agcacctgtc cctccagatc gcagcaacac agcccggcga ttctgccgtg   1320

tacttctgtg ccgagaagcg gagaggcggc tctgagaagc tggtgtttgg caagggcacc   1380

aagctgacag tgaatcctaa tattcagaat cccgagcccg cggtatacca gctgaaggac   1440

ccccggagcc aggatagcac cctgtgcctg ttcacagact ttgattctca gatcaacgtg   1500

cccaagacaa tggagagcgg cacctttatc acagacaagt gcgtgctgga catgaaggct   1560

atggactcta agagcaatgg cgccatcgcc tggtccaacc agacctcttt cacatgccag   1620

gatatcttta aggagacaaa tgccacatac cccagctccg acgtgccttg tgatgccacc   1680

ctgacagaga agagcttcga gacagacatg aatctgaact ttcagaacct gctggtcatc   1740
```

```
gtgctgagaa tcctgctgct gaaagtggct ggcttcaacc tgctgatgac cctgcggctg   1800

tggagtagc                                                           1809


<210> SEQ ID NO 114
<211> LENGTH: 25
<212> TYPE: PRT
<213> ORGANISM: Homo sapiens

<400> SEQUENCE: 114

Asp Arg Asn Thr Phe Arg His Ser Val Val Val Pro Tyr Glu Pro Pro
1               5                   10                  15

Glu Val Gly Ser Asp Cys Thr Thr Ile
            20                  25


<210> SEQ ID NO 115
<211> LENGTH: 25
<212> TYPE: PRT
<213> ORGANISM: Homo sapiens

<400> SEQUENCE: 115

Asp Arg Asn Thr Phe Arg His Ser Val Val Val Pro Cys Glu Pro Pro
1               5                   10                  15

Glu Val Gly Ser Asp Cys Thr Thr Ile
            20                  25


<210> SEQ ID NO 116
<211> LENGTH: 25
<212> TYPE: PRT
<213> ORGANISM: Homo sapiens

<400> SEQUENCE: 116

Ser Gly Asn Leu Leu Gly Arg Asn Ser Phe Glu Val Arg Val Cys Ala
1               5                   10                  15

Cys Pro Gly Arg Asp Arg Arg Thr Glu
            20                  25


<210> SEQ ID NO 117
<211> LENGTH: 25
<212> TYPE: PRT
<213> ORGANISM: Homo sapiens

<400> SEQUENCE: 117

Ser Gly Asn Leu Leu Gly Arg Asn Ser Phe Glu Val Cys Val Cys Ala
1               5                   10                  15

Cys Pro Gly Arg Asp Arg Arg Thr Glu
            20                  25


<210> SEQ ID NO 118
<211> LENGTH: 4
<212> TYPE: PRT
<213> ORGANISM: Artificial Sequence
<220> FEATURE:
<223> OTHER INFORMATION: Synthetic

<400> SEQUENCE: 118

Arg Ala Lys Arg
1


<210> SEQ ID NO 119
<211> LENGTH: 109
<212> TYPE: PRT
<213> ORGANISM: Homo sapiens
```

<400> SEQUENCE: 119

Gln Lys Glu Val Glu Gln Asp Pro Gly Pro Leu Ser Val Pro Glu Gly
1 5 10 15

Ala Ile Val Ser Leu Asn Cys Thr Tyr Ser Asn Ser Ala Phe Gln Tyr
20 25 30

Phe Met Trp Tyr Arg Gln Tyr Ser Arg Lys Gly Pro Glu Leu Leu Met
35 40 45

Tyr Thr Tyr Ser Ser Gly Asn Lys Glu Asp Gly Arg Phe Thr Ala Gln
50 55 60

Val Asp Lys Ser Ser Lys Tyr Ile Ser Leu Phe Ile Arg Asp Ser Gln
65 70 75 80

Pro Ser Asp Ser Ala Thr Tyr Leu Cys Ala Gly Gly Ser Tyr Gly Lys
85 90 95

Leu Thr Phe Gly Gln Gly Thr Ile Leu Thr Val His Pro
100 105

<210> SEQ ID NO 120
<211> LENGTH: 112
<212> TYPE: PRT
<213> ORGANISM: Homo sapiens

<400> SEQUENCE: 120

Glu Ala Gln Val Thr Gln Asn Pro Arg Tyr Leu Ile Thr Val Thr Gly
1 5 10 15

Lys Lys Leu Thr Val Thr Cys Ser Gln Asn Met Asn His Glu Tyr Met
20 25 30

Ser Trp Tyr Arg Gln Asp Pro Gly Leu Gly Leu Arg Gln Ile Tyr Tyr
35 40 45

Ser Met Asn Val Glu Val Thr Asp Lys Gly Asp Val Pro Glu Gly Tyr
50 55 60

Lys Val Ser Arg Lys Glu Lys Arg Asn Phe Pro Leu Ile Leu Glu Ser
65 70 75 80

Pro Ser Pro Asn Gln Thr Ser Leu Tyr Phe Cys Ala Ser Ser Phe Ile
85 90 95

Ser Asn Gln Pro Gln His Phe Gly Asp Gly Thr Arg Leu Ser Ile Leu
100 105 110

<210> SEQ ID NO 121
<211> LENGTH: 131
<212> TYPE: PRT
<213> ORGANISM: Artificial Sequence
<220> FEATURE:
<223> OTHER INFORMATION: Synthetic

<400> SEQUENCE: 121

Met Ala Lys Ser Leu Arg Val Leu Leu Val Ile Leu Trp Leu Gln Leu
1 5 10 15

Ser Trp Val Trp Ser Gln Gln Lys Glu Val Glu Gln Asp Pro Gly Pro
20 25 30

Leu Ser Val Pro Glu Gly Ala Ile Val Ser Leu Asn Cys Thr Tyr Ser
35 40 45

Asn Ser Ala Phe Gln Tyr Phe Met Trp Tyr Arg Gln Tyr Ser Arg Lys
50 55 60

Gly Pro Glu Leu Leu Met Tyr Thr Tyr Ser Ser Gly Asn Lys Glu Asp
65 70 75 80

Gly Arg Phe Thr Ala Gln Val Asp Lys Ser Ser Lys Tyr Ile Ser Leu
85 90 95

```
Phe Ile Arg Asp Ser Gln Pro Ser Asp Ser Ala Thr Tyr Leu Cys Ala
            100                 105                 110

Gly Gly Ser Tyr Gly Lys Leu Thr Phe Gly Gln Gly Thr Ile Leu Thr
        115                 120                 125

Val His Pro
    130
```

```
<210> SEQ ID NO 122
<211> LENGTH: 131
<212> TYPE: PRT
<213> ORGANISM: Artificial Sequence
<220> FEATURE:
<223> OTHER INFORMATION: Synthetic

<400> SEQUENCE: 122

Met His Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Ser Phe Ile Ser Asn Gln Pro Gln His Phe Gly Asp Gly Thr Arg Leu
        115                 120                 125

Ser Ile Leu
    130
```

```
<210> SEQ ID NO 123
<211> LENGTH: 111
<212> TYPE: PRT
<213> ORGANISM: Homo sapiens

<400> SEQUENCE: 123

Gly Glu Ser Val Gly Leu His Leu Pro Thr Leu Ser Val Gln Glu Gly
1               5                   10                  15

Asp Asn Ser Ile Ile Asn Cys Ala Tyr Ser Asn Ser Ala Ser Asp Tyr
            20                  25                  30

Phe Ile Trp Tyr Lys Gln Glu Ser Gly Lys Gly Pro Gln Phe Ile Ile
        35                  40                  45

Asp Ile Arg Ser Asn Met Asp Lys Arg Gln Gly Gln Arg Val Thr Val
    50                  55                  60

Leu Leu Asn Lys Thr Val Lys His Leu Ser Leu Gln Ile Ala Ala Thr
65                  70                  75                  80

Gln Pro Gly Asp Ser Ala Val Tyr Phe Cys Ala Glu Lys Ser Thr Gly
                85                  90                  95

Asn Gln Phe Tyr Phe Gly Thr Gly Thr Ser Leu Thr Val Ile Pro
            100                 105                 110
```

```
<210> SEQ ID NO 124
<211> LENGTH: 113
```

<212> TYPE: PRT
<213> ORGANISM: Homo sapiens

<400> SEQUENCE: 124

Glu Thr Gly Val Thr Gln Thr Pro Arg His Leu Val Met Gly Met Thr
1               5                   10                  15

Asn Lys Lys Ser Leu Lys Cys Glu Gln His Leu Gly His Asn Ala Met
            20                  25                  30

Tyr Trp Tyr Lys Gln Ser Ala Lys Lys Pro Leu Glu Leu Met Phe Val
        35                  40                  45

Tyr Ser Leu Glu Glu Arg Val Glu Asn Asn Ser Val Pro Ser Arg Phe
    50                  55                  60

Ser Pro Glu Cys Pro Asn Ser Ser His Leu Phe Leu His Leu His Thr
65                  70                  75                  80

Leu Gln Pro Glu Asp Ser Ala Leu Tyr Leu Cys Ala Ser Ser Arg Val
                85                  90                  95

Glu Gly Ser Asp Thr Gln Tyr Phe Gly Pro Gly Thr Arg Leu Thr Val
            100                 105                 110

Leu

<210> SEQ ID NO 125
<211> LENGTH: 131
<212> TYPE: PRT
<213> ORGANISM: Artificial Sequence
<220> FEATURE:
<223> OTHER INFORMATION: Synthetic

<400> SEQUENCE: 125

Met Ala Gly Ile Arg Ala Leu Phe Met Tyr Leu Trp Leu Gln Leu Asp
1               5                   10                  15

Trp Val Ser Arg Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Glu Ser Gly Lys Gly Pro
    50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Lys Ser Thr Gly Asn Gln Phe Tyr Phe Gly Thr Gly Thr Ser Leu Thr
        115                 120                 125

Val Ile Pro
    130

<210> SEQ ID NO 126
<211> LENGTH: 132
<212> TYPE: PRT
<213> ORGANISM: Artificial Sequence
<220> FEATURE:
<223> OTHER INFORMATION: Synthetic

<400> SEQUENCE: 126

Met His Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met

```
            20                  25                  30

Gly Met Thr Asn Lys Lys Ser Leu Lys Cys Glu Gln His Leu Gly His
        35                  40                  45

Asn Ala Met Tyr Trp Tyr Lys Gln Ser Ala Lys Lys Pro Leu Glu Leu
    50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110

Ser Arg Val Glu Gly Ser Asp Thr Gln Tyr Phe Gly Pro Gly Thr Arg
        115                 120                 125

Leu Thr Val Leu
    130


<210> SEQ ID NO 127
<211> LENGTH: 116
<212> TYPE: PRT
<213> ORGANISM: Homo sapiens

<400> SEQUENCE: 127

Ala Gln Ser Val Ala Gln Pro Glu Asp Gln Val Asn Val Ala Glu Gly
1               5                   10                  15

Asn Pro Leu Thr Val Lys Cys Thr Tyr Ser Val Ser Gly Asn Pro Tyr
            20                  25                  30

Leu Phe Trp Tyr Val Gln Tyr Pro Asn Arg Gly Leu Gln Phe Leu Leu
        35                  40                  45

Lys Tyr Ile Thr Gly Asp Asn Leu Val Lys Gly Ser Tyr Gly Phe Glu
    50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Val Arg Asp Pro
                85                  90                  95

Thr Val Ser Gly Thr Tyr Lys Tyr Ile Phe Gly Thr Gly Thr Arg Leu
            100                 105                 110

Lys Val Leu Ala
        115


<210> SEQ ID NO 128
<211> LENGTH: 117
<212> TYPE: PRT
<213> ORGANISM: Homo sapiens

<400> SEQUENCE: 128

Gly Ala Val Val Ser Gln His Pro Ser Arg Val Ile Cys Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
```

-continued

```
                85                  90                  95

Ile Arg Asp Arg Ser Gly Gly Glu Thr Gln Tyr Phe Gly Pro Gly Thr
            100                 105                 110

Arg Leu Leu Val Leu
        115


<210> SEQ ID NO 129
<211> LENGTH: 135
<212> TYPE: PRT
<213> ORGANISM: Artificial Sequence
<220> FEATURE:
<223> OTHER INFORMATION: Synthetic

<400> SEQUENCE: 129

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Pro Thr Val Ser Gly Thr Tyr Lys Tyr Ile Phe Gly Thr Gly
        115                 120                 125

Thr Arg Leu Lys Val Leu Ala
    130                 135


<210> SEQ ID NO 130
<211> LENGTH: 131
<212> TYPE: PRT
<213> ORGANISM: Artificial Sequence
<220> FEATURE:
<223> OTHER INFORMATION: Synthetic

<400> SEQUENCE: 130

Met His Leu Leu Leu Leu Leu Leu Gly Pro Gly Ser Gly Leu Gly Ala
1               5                   10                  15

Val Val Ser Gln His Pro Ser Arg Val Ile Cys Lys Ser Gly Thr Ser
            20                  25                  30

Val Lys Ile Glu Cys Arg Ser Leu Asp Phe Gln Ala Thr Thr Met Phe
        35                  40                  45

Trp Tyr Arg Gln Phe Pro Lys Gln Ser Leu Met Leu Met Ala Thr Ser
    50                  55                  60

Asn Glu Gly Ser Lys Ala Thr Tyr Glu Gln Gly Val Glu Lys Asp Lys
65                  70                  75                  80

Phe Leu Ile Asn His Ala Ser Leu Thr Leu Ser Thr Leu Thr Val Thr
                85                  90                  95

Ser Ala His Pro Glu Asp Ser Ser Phe Tyr Ile Cys Ser Ala Ile Arg
            100                 105                 110

Asp Arg Ser Gly Gly Glu Thr Gln Tyr Phe Gly Pro Gly Thr Arg Leu
        115                 120                 125
```

Leu Val Leu
130

<210> SEQ ID NO 131
<211> LENGTH: 113
<212> TYPE: PRT
<213> ORGANISM: Homo sapiens

<400> SEQUENCE: 131

Gln Gln Gln Val Lys Gln Ser Pro Gln Ser Leu Ile Val Gln Lys Gly
1 5 10 15

Gly Ile Ser Ile Ile Asn Cys Ala Tyr Glu Asn Thr Ala Phe Asp Tyr
20 25 30

Phe Pro Trp Tyr Gln Gln Phe Pro Gly Lys Gly Pro Ala Leu Leu Ile
35 40 45

Ala Ile Arg Pro Asp Val Ser Glu Lys Lys Glu Gly Arg Phe Thr Ile
50 55 60

Ser Phe Asn Lys Ser Ala Lys Gln Phe Ser Leu His Ile Met Asp Ser
65 70 75 80

Gln Pro Gly Asp Ser Ala Thr Tyr Phe Cys Ala Ala Lys Arg Gln Gly
85 90 95

Gly Ser Glu Lys Leu Val Phe Gly Lys Gly Thr Lys Leu Thr Val Asn
100 105 110

Pro

<210> SEQ ID NO 132
<211> LENGTH: 114
<212> TYPE: PRT
<213> ORGANISM: Homo sapiens

<400> SEQUENCE: 132

Gly Ala Gly Val Ser Gln Ser Pro Ser Asn Lys Val Thr Glu Lys Gly
1 5 10 15

Lys Asp Val Glu Leu Arg Cys Asp Pro Ile Ser Gly His Thr Ala Leu
20 25 30

Tyr Trp Tyr Arg Gln Ser Leu Gly Gln Gly Leu Glu Phe Leu Ile Tyr
35 40 45

Phe Gln Gly Asn Ser Ala Pro Asp Lys Ser Gly Leu Pro Ser Asp Arg
50 55 60

Phe Ser Ala Glu Arg Thr Gly Gly Ser Val Ser Thr Leu Thr Ile Gln
65 70 75 80

Arg Thr Gln Gln Glu Asp Ser Ala Val Tyr Leu Cys Ala Ser Ser Leu
85 90 95

Gly Gly Ser Ser Glu Thr Gln Tyr Phe Gly Pro Gly Thr Arg Leu Leu
100 105 110

Val Leu

<210> SEQ ID NO 133
<211> LENGTH: 141
<212> TYPE: PRT
<213> ORGANISM: Artificial Sequence
<220> FEATURE:
<223> OTHER INFORMATION: Synthetic

<400> SEQUENCE: 133

Met Ala Lys Ile Leu Gly Ala Ser Phe Leu Val Leu Trp Leu Gln Leu
1 5 10 15

Cys Trp Val Ser Gly Gln Gln Lys Glu Lys Ser Asp Gln Gln Gln Val

```
            20                  25                  30

Lys Gln Ser Pro Gln Ser Leu Ile Val Gln Lys Gly Gly Ile Ser Ile
        35                  40                  45

Ile Asn Cys Ala Tyr Glu Asn Thr Ala Phe Asp Tyr Phe Pro Trp Tyr
    50                  55                  60

Gln Gln Phe Pro Gly Lys Gly Pro Ala Leu Leu Ile Ala Ile Arg Pro
65                  70                  75                  80

Asp Val Ser Glu Lys Lys Glu Gly Arg Phe Thr Ile Ser Phe Asn Lys
                85                  90                  95

Ser Ala Lys Gln Phe Ser Leu His Ile Met Asp Ser Gln Pro Gly Asp
            100                 105                 110

Ser Ala Thr Tyr Phe Cys Ala Ala Lys Arg Gln Gly Gly Ser Glu Lys
        115                 120                 125

Leu Val Phe Gly Lys Gly Thr Lys Leu Thr Val Asn Pro
    130                 135                 140


<210> SEQ ID NO 134
<211> LENGTH: 133
<212> TYPE: PRT
<213> ORGANISM: Artificial Sequence
<220> FEATURE:
<223> OTHER INFORMATION: Synthetic

<400> SEQUENCE: 134

Met His Thr Arg Leu Leu Phe Trp Val Ala Phe Cys Leu Leu Gly Ala
1               5                   10                  15

Asp His Thr Gly Ala Gly Val Ser Gln Ser Pro Ser Asn Lys Val Thr
            20                  25                  30

Glu Lys Gly Lys Asp Val Glu Leu Arg Cys Asp Pro Ile Ser Gly His
        35                  40                  45

Thr Ala Leu Tyr Trp Tyr Arg Gln Ser Leu Gly Gln Gly Leu Glu Phe
    50                  55                  60

Leu Ile Tyr Phe Gln Gly Asn Ser Ala Pro Asp Lys Ser Gly Leu Pro
65                  70                  75                  80

Ser Asp Arg Phe Ser Ala Glu Arg Thr Gly Gly Ser Val Ser Thr Leu
                85                  90                  95

Thr Ile Gln Arg Thr Gln Gln Glu Asp Ser Ala Val Tyr Leu Cys Ala
            100                 105                 110

Ser Ser Leu Gly Gly Ser Ser Glu Thr Gln Tyr Phe Gly Pro Gly Thr
        115                 120                 125

Arg Leu Leu Val Leu
    130


<210> SEQ ID NO 135
<211> LENGTH: 113
<212> TYPE: PRT
<213> ORGANISM: Homo sapiens

<400> SEQUENCE: 135

Gly Glu Ser Val Gly Leu His Leu Pro Thr Leu Ser Val Gln Glu Gly
1               5                   10                  15

Asp Asn Ser Ile Ile Asn Cys Ala Tyr Ser Asn Ser Ala Ser Asp Tyr
            20                  25                  30

Phe Ile Trp Tyr Lys Gln Glu Ser Gly Lys Gly Pro Gln Phe Ile Ile
        35                  40                  45

Asp Ile Arg Ser Asn Met Asp Lys Arg Gln Gly Gln Arg Val Thr Val
    50                  55                  60
```

```
Leu Leu Asn Lys Thr Val Lys His Leu Ser Leu Gln Ile Ala Ala Thr
65                  70                  75                  80

Gln Pro Gly Asp Ser Ala Val Tyr Phe Cys Ala Glu Lys Arg Arg Gly
                85                  90                  95

Gly Ser Glu Lys Leu Val Phe Gly Lys Gly Thr Lys Leu Thr Val Asn
            100                 105                 110

Pro


<210> SEQ ID NO 136
<211> LENGTH: 114
<212> TYPE: PRT
<213> ORGANISM: Homo sapiens

<400> SEQUENCE: 136

Gly Ala Gly Val Ser Gln Thr Pro Ser Asn Lys Val Thr Glu Lys Gly
1               5                   10                  15

Lys Tyr Val Glu Leu Arg Cys Asp Pro Ile Ser Gly His Thr Ala Leu
            20                  25                  30

Tyr Trp Tyr Arg Gln Ser Leu Gly Gln Gly Pro Glu Phe Leu Ile Tyr
        35                  40                  45

Phe Gln Gly Thr Gly Ala Ala Asp Asp Ser Gly Leu Pro Asn Asp Arg
    50                  55                  60

Phe Phe Ala Val Arg Pro Glu Gly Ser Val Ser Thr Leu Lys Ile Gln
65                  70                  75                  80

Arg Thr Glu Arg Gly Asp Ser Ala Val Tyr Leu Cys Ala Ser Ser Pro
                85                  90                  95

Gly Gly Ser Gln Glu Thr Gln Tyr Phe Gly Pro Gly Thr Arg Leu Leu
            100                 105                 110

Val Leu


<210> SEQ ID NO 137
<211> LENGTH: 133
<212> TYPE: PRT
<213> ORGANISM: Artificial Sequence
<220> FEATURE:
<223> OTHER INFORMATION: Synthetic

<400> SEQUENCE: 137

Met Ala Gly Ile Arg Ala Leu Phe Met Tyr Leu Trp Leu Gln Leu Asp
1               5                   10                  15

Trp Val Ser Arg Gly Glu Ser Val Gly Leu His Leu Pro Thr Leu Ser
            20                  25                  30

Val Gln Glu Gly Asp Asn Ser Ile Ile Asn Cys Ala Tyr Ser Asn Ser
        35                  40                  45

Ala Ser Asp Tyr Phe Ile Trp Tyr Lys Gln Glu Ser Gly Lys Gly Pro
    50                  55                  60

Gln Phe Ile Ile Asp Ile Arg Ser Asn Met Asp Lys Arg Gln Gly Gln
65                  70                  75                  80

Arg Val Thr Val Leu Leu Asn Lys Thr Val Lys His Leu Ser Leu Gln
                85                  90                  95

Ile Ala Ala Thr Gln Pro Gly Asp Ser Ala Val Tyr Phe Cys Ala Glu
            100                 105                 110

Lys Arg Arg Gly Gly Ser Glu Lys Leu Val Phe Gly Lys Gly Thr Lys
        115                 120                 125

Leu Thr Val Asn Pro
    130
```

<210> SEQ ID NO 138
<211> LENGTH: 133
<212> TYPE: PRT
<213> ORGANISM: Artificial Sequence
<220> FEATURE:
<223> OTHER INFORMATION: Synthetic

<400> SEQUENCE: 138

```
Met His Thr Arg Leu Leu Cys Trp Ala Ala Leu Cys Leu Leu Gly Ala
1               5                   10                  15

Asp His Thr Gly Ala Gly Val Ser Gln Thr Pro Ser Asn Lys Val Thr
            20                  25                  30

Glu Lys Gly Lys Tyr Val Glu Leu Arg Cys Asp Pro Ile Ser Gly His
        35                  40                  45

Thr Ala Leu Tyr Trp Tyr Arg Gln Ser Leu Gly Gln Gly Pro Glu Phe
    50                  55                  60

Leu Ile Tyr Phe Gln Gly Thr Gly Ala Ala Asp Asp Ser Gly Leu Pro
65                  70                  75                  80

Asn Asp Arg Phe Phe Ala Val Arg Pro Glu Gly Ser Val Ser Thr Leu
                85                  90                  95

Lys Ile Gln Arg Thr Glu Arg Gly Asp Ser Ala Val Tyr Leu Cys Ala
            100                 105                 110

Ser Ser Pro Gly Gly Ser Gln Glu Thr Gln Tyr Phe Gly Pro Gly Thr
        115                 120                 125

Arg Leu Leu Val Leu
    130
```

<210> SEQ ID NO 139
<211> LENGTH: 137
<212> TYPE: PRT
<213> ORGANISM: Mus musculus

<400> SEQUENCE: 139

```
Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135
```

<210> SEQ ID NO 140
<211> LENGTH: 173
<212> TYPE: PRT
<213> ORGANISM: Mus musculus

<400> SEQUENCE: 140

```
Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

<210> SEQ ID NO 141
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is Asn, Asp, His, or Tyr
<220> FEATURE:
<221> NAME/KEY: MISC_FEATURE
<222> LOCATION: (48)..(48)
<223> OTHER INFORMATION: X is Thr or Cys
<220> FEATURE:
<221> NAME/KEY: MISC_FEATURE
<222> LOCATION: (112)..(112)
<223> OTHER INFORMATION: X is Ser, Ala, Val, Leu, Ile, Pro, Phe, Met, or Trp
<220> FEATURE:
<221> NAME/KEY: MISC_FEATURE
<222> LOCATION: (114)..(114)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (115)..(115)
<223> OTHER INFORMATION: X is Gly, Ala, Val, Leu, Ile, Pro, Phe, Met, or Trp

<400> SEQUENCE: 141

```
Xaa Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Xaa
        35                  40                  45

Val Leu Asp Met Lys Ala Met Asp Ser Lys Ser Asn Gly Ala Ile Ala
    50                  55                  60
```

-continued

```
Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Xaa
            100                 105                 110

Val Xaa Xaa Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 142
<211> LENGTH: 173
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (57)..(57)
<223> OTHER INFORMATION: X is Ser or Cys

<400> SEQUENCE: 142

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Xaa Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170


<210> SEQ ID NO 143
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is Asn, Asp, His, or Tyr

<400> SEQUENCE: 143

Xaa Ile Gln Asn Pro Glu Pro Ala Val Tyr Gln Leu Lys Asp Pro Arg
1               5                   10                  15
```

```
Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 144
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is Asn, Asp, His, or Tyr

<400> SEQUENCE: 144

Xaa Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 145
<211> LENGTH: 137
<212> TYPE: PRT
<213> ORGANISM: Artificial Sequence
<220> FEATURE:
<223> OTHER INFORMATION: Synthetic

<400> SEQUENCE: 145

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
```

```
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 146
<211> LENGTH: 137
<212> TYPE: PRT
<213> ORGANISM: Artificial Sequence
<220> FEATURE:
<223> OTHER INFORMATION: Synthetic

<400> SEQUENCE: 146

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 147
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is Asn, Asp, His, or Tyr

<400> SEQUENCE: 147

Xaa Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30
```

```
Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 148
<211> LENGTH: 137
<212> TYPE: PRT
<213> ORGANISM: Artificial Sequence
<220> FEATURE:
<223> OTHER INFORMATION: Synthetic

<400> SEQUENCE: 148

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 149
<211> LENGTH: 137
<212> TYPE: PRT
<213> ORGANISM: Artificial Sequence
<220> FEATURE:
<223> OTHER INFORMATION: Synthetic

<400> SEQUENCE: 149

Asp Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
```

-continued

```
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135


<210> SEQ ID NO 150
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (22)..(22)
<223> OTHER INFORMATION: X is alpha-aminobutyric acid (AABA)

<400> SEQUENCE: 150

Asp Arg Asn Thr Phe Arg His Ser Val Val Val Pro Tyr Glu Pro Pro
1               5                   10                  15

Glu Val Gly Ser Asp Xaa Thr Thr Ile
            20                  25


<210> SEQ ID NO 151
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (13)..(13)
<223> OTHER INFORMATION: X is alpha-aminobutyric acid (AABA)
<220> FEATURE:
<221> NAME/KEY: MISC_FEATURE
<222> LOCATION: (22)..(22)
<223> OTHER INFORMATION: X is alpha-aminobutyric acid (AABA)

<400> SEQUENCE: 151

Asp Arg Asn Thr Phe Arg His Ser Val Val Val Pro Xaa Glu Pro Pro
1               5                   10                  15

Glu Val Gly Ser Asp Xaa Thr Thr Ile
            20                  25
```